United States Patent [19]

Misra et al.

[11] Patent Number: 5,827,868
[45] Date of Patent: Oct. 27, 1998

[54] PROSTAGLANDIN ANALOGS

[75] Inventors: Raj N. Misra, Hopewell; Jagabandhu Das, Hamilton Square; Steven E. Hall, Pennington, all of N.J.; Wen-Ching Han, Holland, Pa.; Philip M. Sher, Plainsboro; Philip D. Stein, Princeton, both of N.J.

[73] Assignee: E. R. Squibb & Sons, Inc., Princeton, N.J.

[21] Appl. No.: 772,830

[22] Filed: Oct. 7, 1991

[51] Int. Cl.[6] .......................... C07D 413/04; A01K 31/42
[52] U.S. Cl. .......................... 514/374; 514/400; 548/236; 548/311.1; 548/333.5
[58] Field of Search ................. 548/236, 311.1, 548/333.5; 514/374, 400

[56] References Cited

U.S. PATENT DOCUMENTS

| | | | |
|---|---|---|---|
| 4,258,058 | 3/1981 | Witte et al. | 424/309 |
| 4,410,526 | 10/1983 | Muchowski et al. | |
| 4,416,896 | 11/1983 | Nakane et al. | 424/285 |
| 4,418,076 | 11/1983 | Nakane et al. | 424/285 |
| 4,443,477 | 4/1984 | Witte et al. | 424/319 |
| 4,463,015 | 7/1984 | Haslanger et al. | 424/285 |
| 4,474,804 | 10/1984 | Das et al. | 424/285 |
| 4,522,949 | 6/1985 | Das et al. | 514/469 |
| 4,536,513 | 8/1985 | Das et al. | 514/469 |
| 4,602,093 | 7/1986 | Baldwin | 548/336 |
| 4,752,613 | 6/1988 | Floyd et al. | 514/438 |
| 4,752,616 | 6/1988 | Hall et al. | 514/510 |
| 4,783,473 | 11/1988 | Hall et al. | 514/382 |
| 4,975,452 | 12/1990 | Sher et al. | 514/438 |
| 5,043,451 | 8/1991 | Ghtani | 546/293 |
| 5,077,309 | 12/1991 | Jones | 514/469 |
| 5,100,889 | 3/1992 | MIsra | 11/365 |

FOREIGN PATENT DOCUMENTS

A-0063538 10/1982 European Pat. Off. .

Primary Examiner—Robert Gerstl
Attorney, Agent, or Firm—Burton Rodney

[57] ABSTRACT

Thromboxane receptor antagonist activity is exhibited by compounds of the formula

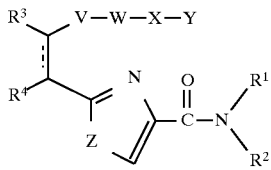

wherein:

V is —$(CH_2)_m$—, —O—, or

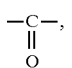

but if V is —O—or

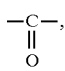

$R^3$ and $R^4$ must complete an aromatic ring;

W is —$(CH_2)_2$—, —CH=CH— or phenylene;

X is a single bond, —CH=CH—, —$(CH_2)_n$—, or —O—$(CH_2)_n$—; or X is branched alkylene or —O—branched alkylene wherein W is linked to Y through a chain n carbon atoms long;

Y is —$CO_2H$, —$CO_2$alkyl, —$CO_2$alkali metal, —$CH_2OH$, —$CONHSO_2R^5$, —$CONHR^6$, or —$CH_2$-5-tetrazolyl;

Z is O or NH;

$R^3$ and $R^4$ are each independently hydrogen or alkyl or $R^3$ and $R^4$ together complete a ring optionally substituted through a ring carbon with a halo, lower alkyl, phenyl, halo (lower alkyl), halophenyl, oxo or hydroxyl group; and the remaining symbols are as defined in the specification.

19 Claims, No Drawings

PROSTAGLANDIN ANALOGS

FIELD OF THE INVENTION

This invention relates to prostaglandin analogs useful as thromboxane $A_2$ receptor antagonists.

BRIEF DESCRIIPITON OF THE INVENTION

A compound of the formula

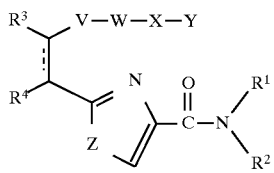

is a thromboxane $A_2$ ($TXA_2$) receptor antagonist or a combined thromboxane $A_2$ receptor antagonist/thromboxane synthetase inhibitor. Compound I is useful, for example, in treating thrombotic or vasospastic disease with good duration of action. In compound I and throughout this specification, the symbols above are defined as follows:

V is —$(CH_2)_m$—, —O—, or

but if V is —O— or

$R^3$ and $R^4$ must complete an aromatic ring;

W is —$(CH_2)_2$—, —CH=CH— or phenylene;

X is a single bond, —CH=CH—, —$(CH_2)_n$—, or —O—$(CH^2)_n$—; or X is branched alkylene or —O—branched alkylene wherein W is linked to Y through a chain n carbon atoms long;

Y is —$CO_2H$, —$CO_2$alkyl, —$CO_2$alkali metal, —$CH_2OH$, —$CONHSO_2R^5$, —$CONHR^6$, or —$CH_2$-5-tetrazolyl;

Z is O or NH;

m is 1, 2, or 3;

n is 1, 2, or 3;

$R^1$ is hydrogen, alkyl, alkenyl, alkynyl, aralkyl, aryl, cycloalkyl, cycloalkylalkyl, cycloheteroalkyl, cycloheteroalkylalkyl, heteroaryl or heteroarylalkyl, or amide

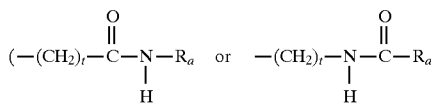

wherein t is 1 to 12 and $R_a$ is alkyl, aryl, cycloalkyl, or cycloalkylalkyl), each of $R^1$ being unsubstituted or optionally substituted with alkyl, aryl, cycloalkyl, or cycloalkylalkyl;

$R^2$ is hydrogen, alkyl, aryl, or aralkyl; or $R^1$ and $R^2$ together with the nitrogen to which they are linked may form a 5- to 8-membered ring;

$R^3$ and $R^4$ are each independently hydrogen, or alkyl; or $R^3$ and $R^4$ together complete a cycloalkyl, cycloalkenyl, phenyl, naphthyl, partially saturated naphthyl, pyridinyl, piperidinyl, pyrrolyl, pyrimidinyl, triazinyl, bornanyl, bornenyl, norbornanyl, norbornenyl, bicyclooctanyl, furanyl, pyranyl, dioxanyl, dioxolyl, dioxazolyl, oxazolyl, isoxazolyl, oxazinyl, isoxazinyl, imidazolyl, morpholinyl, oxepinyl, diazepinyl, thiophenyl, thiopyranyl, or thiazolyl ring, optionally substituted through a carbon atom with a halo, lower alkyl, phenyl, halo(lower alkyl) such as trifluoromethyl, halophenyl, oxo or hydroxyl group;

$R^5$ is alkyl, aryl or aralkyl; and $R^6$ is hydrogen, alkyl, aryl, or aralkyl.

The dashed line (–) denotes that a single or double bond may be present.

Preferred compounds of formula I have the formula

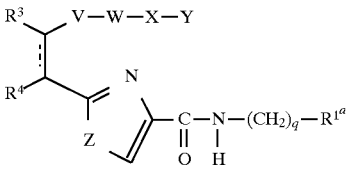

wherein q is an integer from 1 to 7 and $R^{1a}$ is alkyl, cycloalkyl (e.g., cyclohexyl) or aryl (e.g., phenyl or chlorophenyl). Also preferred are compounds wherein $R^3$-$R^4$ is cycloalkyl (such as Examples 1 to 4 hereinafter), cycloalkenyl (such as Example 11), aryl (such as Examples 5 to 9, 12 to 14, and 23), alkyl (such as Example 15), alkenyl (such as Example 10), dioxolanyl (such as Examples 16 to 19), or dioxanyl (such as Examples 20 to 22). Most preferred are compounds wherein $R^3$-$R^4$ is cyclopentyl (Examples 1 to 4), cyclohexenyl (Example 11), phenyl (Examples 5 to 9, 12 to 14, and 23), ethyl (Example 15), butenyl (Example 10), dioxolanyl (Examples 16 to 19) or dioxanyl (Examples 20 to 22).

DETAILED DESCRIPTION OF THE INVENTION

Definition of Terms

The following definitions apply to the terms used throughout this specification, unless otherwise limited in specific instances.

The terms "alkyl" and "alkylene" refer to straight and branched chain radicals of up to 12 carbons, preferably 1 to 4 carbons, such as methyl, ethyl, propyl, isopropyl, butyl, t-butyl, isobutyl, pentyl, hexyl, isohexyl, heptyl, 4,4-dimethyl-pentyl, octyl, 2,2,4-trimethylpentyl, nonyl, decyl, undecyl, dodecyl, the various branched chain isomers thereof and the like, which may be substituted with one or two trifluoromethyl, halo or hydroxyl groups. The term "lower alkyl" refers to alkyl groups of 1 to 4 carbons.

The term "cycloalkyl" refers to saturated cyclic hydrocarbon groups containing 3 to 8 carbons, such as cyclopropyl, cyclobutyl, cyclopentyl, cyclohexyl, cycloheptyl, and cyclooctyl.

The term "cycloalkenyl" refers to unsaturated, nonaromatic, cyclic hydrocarbon groups containing 5 to 8 carbons, such cyclopentenyl, cyclohexenyl, cycloheptenyl, and cyclooctenyl.

The term "aryl" or "Ar" refers to monocyclic or bicyclic aromatic groups containing from 6 to 10 carbons in the ring portion, such as phenyl and naphthyl, which may include 1 or 2 substituents on either the phenyl or naphthyl such as alkyl, trifluoromethyl, halogen (Cl, Br, I or F), alkoxy, arylalkoxy, hydroxy, alkylthio, alkylsulfinyl, alkylsulfonyl, phenylthio, phenylsulfinyl and/or phenylsulfonyl.

The term "aralkyl" refers to alkyl groups as discussed above having an aryl substituent, such as benzyl.

The term "halogen" or "halo" refers to chlorine, bromine, fluorine or iodine, with chlorine being preferred.

The term "alkenyl" refers to carbon chains of 2 to 12 carbons, preferably 3 to 10 carbons, having at least one double bond. With respect to the $R^1$ substituent, the alkenyl group will be separated from "N" by at least one saturated carbon moiety such as —$(CH_2)_q$— wherein q can be 1 to 14, such as 2-propenyl, 2-butenyl, 3-butenyl, 2-pentenyl, 4-pentenyl and the like, and may include a halogen substituent such as I, Cl, or F.

The term "alkynyl" refers to carbon chains of 2 to 12 carbons, preferably 3 to 10 carbons, having at least one triple bond. With respect to the $R^1$ substituent, the alkynyl group will be separated from "N" by at least one saturated carbon moiety such as —$(CH_2)_q$— wherein q can be 1 to 14, such as 2-propynyl, 2-butynyl, 3-butynyl and the like.

The term "cycloheteroalkyl" as used herein as an $R^1$ substituent refers to 5-, 6- or 7-membered saturated rings that include 1 or 2 heteroatoms such as nitrogen, oxygen and/or sulfur, and which are linked to the "N" of the

group through a carbon atom either beta or gamma to a heteroatom, such as

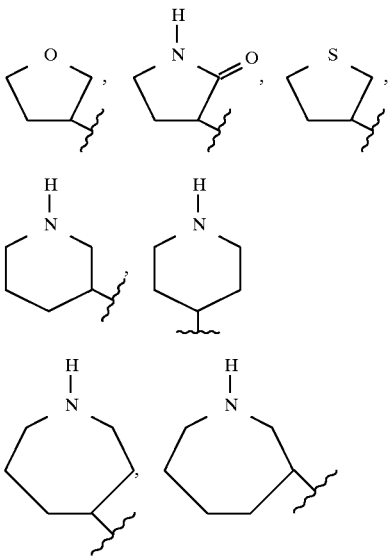

and the like.

The term "heteroaryl" or "heteroaromatic" as an $R^1$ substituent refers to 5- or 6-membered aromatic rings that include 1 or 2 heteroatoms such as nitrogen, oxygen or sulfur, which are not directly linked through a heteroatom to the "N" of the

group, such as

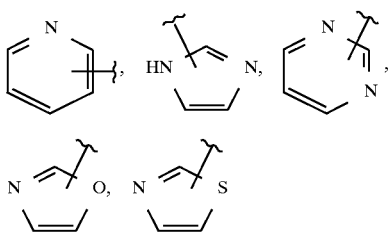

and the like.

The term "cycloheteroalkylalkyl" as used herein with respect to $R^1$ refers to 5-, 6- or 7-membered saturated rings that include 1 or 2 heteroatoms such as nitrogen, oxygen or sulfur, and are linked to the "N" of the

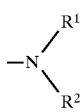

group through a $(CH_2)_x$ chain wherein x is 1 to 12, preferably 1 to 8, such as

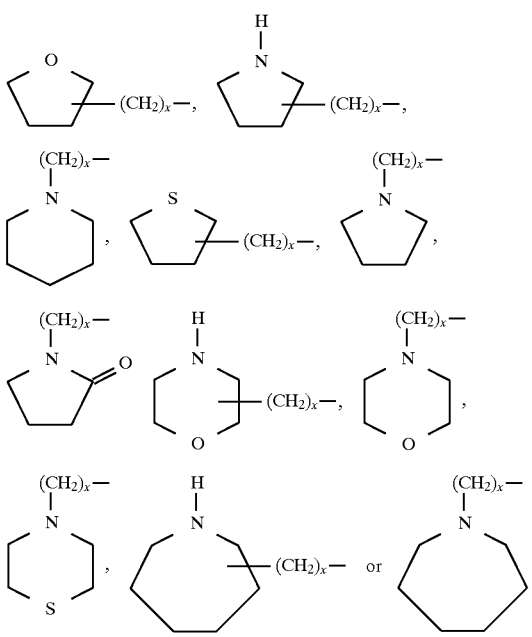

and the like.

The term "heteroarylalkyl" as used herein with respect to $R^1$ refers to 5-, 6- or 7-membered aromatic rings that include 1 to 4 nitrogen and/or 1 or 2 oxygen or sulfur atoms, and is linked to the "N" of the

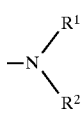

group through a —$(CH_2)_x$—chain where x is 1 to 12, preferably 1 to 8, such as

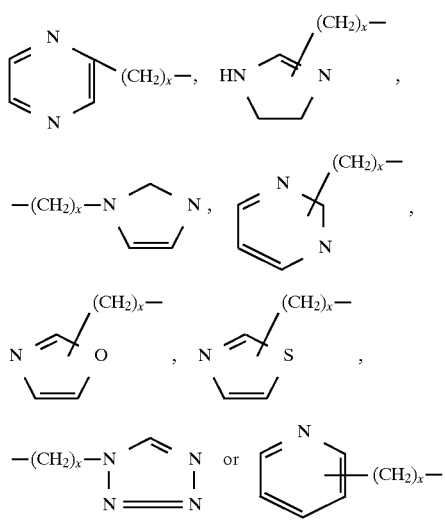

and the like.

Processes of Preparation

Compounds of the invention may be prepared as follows. A diacid

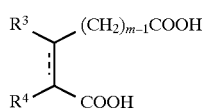

II is heated to about 100° to 125° C. to yield an anhydride

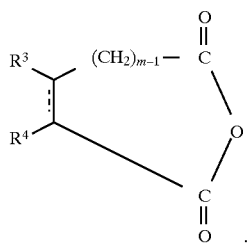

III

Diacid II may be prepared from the associated diesters and diols by methods generally known in the art. Anhydride III may also be prepared by other methods known in the art. Anhydride III is reacted with a reducing agent (e.g., sodium borohydride) in an inert solvent (e.g., tetrahydrofuran) under an inert atmosphere (e.g., argon) at about −10° to 10° C. to form lactones

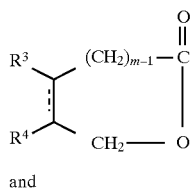

IV and

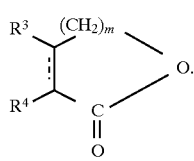

V

It should be understood that lactones IV and V are identical when anhydride III has an axis of symmetry. It should be further understood that when m is 1, lactone V could be substituted for lactone IV in the procedures described hereinafter.

Lactone IV is further reduced (e.g., with diisobutylaluminum hydride) in an inert solvent (e.g., toluene) under an inert atmosphere (e.g., argon) at about −70° to −78° C. to form a lactol

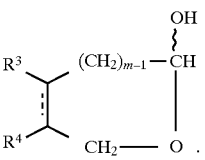

VI

Meanwhile, phenyl bromide

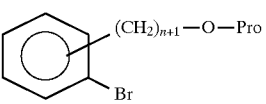

VII may be treated with, for example, magnesium turnings and a catalytic amount of iodine in an inert solvent (e.g., tetrahydrofuran) under an inert atmosphere (e.g., argon) at about 35° to 70° C. to form a Grignard reagent

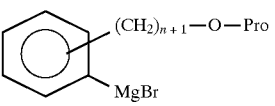

VIII

Lactol VI and Grignard reagent VIII are then reacted at about −10° to 10° C. in an inert solvent (e.g., tetrahydrofuran) under an inert atmosphere (e.g., argon) to form a mono-protected triol

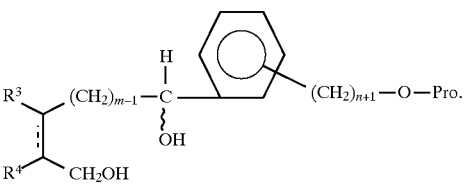

IX

"Pro" in the foregoing represents an oxygen-protecting group such as benzyl, methoxymethyl, or a silyl protecting group such as

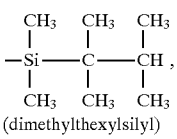

(dimethylthexylsilyl)

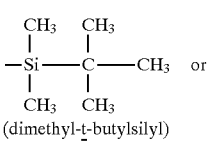  or (dimethyl-t-butylsilyl)

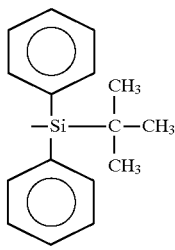

(diphenyl-t-butylsilyl) and the like.

Triol IX wherein Pro is other than benzyl is treated with an acid (e.g., acetic acid) in the presence of a catalyst (e.g., 20% palladium hydroxide on carbon) under a hydrogen atmosphere at about 20° to 30° C. to form an alcohol

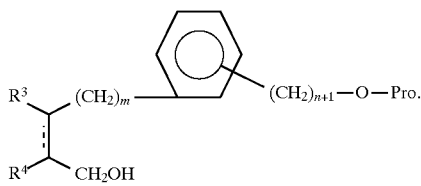

Alcohol X is treated with (1) a protecting agent (e.g., acetic anhydride) and a base (e.g., pyridine) under an inert atmosphere (e.g., argon) at about −10° to 25° C., (2) $MnSO_4$-treated Jones reagent at about −10° to 25° C. in an inert organic solvent (e.g., acetone), and (3) acidic alcohol (e.g., acetyl chloride in methanol) to form an alcohol-ester

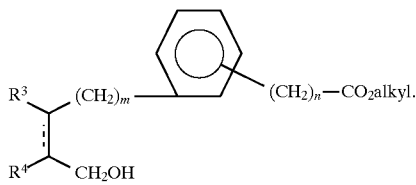

(Jones reagent is discussed in Fieser and Fieser, *Reagents in Organic Synthesis,* Vol. 1, page 242 (1967)). Alcohol-ester XI is treated with $MnSO_4$-treated Jones reagent in an inert organic solvent (e.g., acetone) under an inert atmosphere (e.g., argon) at about −10° to 25° C. to form an acid-ester

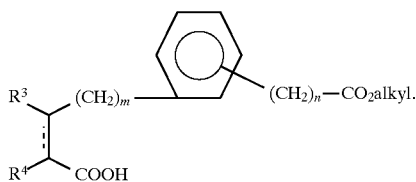

Acid-ester XII is coupled with a serine amide

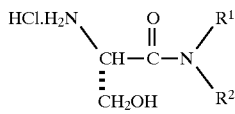

in an organic solvent (e.g., dimethylformamide) in the presence of a coupling reagent such as 1-(3-dimethylaminopropyl)-3-ethylcarbodiimide hydrochloride (WSC) or dicyclohexylcarbodiimide (DCC) and a catalyst such as 1-hydroxybenzotriazole (HOBt) hydrate and an amine base (e.g., triethylamine) at about 0° to 30° C. to form an amide

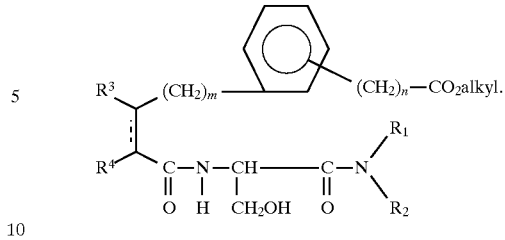

Amide XIV undergoes cyclodehydration by treatment with an amine base (e.g., triethylamine) and a sulfonyl halide (e.g., mesyl chloride) in an inert organic solvent (e.g., methylene chloride) at about 0° to 30° C., followed by an alkali metal carbonate (e.g., potassium carbonate) in an inert solvent (e.g., acetone) at about 20° to 30° C. to form an oxazoline

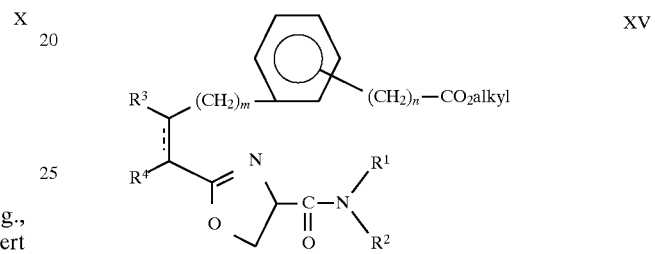

Oxazoline XV is treated with an oxidizing agent (e.g., cupric bromide) in the presence of a base such as 1,8-diazabicyclo[5.4.0]undec-7-ene (DBU) in an inert organic solvent or solvent mixture (e.g., ethyl acetate/chloroform) under an inert atmosphere (e.g., argon) at about 20° to 30° C. to form compound I wherein V is —$(CH_2)_m$—, W is phenylene, X is —$(CH_2)_n$—, Y is —$CO_2$alkyl, and Z is O.

Alternatively, oxazoline XV is treated with nickel peroxide in the presence of an inert solvent (e.g., methylene chloride) under an inert atmosphere (e.g., argon) to form compound I. This is a preferred method when $R^3$ and $R^4$ constitute a ring with more than one heteratom.

In a further alternative, lactone IV is treated with a reducing agent (e.g., lithium aluminum hydride) in an inert solvent or solvent mixture (e.g., ether/tetrahydrofuran) at about −5° to 5° C. to form a diol

Diol XVI reacts with a strong base (e.g., sodium hydride) in an inert solvent (e.g., tetrahydrofuran) at about 45° to 55° C., followed by an acid-stable protecting agent (e.g., t-butyl-chlorodiphenylsilane) to form the monoprotected diol

Protected alcohol XVII is then treated with an activating agent (e.g., mesyl chloride) in the presence of an amine base (e.g., triethylamine) in an inert solvent (e.g., methylene chloride) at about −25 to 15° C., followed by an iodizing agent (e.g., sodium iodide) in an inert solvent (e.g., acetone) to form an iodide

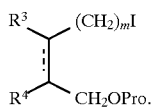
XVIII

Iodide XVIII reacts with Grignard reagent VIII in the presence of dilithium tetrachloro-cuprate (prepared as described in M. Tamura and J. Kochi, *Synthesis*, 303 (1971)) at about −78 to 30° C. to form a diprotected diol

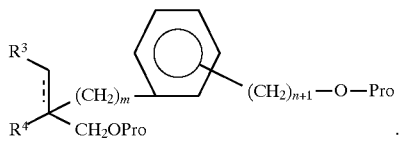
XIX

The protecting groups in diol XIX are selected from those groups defined by "Pro" wherein the phenylalkanol sidechain protecting group is acid-labile and the other protecting group is acid-stable.

Protected compound XIX is treated with Jones reagent in an inert solvent (e.g., acetone) at about −5 to 5° C., followed by an esterifying agent (e.g., diazomethane) in an organic solvent (e.g., ether) to form an ester

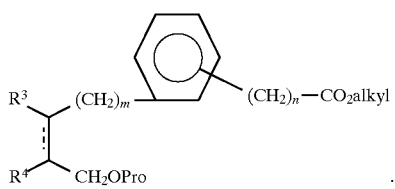
XX

Ester XX is treated with a deprotecting agent (e.g., tetra-n-butylammonium fluoride where Pro is a silyl protecting group) in an organic solvent (e.g., tetrahydrofuran) at about 20° to 30° C. to form alcohol-ester XI, which may be treated as described previously herein to form compound I.

In a further alternative, alcohol-ester XI may be treated with an oxidizing agent (e.g., manganese dioxide) in an inert solvent (e.g., methylene chloride) under an inert atmosphere (e.g., argon) at about 20° to 30° C. to form an aldehyde-ester

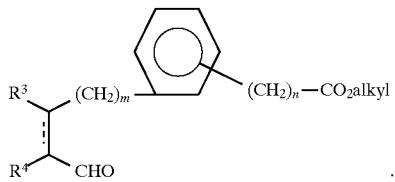
XXI

Aldehyde-ester XXI reacts with a strong oxidizing agent (e.g., sodium chlorite) in an organic solvent (e.g., t-butanol) in the presence of 2-methyl-2-butene at about 20° to 30° C. to form acid-ester XII.

Compounds wherein V is —C(O)— may be prepared as follows. In all compounds cited in the pathway wherein V is —C(O)—, $R^3$ and $R^4$ complete an aromatic ring.

Compound III wherein m is 1 reacts with Grignard reagent VIII in an inert solvent (e.g., tetrahydrofuran) in an inert atmosphere (e.g., argon) at about −5° to 5° C., after which the solution warmed to about 20° to 30° C. to form protected alcohol-acid

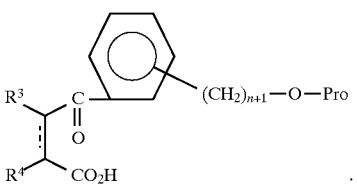
XXII

Protected alcohol-acid XXII is coupled to amine hydrochloride salt XIII under the conditions described for coupling of compounds XII and XIII to form the protected alcohol-amide

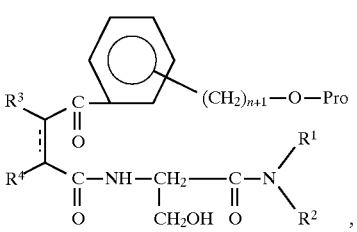
XXIII which undergoes cyclodehydration and oxidation as described for compounds XIV and XV to form the protected alcohol-oxazole

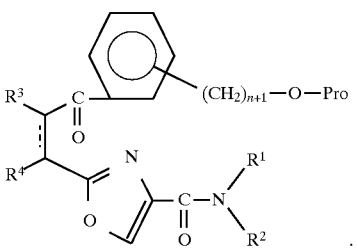
XXIV

The protected alcohol-oxazole XXIV is treated with Jones reagent as described for alcohol X to form compound I wherein $R^3$ and $R^4$ complete an aromatic ring, V is —C(O)—, W is phenylene, X is —(CH$_2$)$_n$—, Y is —CO$_2$alkyl, and Z is O.

Compounds wherein V is —O— may be prepared as follows. In all compounds cited in the pathway wherein V is —O—, $R^3$ and $R^4$ complete an aromatic ring. Iodide-acid

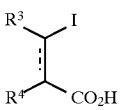
XXV (e.g., 2-iodobenzoic acid) is treated with a protecting compound (benzyl bromide preferred) in the presence of an alkali metal carbonate in an inert organic solvent (e.g., acetone) at about −20° to 30° C. to form an ester-iodide

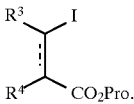
XXVI

This compound is coupled with an alcohol-ester

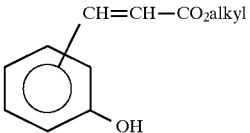
XXVII which may be prepared by treating the associated acid with an esterifying agent (e.g, diazomethane) in an organic solvent or solvent mixture (e.g., ether/methanol) at about 20° to 30° C. Compounds XXVI and XXVII are coupled by treatment with a catalyst (e.g., cupric oxide) and a base (e.g., potassium carbonate) in an inert organic solvent (e.g., pyridine) in an inert atmosphere (e.g., argon) at about 120° to 130° C. to form an olefin diester

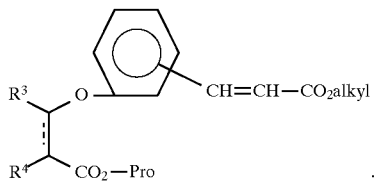

XXVIII

Olefin diester XXVIII may be reduced in the presence of a catalyst (e.g., palladium hydroxide on activated carbon) in an inert solvent or solvent mixture (e.g., ethyl acetate/methanol) under a hydrogen atmosphere at about 20° to 30° C. to form an acid-ester

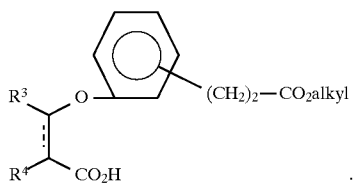

XXIX

Acid-ester XXIX is coupled with amine hydrochloride salt XIII under the conditions described for the coupling of compounds XII and XIII, after which the coupled compound undergoes cyclodehydration and oxidation as described for compounds XIV→XV→I to form compound I wherein V is —O—, W is phenylene, X is —$(CH_2)_n$—, Y is —$CO_2$alkyl, Z is O, and $R^3$ and $R^4$ complete an aromatic ring.

In a further alternative, diol XVI is reacted with an acylating agent (e.g., acetic anhydride) in the presence of a base (e.g., pyridine) and a catalyst (e.g., DMAP) in an organic solvent (e.g., methylene chloride) at about 20° to 30° C. to form a diacyl compound

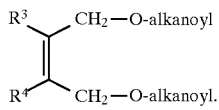

XXX

Diacyl compound XXX is treated with Grignard reagent VIII at about −5 to 5° C. in an inert solvent (e.g., tetrahydrofuran) in the presence of dilithium copper tetrachloride at about −78° C. in an inert solvent (e.g., tetrahydrofuran) to form an acyl-protected alcohol

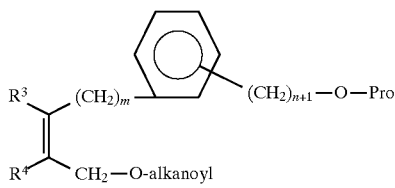

XXXI wherein m is 1.

Compound XXXI is treated with Jones reagent in an inert solvent (e.g., acetone) at about −5° to 10° C., with warming to 20° to 30° C., followed by an alkylating agent (e.g., diazomethane) to form an acylate-ester

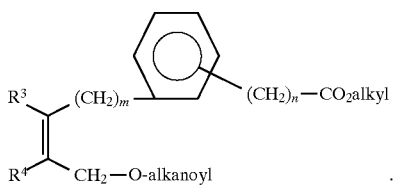

XXXII

Acyl-ester XXXII is treated with a base (e.g., potassium carbonate) in an organic solvent (e.g., methanol) at about −5° to 10° C., with warming allowed up to about 30° C., to form alcohol-ester XI. Alcohol-ester XI is treated as described for compounds XI→XII→XIV→XV→I.

In a further alternative, the alpha and/or omega sidechain may be formed prior to completion of the $R^3$–$R^4$ ring. This alternative is especially useful for compounds having one or more oxygen heteroatoms in the $R^3$–$R^4$ ring. The compounds of the invention wherein $R^3$–$R^4$ complete a dioxolane ring may be prepared from monoprotected diol XVII wherein m is 1, $R^3$ and $R^4$ are each hydrogen and Pro is preferred to be benzyl. This compound is acylated using, for example, acetic anhydride and pyridine, to form a monoacyl compound

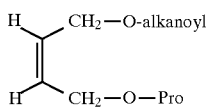

XXXIII

Monoacyl compound XXXIII is reacted with Grignard reagent VIII as described for diacyl compound XXX to form diprotected diol XIX wherein $R^3$ and $R^4$ are hydrogen. This compound is oxidized and esterified as described for the preparation of compound XX. The so-formed compound XX is treated with an oxidizing agent (e.g., 4-methylmorpholine-N-oxide) in an organic solvent (e.g., tetrahydrofuran) in the presence of a catalyst (e.g., osmium tetroxide) to form a diol

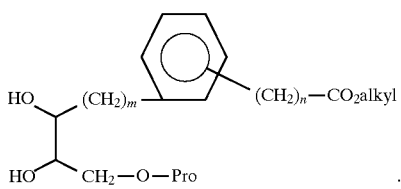

XXXIV

Diol XXXIV is treated with N-bromosuccinimide and dimethylsulfoxide at about 55° to 65° C. to form cyclized protected alcohol-ester XX wherein $R^3$ and $R^4$ complete a dioxolanyl ring. This compound is alcohol-deprotected by, for example, hydrogenation ($H_2$ balloon) when Pro is benzyl in the presence of a catalyst (e.g., palladium hydroxide on charcoal) in an organic solvent (e.g., ethyl acetate) to form the associated alcohol-ester of formula XI. This compound, in turn, is treated as described for compounds XI→XII→XIV→XV→I to form compound I wherein $R^3$ and $R^4$ complete a dioxolanyl ring.

Alternatively, oxygen heterocycles may be derived from a monoprotected diol

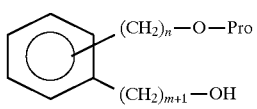

XXXV wherein Pro is preferred to be dimethylthexylsilyl, which may be prepared as described above for diol XVII. Diol XXXV is reacted with an oxidizing agent (e.g., pyridinium dichromate) in an inert solvent (e.g., methylene chloride) to form an aldehyde

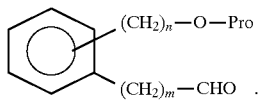   XXXVI

Protected alcohol-aldehyde XXXVI is treated with potassium hexamethyldisilazane, bis(2,2,2-trifluoroethyl)methoxycarbonylmethyl)phosphonate, and 1,4,7,10,13,16-hexaoxacyclooctadecane (18-crown-6) in an organic solvent or solvent mixture (e.g., toluene, tetrahydrofuran) at about −78° C. to form an ester

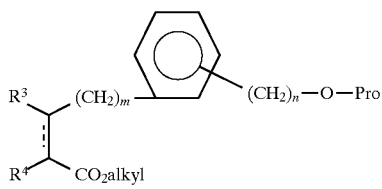   XXXVII wherein $R^3$−$R^4$ is —CH=CH—. This compound is hydroxylated in an organic solvent (e.g., tetrahydrofuran) by, for example, N-methyl-morpholine-N-oxide/osmium tetroxide in water at about 20° to 30° C. to form a mono-protected triol-ester

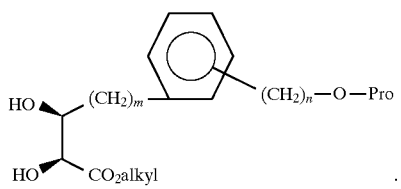   XXXVIII

Triol-ester XXXVIII is cyclized, for example, by treatment with an aldehyde (e.g., acetaldehyde) and a catalyst (e.g., p-toluene-sulfonic acid) at about −5° to 5° C. in an organic solvent (e.g., toluene) to form a cyclized ester, which is hydrolyzed to the acid by treatment with an alkai metal hydroxide (e.g., lithium hydroxide) in water to form protected alcohol-acid

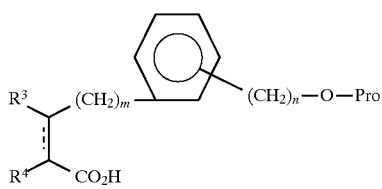   XXXIX wherein $R^3$ and $R^4$ complete a dioxolanyl ring optionally substituted as described in formula I. This compound is reacted with amine hydrochloride XIII, cyclized and oxidized as described above, treated with a deprotecting agent (e.g., tetra-n-butylammonium fluoride) in an organic solvent (e.g., tetrahydrofuran), followed by Jones reagent as described above to form compound I wherein V is —$(CH_2)_m$—, W is phenylene, X is —$(CH_2)_n$—, Y is —$CO_2$alkyl, Z is O, and $R^3$ and $R^4$ complete an optionally substituted dioxolanyl ring.

Alternatively, to prepare ring-substituted oxygen heterocycles, a phenyloxazoline

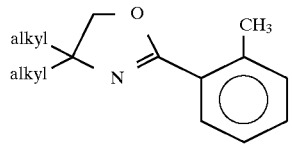   XL is treated with a lithium base (e.g., n-butyl lithium) in an organic solvent at about −45° to −55° C. to form a phenyloxazoline lithium salt

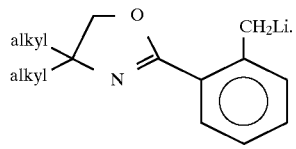   XLI

Lithium salt XLI is coupled with an epoxide

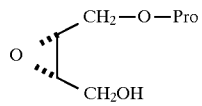   XLII in an organic solvent (e.g., tetrahydrofuran) at about −50° to 10° C. to form an oxazoline-triol

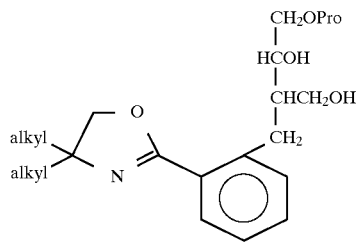   XLIII

Oxazoline-triol XLIII is treated with acidic alcohol (e.g., acetyl chloride in methanol) at about −5° to 10° C. to form an ester-triol

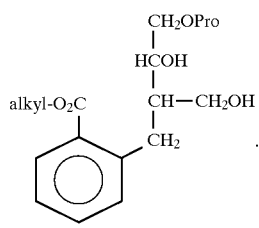   XLIV

Ester-triol XLIV is cyclized by treatment with a catalyst (e.g., p-toluenesulfonic acid) in an organic solvent (e.g., 2,2-dimethoxypropane) at about 20° to 30° C. to form cyclized protected alcohol-ester XI wherein $R^3$ and $R^4$ complete a dioxanyl ring, optionally substituted as described in formula I. The ring substituents may later be exchanged for other substituents by treatment with, for example, an aldehyde (e.g., 2-chloro-benzaldehyde) in the presence of a catalyst (e.g., p-toluenesulfonic acid) in an organic solvent (e.g., toluene) at about 20° to 30° C.

For compounds wherein Z is NH, acids such as compounds XII, XXII, and XXIX are coupled with a diprotected amino acid

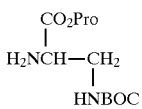    XLV (wherein BOC is t-butoxycarbonyl) in the presence of a coupling agent such as WSC and HOBt in methylene chloride for about 12 to 90 hours, employing an acid:amine molar ratio of about 1.2:1 to about 1:1. The resulting amide undergoes a thionation reaction (preceded by Jones oxidation and esterification when compound XXII is used) with Lawesson's reagent in the presence of benzene at about 50° to 65° C. for about 1 to 4 hours to form a thioamide

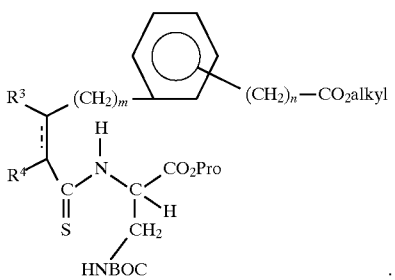    XLVI

Ester XLVI is cyclized in an inert solvent (e.g., acetonitrile, methylene chloride or THF) with triphenylphosphine in an ester:triphenyl-phosphine molar ratio of about 0.8:1 to 1:1, along with carbon tetrachloride in the presence of an amine base (e.g., triethylamine or diisopropylethylamine) to form an imidazoline

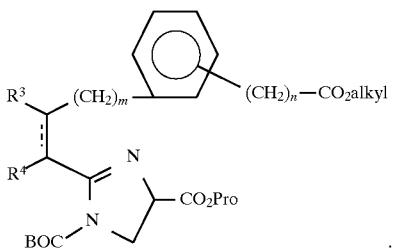    XLVII

Imidazoline XLVII is then conventionally deprotected to remove Pro to form an acid

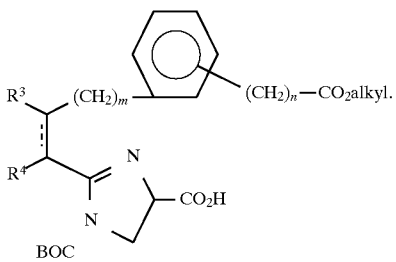    XLVIII

Next, acid XLVIII is coupled with an amine

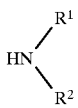    XLIX in the presence of an amine base (e.g., pyridine or triethylamine) under an inert atmosphere (e.g., argon) in the presence of a coupling agent such as WSC and HOBT and chloroform, employing a molar ratio of about 0.8:1 to 1.2:1 to form an amide

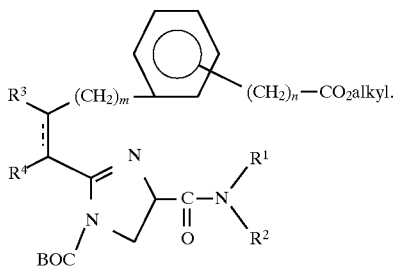    L

Amide L is then treated with a deprotecting agent (e.g., trifluoroacetic acid) in an inert solvent (e.g., methylene chloride) to remove the BOC group and form an imidazoline of the formula

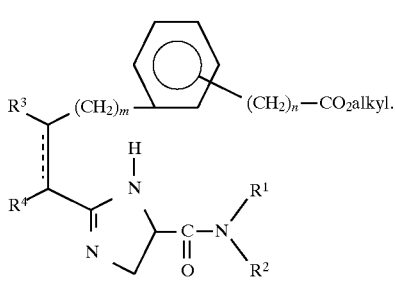    LI

Imidazoline LI is treated with an oxidizing agent (e.g., manganese dioxide) in an inert solvent (e.g., chloroform) to form imidazole compounds of formula I.

Compounds of the invention wherein X is —O—$(CH_2)_n$— may be prepared as follows.

Bromophenol

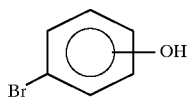    LII is treated with bromomethyl methyl ether to form

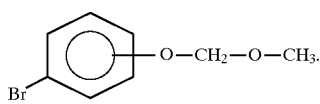    LIII

Compound LIII is metallated by a metal-halogen exchange using n-butyllithium in THF and condensed with lactol VI as described for compounds VI+VIII→IX to form a methoxy diol

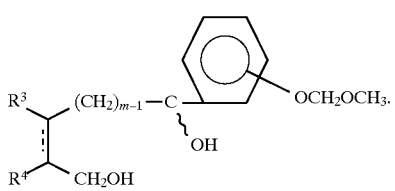    LIV

The condensed compound LIV is then subjected to hydrogenolysis by treatment with hydrogen in the presence of a catalyst such as palladium on charcoal in acetic acid, to form the alcohol

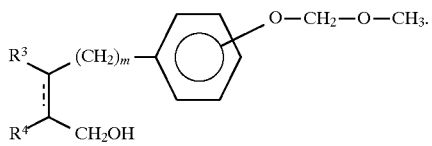
LV

Alcohol LV is deprotected by treatment with, for example, a solution of methanol and aqueous hydrochloric acid to form a diol

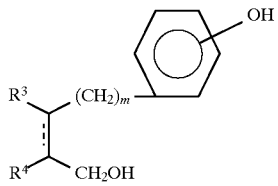
LVI

Diol LVI is then deprotonated by treating a solution in tetrahydrofuran with a molar equivalent of sodium hydride or one to four equivalents of a carbonate base such as potassium carbonate. The resulting phenoxide solution is alkylated with a haloalkanoic acid ester LVII Halo —$(CH_2)_n$— $CO_2$alkyl employing a phenoxide:haloester molar ratio of about 1:2 to 3:1 in the presence of an inert organic solvent (e.g., THF, DMF or dimethoxyethane) to form alcohol-ester

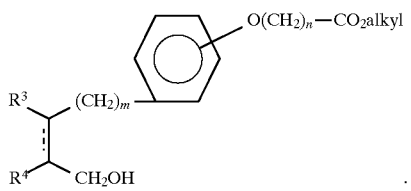
LVIII

Alcohol-ester LVIII is treated with Jones reagent at about −10° to 10° C. in an organic solvent (e.g., acetone) to form an acid-ester

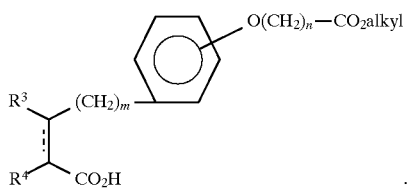
LIX

Acid-ester LIX is treated as described for compound XII to form compound I wherein X is —O—$(CH_2)_n$—.

Compounds of formula I wherein X is —CH=CH— may be prepared by treatment of protected alcohol XX with lithium diisopropylamide at −78° under an inert atmosphere (e.g., argon). The resulting mixture is treated with diphenyl diselenide at about −78° to 25° C., to form the corresponding selenide

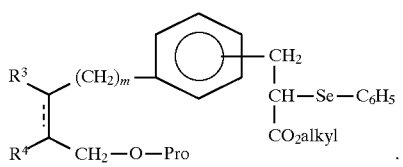
LX

Selenide LX in an inert organic solvent (e.g., ethyl acetate and/or methanol) is treated with an
oxidizing agent (e.g., aqueous hydrogen peroxide) to form the cinnamate

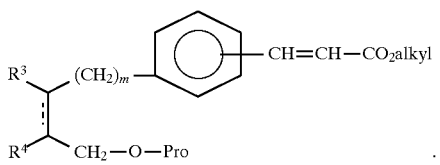
LXI

The protecting group is removed from cinnamate LXI (e.g., with tetra-n-butylammonium fluoride when Pro is a silyl protecting group) in an inert solvent such as THF to form the alcohol

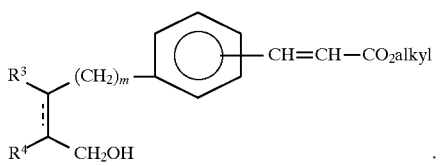
LXII which may then be employed to form compounds of formula I wherein X is —CH=CH— employing procedures described for treatment of alcohol-ester XI.

Compounds of the invention wherein X is a single bond may be prepared starting with a protected bromophenylmethanol, which is converted to a Grignard reagent and condensed with lactol VI as described for compounds VIII and IX. The resulting monoprotected triol (having —$CH_2$— instead of —$(CH_2)_{n+1}$— in compound IX) is then protected by treatment with, for example, a solution of acetic anhydride and pyridine in the presence of 4-dimethylaminopyridine to form a protected alcohol-diacetate

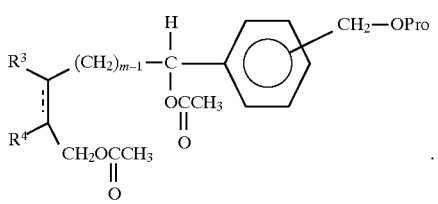
LXIII

The protected alcohol LXIII is then deprotected using conventional procedures, and the resulting alcohol is subjected to a Jones oxidation employing procedures described hereinbefore to form a crude acid. The crude acid is deacetylated by reaction with aqueous hydroxide in the presence of an inert organic solvent such as THF and then esterified, for example, by treatment with a diazoalkane (e.g., diazomethane) or acidic alcohol, to form a diol-ester

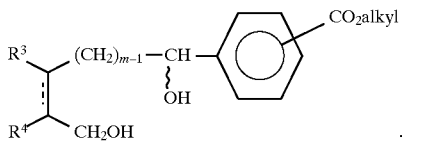
LXIV

The diol-ester LXIV is then subjected to hydrogenolysis as described for diol LIV to provide the alcohol-ester

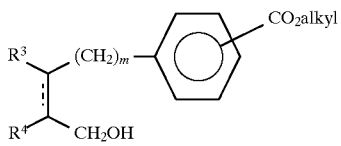
LXV which is treated as described for alcohol-ester XI to form compound I wherein X is a single bond.

Compounds of formula I wherein X is branched alkylene or —O— branched alkylene may be prepared by the procedures for compound I wherein X is —$(CH_2)_n$— or —O—$(CH_2)_n$—, using branched alkyl analogues of phenyl bromide VII.

The compounds of formula I wherein W is —CH=CH— or —$(CH_2)_2$— may be prepared as follows.

Compounds of the invention where W is —CH=CH— and preferably in the cis form are prepared starting with a lactol

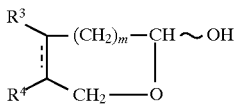  LXVI which may be prepared by the procedures described for lactol VI. Lactol VI is. treated with a suspension of carboxyalkyltriphenylphosphonium bromide in an organic solvent (e.g., THF) and potassium-tert-amylate in an organic solvent (e.g., toluene) at about 0° to 5° C., followed by an esterification reaction to form an olefin alcohol-ester

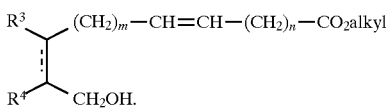  LXVII

Alcohol-ester LXVII may be treated as described for compound XI to form compound I wherein W is —CH=CH—.

Compounds of formula I wherein W is —$(CH_2)_2$— may be prepared from the corresponding acids wherein W is —CH=CH— by hydrogenation using, for example, a hydrogenation catalyst (e.g., palladium on carbon) in an inert organic solvent (e.g., ethyl acetate or acetic acid).

Compounds of formula I wherein Y is —$CO_2$—alkali metal can be prepared from the corresponding esters by treatment with bases such as lithium hydroxide or potassium hydroxide. The corresponding acids (wherein Y is —$CO_2H$) are prepared by neutralizing the foregoing alkali metal salts with an acid (e.g., dilute hydrochloric acid or oxalic acid).

Compounds of the invention wherein Y is —$CONHSO_2R^5$ are prepared by treating the associated acids (wherein Y is —$CO_2H$) with a sulfonamide

  LXVIII in the presence of a coupling agent (e.g., carbonyldiimidazole or WSC) in the presence of an amine (e.g., DMAP) under an inert atmosphere (e.g., argon).

Compounds of formula I wherein Y is —$CONHR^6$ wherein $R^6$ is other than hydrogen may be prepared from the corresponding acid by treatment with WSC in the presence of DMF, HOBt, an organic base (e.g., triethylamine) and an amine LXIX

 $HNHR^6$.

When $R^6$ in compound I is hydrogen, ammonium chloride is used in place of amine LXIX.

Use and Utility

The compounds of this invention are thromboxane receptor antagonists and as such are useful as inhibitors of thromboxane receptor mediated actions. The term "thromboxane receptor antagonist" includes compounds that are so-called thromboxane $A_2$ receptor antagonists, thromboxane $A_2$ antagonists, thromboxane $A_2$/prostaglandin endoperoxide antagonists, TP-receptor antagonists, or thromboxane antagonists.

The compounds of the invention are also thromboxane synthetase inhibitors and thus are useful as inhibitors of thromboxane production.

The compounds of this invention are useful as inhibitors of platelet function, i.e., for the prevention and treatment of thrombotic vascular occlusive disorders, whether complete or partial, for example, arterial thrombosis, including that of the coronary, cerebral, ophthalmic, hepatic, mesenteric, renal, peripheral arteries or vascular or organ grafts, unstable angina, transient ischemic attacks, or intermittent claudication. They may be useful to prevent thrombosis following vascular injury produced in the course of diagnostic or therapeutic procedures such as endarterectomy or angiography. The compounds may be useful in the treatment or prevention of disorders characterized by platelet consumption and/or activation, including, platelet activation, dysfunction, and/or loss during extracorporeal circulation, the use of radiographic contrast agents, thrombotic thrombocytopenia purpura, disseminated intravascular coagulation, purpura fulminans, hemolytic transfusion reaction, or hemolytic uremic syndrome, systemic lupus, cyclosporine-induced renal toxicity, pulmonary hypertension, side effects from dialysis, or abdominal aortic aneurism repair. The compounds may be used in the treatment of venous thrombosis or embolism, including pulmonary embolism, deep venous thrombosis, hepatic vein thrombosis, and renal vein thrombosis.

The compounds of this invention are useful as inhibitors of arterial or venous vasoconstriction. Accordingly, they may be useful to prevent vasoconstriction associated with unstable angina, chronic stable angina, and variant, or Prinzmetal's angina, Raynaud's syndrome, migraine headache, vasospasm of the coronary, cerebral, ophthalmic, hepatic, mesenteric, renal, peripheral arteries or vascular grafts, vascular injury such as that associated with surgery or trauma. Hypertension of pregnancy, the hepato-renal syndrome, and pulmonary hypertension are additional examples of vasoconstrictive disorders treatable by the compounds of this invention.

The compounds of this invention are useful as inhibitors of bronchoconstriction, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues, including, myocardium, skin, brain, bowel, or kidney, alone or in combination with other agents intended to restore blood flow. For example, these compounds may be useful for improving postischemic myocardial function and decreasing myocardial infarct size. Ischemia caused by reduced blood flow during diagnostic or therapeutic procedures may benefit by treatment with these compounds; for example, they reduce the myocardial stunning observed after bypass surgery. In addition, they may be useful for reducing the tissue injury caused by a stroke.

The compounds of this invention may be useful in the prevention or treatment of other conditions including burns, diabetic retinopathy, tumor metastases and tardive dyskinesia. The compounds may be useful in potentiating diuretic-induced diuresis.

In addition, the thromboxane receptor antagonists of the invention may be used with a thrombolytic agent such as t-PA, streptokinase, urokinase, prourokinase or anisoylated plasminogen-streptokinase activator complex (APSAC) within 6 hours of a myocardial infarction. In such case, the thrombolytic agent may be used in amounts conventionally employed, for example, as disclosed in the Physicians' Desk Reference, for reducing post-ischemic myocardial injury.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight of compound I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

Preferred Embodiments

The following examples represent preferred embodiments of the present invention. Unless otherwise indicated, all temperatures are expressed in degrees Celsius.

EXAMPLE 1

(–)-cis-2-[[2-[4-[[(4-Cyclohexylbutyl)amino]-carbonyl]-2-oxazolyl]cyclopentyl]methyl]benzene-propanoic acid A. Tetrahydro-1H-cyclopenta[c]furan-1,3(3aH) -dione trans-Cyclopentane-1,2-dicarboxylic acid was heated by a Bunsen burner and water was distilled off. The atmosphere was switched to house low vacuum and the solid anhydride A was distilled off. The collected solid was combined with 200 mL of benzene and the insoluble anhydride A was filtered off. This solid was dried under pump vacuum to give 8.60 g (81%) of anhydride A.

$^{13}$C NMR of anhydride A (L514-40-20, 67.5 MHz, CDCl$_3$) δ: 174.5, 45.6, 31.6, 25.2.

B. Hexahydro-1H-cyclopenta[c]furan-1-one

To a stirred mixture of anhydride A (10.1 g, 72.1 mmol) in 100 mL of dry tetrahydrofuran under argon at 0° C. was added sodium borohydride (4.11 g, 108 mmol). The mixture was stirred at 0° C. for 7 hours and poured into 150 mL of an ice-water mixture. The mixture was neutralized by the addition of 6N hydrochloric acid solution and then concentrated in vacuo to remove tetrahydrofuran. The residue was acidified to pH 1 by the addition of 1 N hydrochloric acid solution and extracted with ether (3×150 mL) and dichloromethane (2×150 mL). The combined organic extracts were dried (magnesium sulfate), filtered and concentrated in vacuo. The residue was dissolved in 400 mL of ether and washed with saturated sodium bicarbonate solution (1×60 mL) and brine (1×100 mL). The ether layer was dried (magnesium sulfate), filtered and concentrated in vacuo to give 5.63 g (62%) of lactone B.

$^{13}$C NMR of lactone B (67.5 MHz, CDCl$_3$) δ: 181.1, 73.5, 44.4, 38.8, 33.6, 30.6, 25.4.

C. Hexahydro-1H-cyclopenta[c]furan-1-ol

To a stirred mixture of lactone B (5.62 g, 44.6 mmol) under argon at –78° C. was added dropwise a 1.5M diisobutylaluminum hydride-toluene solution (59.5 mL, 89.2 mmol). The rate of addition was monitored so that the pot temperature did not exceed –70° C. The addition took about 20 min. The mixture was stirred at –78° C. for 5 hours and quenched slowly with 100 mL of acetone. To this mixture was then added very carefully 70 g of a mixture of 10:9 silica gel-water. The resulting mixture was diluted with 200 mL of acetone and the cooling bath was removed. The mixture was stirred for 30 minutes and the solid was filtered off. The solid was rinsed with acetone (4×50 mL). The filtrate was concentrated in vacuo and chromatographed on 240 g of Merck silica gel 60 using 4% methanol/dichloromethane as eluant to give 3.95 g (69%) of lactol C.

TLC: silica gel, 4% methanol/dichloromethane
R$_f$ 0.34, cerium disulfate.
$^{13}$CNMR of lactol C (67.5 MHz, CDCl$_3$) δ: 104.7, 73.7, 51.3, 42.3, 33.9, 30.9, 26.5.

D. cis-α-[2-[3-[[Dimethyl(1,1,2 -trimethylpropyl)silyl]oxy]propyl]phenyl]]1,2 -cyclo-pentanedimethanol To a stirred mixture of magnesium turnings (4.50 g, 185 mmol) and one crystal of iodine in 50 mL of dry tetrahydrofuran under argon at 40° C. was added 10% of a solution of 1-bromo-2-[3-[[dimethyl-(1,1,2-trimethylpropyl)silyl]oxy]propyl]benzene (16.5 g, 46.3 mmol) in 20 mL of dry tetrahydrofuran. The iodine color dispatched and the remaining 90% of the bromide-tetrahydrofuran solution was added over 25 min. The mixture was stirred at 40° C. for one hour and cooled to 0° C. To a stirred mixture of lactol C (3.95 g, 30.9 mmol) in 40 mL of dry tetrahydrofuran under argon at 0° C. was added dropwise 2M solution of ethylmagnesium bromide in tetrahydrofuran (13.9 mL, 27.8 mmol) over 10 minutes. This mixture was stirred under argon at 0° C. for 20 minutes, at which time the above (0° C.) Grignard solution was added over 20 min. The reaction mixture was stirred at room temperature for 21 hours and quenched slowly at 0° C. with 10 mL of saturated ammonium chloride solution. The mixture was concentrated in vacuo to remove tetrahydrofuran. The residue was partitioned between 300 mL of saturated ammonium chloride solution and ethyl acetate (4×30 mL). The organic extracts were dried (magnesium sulfate), filtered and concentrated in vacuo. This material was chromatographed on 240 g of Merck silica gel 60 using 2% methanol/dichloromethane as eluant to give 12 g (96%) of diol D.

TLC: silica gel, 4% methanol/dichloromethane
R$_f$ 0.46, cerium disulfate
$^{13}$C NMR of diol D (67.5 MHz, CDCl$_3$) δ: 141.3, 139.6, 129.3, 127.3, 126.8, 126.3, 63.7, 62.4, 49.2, 43.5, 34.6, 34.1, 29.0, 28.6, 25.1, 23.5, 20.3, 18.5, –3.4.

E. cis-2-[[2-[3-[[Dimethyl(1,1,2 -trimethyl-propyl)silyl]oxy]propyl]phenyl]methyl]-cyclopentanemethanol To a stirred mixture of diol D (12 g, 29.6 mmol) in 120 mL of acetic acid under argon was added 20% palladium hydroxide on carbon (2.4 g, 20% based on the weight of diol D). The atmosphere was switched to hydrogen by several vacuum-fill cycles. The mixture was stirred at room temperature for 18 hours and the catalyst was filtered off through a 4 mM polycarbonate film. The catalyst was rinsed with acetic acid (3×150 mL). The fitrate was concentrated in vacuo and chromatographed on 200 g of Merck silica gel 60 using 1% methanol/dichloromethane as eluant to give 8.85 g (77%) of alcohol E.

TLC: silica gel, 2% methanol/dichloromethane
R$_f$ 0.64, cerium disulfate
$^{13}$C NMR of alcohol E (67.5 MHz, CDCl$_3$) δ: 140.2, 139.6, 129.5, 129.1, 125.8, 125.6, 63.5, 62.5, 45.1, 42.3, 34.2, 31.9, 30.5, 29.0, 27.7, 25.2, 22.7, 20.4, 18.6, –3.4. F. cis-2-[[2-(Hydroxymethyl)cyclopentyl]-methyl]benzenepropanoic acid, methyl ester To a stirred mixture of alcohol E (8.85 g, 22.8 mmol) in pyridine (5.51 mL, 68.3 mmol) under argon at 0° C. was added acetic anhydride (3.22 mL, 34.1 mmol). The mixture was stirred at room temperature for 17 hours and diluted with 400 mL of ethyl acetate. The resulting solution was washed with 1N hydrochloric acid solution (3×100 mL) and saturated sodium bicarbonate solution (3×100 mL). The organic layer was dried (magnesium sulfate), filtered and concentrated in vacuo. To a stirred mixture of this acetate in 200 mL of acetone at 0° C. was added manganese sulfate-treated Jones reagent (1 mg manganese sulfate/mL of Jones Reagent) until an orange-red color persisted. The mixture was stirred at room temperature for 2 hours and quenched with isopropyl alcohol. The mixture was concentrated in vacuo and partitioned between 200 mL of 3M sodium metabisulfite solution and ethyl acetate (3×300 mL). The ethyl acetate extracts were dried (magnesium sulfate), filtered and concentrated in vacuo. This crude acid was dissolved in 200 mL of methanol and treated with acetyl chloride (3 mL). The mixture was stirred at room temperature for 16 hours and concentrated in vacuo. The residue was diluted with 400 mL of ethyl acetate and washed once with 150 mL of saturated aqueous sodium bicarbonate solution. The organic layer was dried (magnesium sulfate), filtered and concentrated in vacuo. Purification was effected by flash chromatography on 180 g of Merck silica gel 60 using 1:1 hexane-ether as eluant to give 4.41 g (70%) of ester F.
TLC: silica gel, 2:1 ether-hexane
$R_f$ 0.54, cerium disulfate
$^{13}C$ NMR of ester F (67.5 MHz, CDCl$_3$) δ: 173.5, 139.6, 138.3, 129.7, 128.7, 126.1, 125.9, 63.2, 51.6, 45.0, 42.1, 35.2, 31.6, 30.2, 27.5, 27.4, 22.5.

G. cis-2-[[2-(Carboxymethyl)cyclopentyl]-methyl]benzenepropanoic acid, methyl ester To a stirred mixture of ester F (2.10 g, 7.66 mmol) in 70 mL of acetone under argon at 0° C. was added manganese sulfate-treated Jones reagent (6 mL) until an orange red color persisted. The mixture was stirred at 0° C. for 15 minutes and at room temperature for 1 hour The mixture was quenched with isopropyl alcohol and partitioned between 100 mL of 3M sodium metasulfite solution and ethyl acetate (4×120 mL). The ethyl acetate extracts were dried (magnesium sulfate), filtered and concentrated in vacuo. This material was chromatographed on 60 g of Merck silica gel 60 using 2% methanol/dichloromethane with 0.25% acetic acid as eluant to give 1.37 g (62%) of acid G.
TLC: silica gel, 4% methanol/dichloromethane with 0.25% acetic acid
$R_f$ 0.48, cerium disulfate.
$^{13}C$ NMR of acid G (67.5 MHz, CDCl$_3$) δ: 181.2, 173.4, 138.9, 138.4, 130.0, 128.8, 126.4, 126.3, 51.6, 47.8, 44.4, 35.2, 33.2, 30.4, 27.9, 27.5, 23.2.

H. N-(4-Cyclohexylbutyl)-2-aminoacetamide, monohydrochloride

To a stirred solution of 1.14 g (6.5 mmol) of t-butyloxycarbonyl-glycine in 10 mL of tetrahydrofuran at 0° C. was added 1.05 g (6.5 mmol) of carbonyldiimidazole. The ice bath was removed and the reaction mixture was allowed to warm to room temperature over a period of 90 minutes. To this mixture was added 1.18 g (6.14 mmol) of 4-cyclohexylbutylamine hydrochloride followed by 1.0 mL of triethylamine (7.2 mmol). An exotherm was noted which was accompanied by the formation of a thick precipitate. An additional 5.0 mL of tetrahydrofuran was added and the reaction mixture was allowed to stir at room temperature for 18.5 hours. The reaction mixture was diluted with 30 mL of water, acidified to pH 4 with 1N hydrochloric acid, and extracted with two 30 mL portions of ethyl acetate. The combined ethyl acetate extracts were washed with 30 mL of 0.1N sodium hydroxide, dried (magnesium sulfate), filtered and concentrated in vacuo to afford 1.97 g of crude amide. To a flask containing the above amide was added 20 mL of pre-chilled (0° C.) trifluoroacetic acid. After stirring at 0° C. for 30 minutes, the reaction mixture was concentrated in vacuo at 0° C. The residue was reconcentrated from 25 mL of toluene. The residue was dissolved in 25 mL of methanol and treated with approximately 1 mL of concentrated hydrochloric acid. This was concentrated in vacuo, redissolved in methanol, and reconcentrated to afford a viscous oil. This was triturated in 50 mL of ether to afford 1.38 g of the title compound (84% overall).

I. (cis,S)-2-[[2-[[[2-[(4-Cyclohexylbutyl)-amino]-1-(hydroxymethyl)-2-oxoethyl]amino]-carbonyl]cyclopentyl]methyl]benzenepropanoic acid, methyl ester, isomer A J. (cis,S)-2-[[2-[[[2-[(4-Cyclohexylbutyl)-amino]-1-(hydroxymethyl)-2-oxoethyl]amino]-carbonyl]cyclopentyl]methyl]benzenepropanoic acid, methyl ester, isomer B To a stirred mixture of acid G (800 mg, 1.99 mmol), amine H (554 mg, 1.99 mmol) and 1-hydroxybenzotriazole monohydrate (298 mg, 1.99 mmol) in 20 mL of dimethylformamide under argon was added sequentially triethylamine (0.83 mL, 5.96 mmol) and 1-(3-dimethylaminopropyl)-ethyl carbodiimide hydrochloride salt (381 mg, 1.99 mmol). The mixture was stirred at room temperature for 16 hours and concentrated in vacuo. The residue was partitioned between 350 mL of ethyl acetate and 0.2N sodium hydroxide solution (3×40 mL), 1N hydrochloric acid solution (2×40 mL), saturated sodium bicarbonate solution (1×40 mL) and brine (1×100 mL). The ethyl acetate layer was dried (magnesium sulfate), filtered and concentrated in vacuo. This material was chromatographed on 60 g of Merck silica gel 60 using 2% methanol/dichloromethane as eluant to give 240 mg of cis-isomer I and a mixture of cis-isomers I and J. This mixture was chromatographed on 60 g of Merck silica gel 60 using 2% methanol/dichloromethane as eluant to give 120 mg of cis-isomer I and 410 mg of a mixture of cis-isomers I and J. This mixture was again chromatographed on 40 g of Merck silica gel 60 using 2% methanol/dichloromethane as eluant to give 360 mg (29%) of cis-isomer J. The final yield of cis-isomer I was 360 mg (29%).
TLC: silica gel 4% methanol/dichloromethane
$R_f$ isomer I, 0.46; isomer J, 0.44, cerium disulfate
$^{13}C$ NMR of isomer J (67.5 MHz, CDCl$_3$) δ: 175.8, 173.5, 170.8, 138.9, 138.3, 129.8, 128.7, 126.3, 62.9, 53.8, 51.6, 48.9, 44.5, 39.5, 37.4, 36.9, 35.1, 33.2, 30.8, 29.7, 28.3, 27.4, 26.6, 26.3, 24.1, 23.6.

K. cis-2-[[2-[4-[[(4-Cyclohexylbutyl)amino]-carbonyl]-4,5-dihydro-2-oxazolyl]cyclo-pentyl]methyl]benzenepropanoic acid, isomer A, methyl ester To a stirred mixture of alcohol I (360 mg, 0.57 mmol) in 4 mL of dry dichloromethane was added sequentially triethylamine (0.16 mL, 1.15 mmol) and mesyl chloride (0.053 mL, 0.69 mmol). The mixture was stirred at room temperature for one hour and concentrated in vacuo. To this crude mesylate in 10 mL of acetone was added potassium carbonate (0.79 g, 5.70 mmol). The mixture was refluxed for 5 hours and cooled to room temperature. The solid was filtered off and rinsed with acetone (3×40 mL). The filtrate was concentrated in vacuo and chromatographed on 40 g of Merck silica gel 60 using 2% methanol/dichloromethane as eluant to give 330 mg (94%) of oxazoline K.

TLC: silica gel, 4% methanol/dichloromethane $R_f$ 0.44, cerium disulfate $^{13}C$ NMR of oxazoline K (67.5 MHz, CDCl$_3$) δ: 173.1, 172.1, 171.7, 138.8, 138.3, 129.7, 128.7, 126.3, 69.9, 68.4, 51.6, 43.9, 42.1, 39.1, 37.4, 36.9, 35.1, 33.3, 33.1, 30.7, 29.7, 28.5, 27.6, 26.6, 26.3, 24.0, 23.2.

L. cis-2-[[2-[4-[[(4Cyclohexylbutyl)amino]-carbonyl]-2-oxazolyl]cyclopentyl]methyl]-benzenepropanoic acid, isomer A, methyl ester To a stirred mixture of cupric bromide (254 mg, 1.14 mmol) in 1.5 mL of ethyl acetate under argon was added 1,8-diazabicyclo[5.4.0]undec-7-ene (0.34 mL, 2.28 mmol). The mixture was stirred at room temperature for 30 minutes, at which time a solution of oxazoline K (330 mg, 0.54 mmol) in 1.5 mL of trichloromethane was added. The reaction mixture was stirred at room temperature for 19 hours and another batch of cupric bromide (250 mg, 1.14 mmol) and 1,8-diazabicyclo[5.4.0]undec-7-ene (0.17 mL, 1.14 mmol) was added. The mixture was stirred for 7 hours, at which time cupric bromide (130 mg, 0.57 mmol) and 1,8-diazabicyclo[5.4.0)-undec-7-ene (0.09 mL, 0.57 mmol) were added. The mixture was stirred for 18 hours and cupric bromide (130 mg, 0.57 mmol) and 1,8-diazabicyclo[5.4.0]-undec-7-ene (0.15 mL, 1.00 mmol) were again added. The mixture was stirred at room temperature for another 24 hours and poured into a mixture of 70 mL of ethyl acetate and 50 mL of 1:1 concentrated ammonium hydroxide solution-saturated ammonium chloride solution. The resulting mixture was extracted with ethyl acetate (3×60 mL). The ethyl acetate extracts were dried (magnesium sulfate), filtered and concentrated in vacuo. This material was chromatographed on 40 g of Merck silica gel 60 using 3:2 ether-hexane as eluant to give 230 mg (70%) of oxazole L.

TLC: silica gel, ether $R_f$ 0.70, cerium disulfate $^{13}C$ NMR of oxazole L (67.5 MHz, CDCl$_3$) δ: 173.2, 166.4, 160.7, 140.3, 138.6, 138.2, 136.0, 129.7, 128.7, 126.3, 126.2, 51.6, 45.1, 42.2, 39.1, 37.5, 37.1, 35.0, 33.3, 30.5, 30.0, 29.1, 27.5, 26.7, 26.4, 24.2, 23.1.

M. cis-2-[[2-[4-[[(4-Cyclohexylbutyl)amino]-carbonyl]-2-oxazolyl]cyclopentyl]methyl]-benzenepropanoic acid, isomer A To stirred mixture of oxazole L (220 mg, 0.38 mmol) in 8 mL of freshly distilled tetrahydrofuran and 2 mL of water was added lithium hydroxide monohydrate (45.6 mg, 1.08 mmol). The mixture was stirred at room temperature for 5 hours and stored in the freezer overnight. The mixture was stirred at room temperature for another 3 hours and acidified to pH 2 by the addition of 1N hydrochloric acid solution. The mixture was then diluted with 10 mL of water, saturated with sodium chloride and extracted with ethyl acetate (4×25 mL). The ethyl acetate extracts were dried (magnesium sulfate), filtered and concentrated in vacuo. This material was crystallized in 20 mL of 4:1 hexane-ethyl acetate at −5° C. to give 180 mg (84%) of Example 1 as a solid.

Melting point 104°–106° C.

TLC: silica gel, ether $R_f$ 0.15, cerium disulfate $^{13}C$ NMR of Example 1 (67.5 MHz, CDCl$_3$) δ: 176.8, 166.6, 161.0, 140.9, 138.6, 138.2, 135.7, 129.7, 128.8, 126.3, 126.2, 45.1, 42.2, 39.2, 37.5, 37.0, 35.0, 33.3, 30.5, 29.8, 29.1, 27.3, 26.6, 26.3, 24.2, 23.2.

EXAMPLE 2

(+)-cis-2-[[2-[4-[[(4-Cyclohexylbutyl)amino]carbonyl]-2-oxazolyl]cyclopentyl]methyl]benzenepropanoic acid A. (+)cis-2-[[2-[4-[[(4-Cyclohexylbutyl)amino]-carbonyl]-4,5-dihydro-2-oxazolyl]cyclo-pentyl]methyl]benzenepropanoic acid, methyl ester To a stirred mixture of isomer J from Example 1 (350 mg, 0.57 mmol) in 4 mL of dry dichloromethane was added sequentially triethylamine (0.16 mL, 1.15 mmol) and mesyl chloride (0.053 mL, 0.69 mmol). The mixture was stirred at room temperature for one hour and concentrated in vacuo. To this crude mesylate in 10 mL of acetone was added potassium carbonate (0.79 g, 5.70 mmol). The mixture was refluxed for 5 hours and cooled to room temperature. The solid was filtered off and rinsed with acetone (3×30 mL). The filtrate was concentrated in vacuo and chromatographed on 34 g of Merck silica gel 60 using 2% methanol/dichloromethane as eluant to give 340 mg (97%) of oxazoline A.

TLC: silica gel, 4% methanol/dichloromethane $R_f$ 0.44, cerium disulfate $^{13}C$ NMR of oxazoline A (67.5 MHz, CDCl$_3$) δ: 173.1, 172.1, 171.7, 138.7, 138.3, 129.9, 128.8, 126.4, 126.2, 70.0, 68.4, 51.5, 44.1, 42.3, 39.1, 37.4, 36.9, 35.1, 33.2, 33.1, 30.3, 29.8, 28.2, 27.4, 26.6, 26.3, 24.0, 23.1.

B. cis-2-[[2-[4-[[(4-Cyclohexylbutyl)amino]-carbonyl]-2-oxazolyl]cyclopentyl]methyl]-benzenepropanoic acid, isomer B, methyl ester To a stirred mixture of cupric bromide (254 mg, 1.14 mmol) in 1.5 mL of ethyl acetate under argon was added 1,8-diazabicyclo[5.4.0]undec-7-ene (0.34 mL, 2.28 mmol). The mixture was stirred at room temperature for 30 minutes at which time a solution of oxazoline A (330 mg, 0.54 mmol) in 1.5 mL of trichloromethane was added. The reaction mixture was stirred at room temperature for 17 hours and another batch of cupric bromide (130 mg, 0.57 mmol) and 1,8-diazabicyclo[5.4.0]undec-7-ene (0.17 mL, 1.14 mmol) was added. The mixture was stirred for 8 hours at which time cupric bromide (254 mg, 1.14 mmol) and 1,8-diazabicyclo[5.4.0]-undec-7-ene (0.17 mL, 1.14 mmol) were added. The mixture was stirred for 18 hours and poured into a mixture of 70 mL of ethyl acetate and 50 mL of 1:1 concentrated ammonium hydroxide solution-saturated ammonium chloride solution. The resulting mixture was extracted with ethyl acetate (3×60 mL). The ethyl acetate extracts were dried (magnesium sulfate), filtered and concentrated in vacuo. This was chromatographed on 35 g of Merck silica gel 60 using 3:2 ether-hexane as eluant to give 240 mg (73%) of oxazole B.

TLC: silica gel, ether $R_f$ 0.70, cerium disulfate $^{13}C$ NMR of oxazole B (67.5 MHz, CDCl$_3$) δ: 173.2, 160.7, 140.3, 138.6, 129.7, 128.7, 126.3, 126.2, 51.6, 45.1, 42.2, 39.1, 37.5, 37.1, 35.0, 33.3, 30.5, 30.0, 29.1, 27.5, 26.7, 26.4, 24.2.

C. (+)-cis-2-[[2-[4-[[(4-Cyclohexylbutyl)amino]-carbonyl]-2-oxazolyl]cyclopentyl]methyl]-benzenepropanoic acid To stirred mixture of oxazole B (230 mg, 0.38 mmol) in 8 mL of freshly distilled tetrahydrofuran and 2 mL of water was added lithium hydroxide monohydrate (47.7 mg, 1.14 mmol). The mixture was stirred at room temperature for 5 hours and stored in the freezer overnight. The mixture was stirred at room temperature for another 3 hours and acidified to pH 2 by the addition of 1N hydrochloric acid solution. The mixture was then diluted with 10 mL of water, saturated with sodium chloride and extracted with ethyl acetate (4×25 mL). The ethyl acetate extracts were dried (magnesium sulfate), filtered and concentrated in vacuo. This material was crystallized in 20 mL of 4:1 hexane-ethyl acetate at −5° C. to give 150 mg (67%) of Example 2 as a solid.

Melting point 104–106° C.
TLC: silica gel, ether
$R_f$ 0.15, cerium disulfate
$^{13}$C NMR of Example 2 (67.5 MHz, CDCl$_3$) δ: 176.8, 166.6, 161.1, 141.0, 138.6, 138.2, 135.7, 129.7, 128.8, 126.4, 126.3, 45.2, 42.2, 39.2, 37.5, 37.1, 35.0, 33.3, 30.5, 29.8, 29.1, 27.4, 26.7, 26.3, 24.2, 23.2.

EXAMPLE 3

(–)-trans-2-[[2-[4-[[[2-(4-Chlorophenyl)ethyl]amino-carbonyl]-2-oxazolyl]cyclopentyl]methyl] benzenepropanoic acid A. trans-Cyclopentane-1,2-dicarboxylic acid, dimethyl ester Acetyl chloride (3 mL) was added dropwise to a stirred solution of trans-cyclopentane dicarboxylic acid (5 g, 31.65 mmol) in anhydrous methanol (30 mL) at 0–5° C. The homogeneous solution was allowed to warm slowly to room temperature and stirred a total of six hours. The mixture was concentrated under reduced pressure and the residual oil was dissolved in ethyl acetate (150 mL), washed with saturated sodium bicarbonate solution and water, dried (magnesium sulfate), and taken to dryness in vacuo to give diester A (5.35 g, 97%) as a colorless oil.
TLC: $R_f$=0.86, silica gel, ethyl acetate:hexane (1:1), cerium disulfate.

B. trans-Cyclopentane-1,2-dimethanol

A solution of diester A (5.35 g, 28.76 mmol) in distilled tetrahydrofuran (20 mL) was added dropwise to a stirred suspension of lithium aluminum hydride (2.28 g, 60 mmol) in dry tetrahydrofuran (150 mL) at 0–50° C. After addition was complete, the cooling bath was removed and the suspension was stirred at room temperature for 7 hours. The mixture was then cooled and excess hydride was destroyed by careful addition of saturated sodium sulfate solution. Addition of the sodium sulfate solution was continued until all salts were precipitated as white granular solids. The mixture was diluted with ethyl acetate and anhydrous magnesium sulfate was added. The solids were removed by filtration through a pad of magnesium sulfate. The pad was washed with more ethyl acetate, and the filtrate was freed of solvent in vacuo to give dimethanol B (3.57 g, 95%) as a colorless oil.
TLC: $R_f$=0.25, silica gel, ethyl acetate:hexane (1:1), cerium disulfate.

C. trans-2-[[[(1,1-Dimethylethyl)diphenyl -silyl]oxy] methyl]cyclopentanemethanol A solution of dimethanol B (2.43 g, 18.7 mmol) in distilled tetrahydrofuran (10 mL) was added dropwise to a stirred suspension of sodium hydride (494 mg, 20.57 mmol, 1.1 eq) in dry tetrahydrofuran at 0–50° C. The cooling bath was removed and the mixture was stirred at room temperature 40 minutes. After recooling to 0–5° C., tert-butylchlorodiphenylsilane (5.66 g, 20.57 mmol) was added. The mixture was stirred cold for one hour and was then quenched by adding water (50 mL). Ethyl acetate (100 mL) was added and the layers were separated. The organic layer was washed with brine, dried (magnesium sulfate), and freed of solvent in vacuo. The residue was chromatographed on silica gel (150 g, Merck), eluting with 5–10% ethyl acetate in hexane to give alcohol C (4.75 g, 69%) as a colorless oil.
TLC: $R_f$=0.56, silica gel, 25% ethyl acetate in hexane, UV and cerium disulfate.

D. trans-2-[[[(1,1-Dimethylethyl)diphenyl-silyl]oxy] methyl]cyclopentanealdehyde Alcohol C (6.96 g, 19 mmol) was dissolved in dichloromethane (30 mL) and added dropwise to a stirred mixture of pyridinium chlorochromate (8.19 g, 38 mmol, 2 eq), Celite® (8.2 g) and anhydrous sodium acetate (47.5 mmol, 2.5 eq) in dichloromethane (500 mL). One hour after addition was complete, diethyl ether (500 mL) was added and the mixture was filtered through a Celite® pad. The pad was washed with more ether and the filtrate was freed of solvent in vacuo. The remaining material was purified on a silica gel column (300 g, Merck), eluting with 5% ethyl acetate in hexane to give aldehyde D (4.96 g, 71%).
TLC: $R_f$=0.46 & 0.51, silica gel, 10% ethyl acetate in hexane, UV and cerium disulfate.

E. trans-2-[[[(1,1-Dimethylethyl)diphenyl-silyl]oxy] methyl]-α-[2-[3-[[dimethyl(1,1,2-trimethylpropyl)silyl] oxy]propyl]phenyl]-cyclopentanemethanol A suspension of magnesium turnings (1.19 g 48 mmol, 3,6 eq) and catalytic iodine in anhydrous tetrahydrofuran (15 mL) was heated under reflux. A few drops of [3-(2-bromophenyl)]-propanol,dimethylthexylsilyl ether was added to initiate the formation of Grignard reagent. Once Grignard reagent. Once the iodine color was discharged, additional bromide (a total of 5.57 g, 16.9 mmol, 1.25 eq) was added portionwise. The mixture was heated under reflux for 60 minutes, cooled to 0° C. in an ice-water bath and was then added via a cannula to a solution of aldehyde D (4.96 g, 13.55 mmol) at –78° C. The mixture was stirred at –78° C. for 60 minutes and quenched with saturated ammonium chloride solution. Ethyl acetate and water were added and the layers were separated. The aqueous layer was reextracted with ethyl acetate. The combined organic layers were dried (magnesium sulfate), filtered and concentrated. The residue was chromatographed on a silica gel column (260 g, Merck), eluting with 3–5% ethyl acetate in hexane to give diprotected triol E as two alcohol isomers (total 5.21 g, 60%), which were characterized by NMR.
TLC: $R_f$=0.51 & 0.63, silica gel, 10% ethyl acetate in hexane, UV and cerium disulfate.

F. trans-2-[[[(1,1-Dimethylethyl)diphenyl-silyl]oxy] methyl]-α-[2-[3-[[dimethyl(1,1,2-trimethylpropyl)silyl] oxy]propyl]phenyl]-cyclopentanemethanol, acetate ester The alcohol isomers E (5.19 g, 8.07 mmol) were dissolved in dichloromethane (70 mL) and pyridine (7 mL). Acetic anhydride (3.5 mL) was added and the mixture was stirred at room temperature for 18 hours. TLC indicated the reaction was proceeding very slowly, and dimethylaminopyridine (183 mg, 1.5 mmol) was added. The reaction appeared to be complete 2 hours after the addition of dimethylaminopyridine. The mixture was diluted with diethyl ether (400 mL) and the solution was washed with water (125 mL) saturated cupric sulfate solution (3×100 mL) and water (125 mL). The solution was dried (magnesium sulfate), filtered and freed of solvent in vacuo. Toluene was added and removed in vacuo (3x) to give compound F as a mixture of acetates (4.5 g, 81%), which was characterized by NMR spectra.
TLC: $R_f$=0.65, silica gel, 10% ethyl acetate in hexane, UV and cerium disulfate.

G. trans-2-[(Acetyloxy)[2-[[[(1,1-dimethyl -ethyl) diphenylsilyl]oxy]methyl]cyclo-pentyl]methyl] benzenepropanoic acid, methyl ester Acetate F (4.5 g, 6.55 mmol) was dissolved in acetone (50 mL), cooled to 0°–50° C. and treated dropwise with Jones reagent (chromium trioxide/sulfuric acid, 2.67N, 6 mL). The mixture was stirred cold one hour, then quenched by adding 2-propanol (6 mL). Ethyl acetate (150 mL) and water (75 mL) were added and the layers were separated. The aqueous layer was reextracted with ethyl acetate. The combined organic layers were dried (magnesium sulfate), filtered, and freed of solvent in vacuo, leaving the acid as a pale yellow oil. This oil was dissolved in ether, cooled to 0°–5° C., and treated with an excess of a solution of diazomethane in ether. After a few minutes, the solvent was removed in vacuo and the remaining material was purified by chromatography on silica gel (260 g, Merck) eluting with 5% ethyl acetate in hexane to give the methyl ester G (2.91 g, 78%) as an oil, which was characterized by NMR spectra.

TLC: $R_f$=0.44, silica gel, 15% ethyl acetate in hexane, UV and cerium disulfate.

H. trans-2-[(Acetyloxy)[2-[(acetyloxy)methyl]-cyclopentyl]methyl]benzenepropanoic acid, methyl ester The silyl protected compound G (2.70 g, 4.72 mmol) was dissolved in distilled tetrahydrofuran (50 mL) in an argon atmosphere and treated with a 1M solution of tetrabutylammonium fluoride in tetrahydrofuran (7 mL). After stirring at room temperature for 2 hours, additional tetrabutylammonium fluoride (3 mL) was added, and the mixture was stirred at room temperature an additional 3.5 hours. Water (200 mL) and ethyl acetate (200 mL) were then added, and the layers were separated. The aqueous layer was reextracted with ethyl acetate (150 mL). The combined organic layers were dried (magnesium sulfate) and freed of solvent in vacuo. The residue was dissolved in dichloromethane (60 mL) and treated with dry pyridine (6 mL), acetic anhydride (3 mL), and 4-dimethylaminopyridine (60 mg, 0.1 eq). The mixture was stirred at room temperature five hours and was then diluted with ether (250 mL). The ether solution was washed with water (100 mL), saturated aqueous cupric sulfate, and water (100 mL), dried (magnesium sulfate) and freed of solvent in vacuo. The product was purified by chromatography on silica gel (250 g, Merck), eluting with 15–25% ethyl acetate in hexane to give the diacetate H (1.299 g, 73%) as a colorless oil which was characterized by NMR spectra. TLC: $R_f$=0.46, silica gel, 30% ethyl acetate in hexane, UV and cerium disulfate.

I. trans-2-[[2-[(Acetyloxy)methyl]cyclopentyl]-methyl]benzenepropanoic acid, methyl ester The diacetate H (1.299 g, 3.45 mmol) was dissolved in glacial acetic acid and treated with 20% palladium hydroxide on carbon (260 mg, 20% by weight). The reaction flask was equipped with a hydrogen-filled balloon via a three-way stopcock. Air inside the flask was removed under reduced pressure, and it was filled with hydrogen from the balloon. This operation was repeated four times. After stirring at room temperature for six hours, additional palladium hydroxide on carbon (210 mg) was added, the system was recharged with hydrogen, and the mixture was left stirring at room temperature overnight. The catalyst was removed by filtration through a polycarbonate membrane, the pad was washed several times with acetic acid and the filtrate was taken to dryness in vacuo. Residual acetic acid was removed by adding toluene and removing in vacuo. The residue was purified by chromatography on silica gel (60 g, Merck) eluting with 10% ethyl acetate in hexane to give monoacetate I (10, 710 mg, 65%). Also obtained from the chromatography was starting material H (342 mg, 26%). This starting material was recycled through the hydrogenation reaction, allowing it to proceed for 3 days with addition of fresh catalyst each day, to give an additional sample of monoacetate I (179 mg, total yield in two passes, 81%). The material was characterized by NMR.

TLC: $R_f$=0.62 silica gel, 30% ethyl acetate in hexane, UV and cerium disulfate.

J. trans-2-[[2-[(Hydroxy)methyl]cyclopentyl]-methyl]benzenepropanoic acid, methyl ester The monoacetate I (918 mg, 2.88 mmol) was dissolved in methanol (14 mL) in an argon atmosphere and cooled to 0° C. Powdered potassium carbonate (276 mg, 2 mmol) was added and the stirred mixture was allowed to warm slowly to room temperature. After 4.5 hours, water (40 mL) and ethyl ether (125 mL) were added. The layers were separated. The organic layer was dried (magnesium sulfate), filtered and freed of solvent in vacuo. The remaining material was purified by chromatography on silica gel (40 g, Merck), eluting with 15–25% ethyl acetate in hexane to give the alcohol J (755 mg, 95%) as an oil, which was characterized by NMR spectra.

TLC: $R_f$=0.35 silica gel, 30% ethyl acetate in hexane, UV and cerium disulfate.

K. trans-2-[[2-(Carboxy)cyclopentyl]methyl]-benzenepropanoic acid, methyl ester

A 2.67M solution of Jones reagent (4.4 mL) was added dropwise to a stirred solution of alcohol J (755 mg, 2.73 mmol) in acetone (45 mL) at 0°–5° C. The mixture was stirred at 0°–5° C. for 1 hour and then at room temperature for 2.5 hours. Excess Jones reagent was destroyed by addition of isopropanol (4 mL). The mixture was diluted with ethyl acetate (150 mL) and water (75 mL). The ethyl acetate layer was separated and the aqueous layer was reextracted with ethyl acetate (60 mL). The ethyl acetate extracts were combined, dried (magnesium sulfate), filtered and concentrated to give the acid K as an oil, which was characterized by NMR spectra and used without purification.

L. trans-2-[[2-[[[2-[[2-(4-Chlorophenyl)-ethyl]amino]-1-(hydroxymethyl)-2-oxoethyl]-amino]carbonyl]cyclopentyl]methyl]benzenepropanoic acid, methyl ester, fast moving isomer (FMI); and M. trans-2-[[2-[[[2-[[2-(4-Chlorophenyl)-ethyl]amino]-1-(hydroxymethyl)-2-oxoethyl]-amino]carbonyl]cyclopentyl]methyl]benzenepropanoic acid, methyl ester, slow moving isomer (SMI)

A solution of acid K (2.73 mmol), 1-hydroxybenzotriazole (461 mg, 3.41 mmol, 1.25 eq) and (2-p-chlorophenylethylamido)-S-serine hydrochloride (914 mg, 3.28 mmol, 1.2 eq) in dimethylformamide (25 mL) was stirred at 0°–5° C. After 5 min, triethylamine (0.95 mL, 6.8 mmol, 2.5 eq) was added dropwise. Thirty minutes later, 1-(3-dimethylaminopropyl)-3-ethyl carbodiimide hydrochloride (652 mg, 3.41 mmol, 1.25 eq) was added. The mixture was allowed to warm to room temperature and stirred for 22 hours. The reaction was diluted with ethyl acetate (160 mL) and washed with 1N hydrochloric acid solution (2×60 mL) and water (60 mL), dried (magnesium sulfate), filtered and taken to dryness in vacuo. The residue was chromatographed on a silica gel column (65 g, Merck), eluting with mixtures of ethyl acetate in dichloromethane (1:1, followed by 7:3) to give, after trituration with ether, some of the faster moving isomer (416 mg), and the rest of the product was obtained as a mixture of isomers (770 mg). The mixture was rechromatographed on silica gel (65 g, Merck), eluting with 1–2% methanol in dichloromethane to give the fast-moving isomer L (total 523 mg, 37%) and the slow-moving isomer M (407 mg, 29%) as well as some material that was mixed isomers (103 mg, 7%). All material was solid. The samples were characterized by NMR spectra.

TLC: $R_f$=0.57(FMI) and 0.49(SMI), silica gel, ethyl acetate, UV and cerium disulfate.

The absolute configuration of these isomers is not known. Rotations: FMI:$[\alpha]_D$=−27.4° (c=0.7, methanol) SMI:$[\alpha]_D$= −3.7° (c=0,6, methanol)

N. (−)-trans-2-[[2-[4-[[[2-(4-Chlorophenyl)-ethyl]amino]carbonyl]-4,5-dihydro-2-oxazolyl]cyclopentyl]methyl]benzenepropanoic acid, methyl ester The fast-moving isomer L (516 mg, 1.0 mmol) was partially dissolved in dry dichloromethane (10 mL) and treated with triethylamine (182 mL, 1.3 mmol, 1.3 eq). The mixture was cooled to −10° C. and methanesulfonyl chloride (86 mL, 1.1 mmol, 1.1 eq) was added dropwise. The mixture remained heterogeneous and after 15 minutes more dichloromethane (5 mL) was added. After 40 minutes, more mesyl chloride (40 mL) was added followed, at one hour, by triethyamine (90 mL) and distilled tetrahydrofuran (5 mL). The mixture was stirred cold for a total of two hours and then diluted with chloroform (50 mL). The solution was washed with 1N hydrochloric acid (2×50 mL) and a 1:1 mixture of brine and saturated sodium bicarbonate solution (50 mL). The organic layer was dried (magnesium sulfate), filtered and freed of solvent in vacuo, leaving the mesylate as a white solid. This solid was dissolved in acetone (50 mL) and treated with powdered potassium carbonate (1.38 g, 10 mmol, 10 eq). The mixture was heated under reflux for 70 minutes, cooled and filtered to remove the solid. The filtrate was taken to dryness in vacuo. The residue was chromatographed on silica gel (50 g, Merck) eluting with 1–3% methanol in dichloromethane to give oxazoline N (392 mg, 79%), which was characterized by NMR spectra.

TLC: $R_f$=0.48, silica gel, 5% methanol in dichloromethane, UV and cerium disulfate.

O. (−)-trans-2-[[2-[4-[[[2-(4-Chlorophenyl)-ethyl]amino]carbonyl]-2-oxazolyl]cyclopentyl]methyl]benzenepropanoic acid, methyl ester Nickel peroxide (250 mg) was added to a stirred solution of oxazoline N (392 mg, 0.79 mmol) in dry methylene chloride (8 mL). The mixture was stirred at room temperature under an argon atmosphere. Additional nickel peroxide (a total of 600 mg) was added in 200 mg portions over a six-hour period. The reaction was nearly complete and was left stirring at room temperature overnight. The mixture was then diluted with ethyl acetate (30 mL) and filtered through a magnesium sulfate pad. The solids were washed with ethyl acetate (5×20 mL). The filtrate was concentrated and the residue was chromatographed on a silica gel column (40 g, Merck), eluting with 20–30% ethyl acetate in hexane to obtain oxazole methyl ester O (17, 255 mg, 65% ) as a white solid, which was characterized by NMR spectra.

TLC: $R_f$=0.36, silica gel, ethyl acetate:hexane (1:1), UV and cerium disulfate.

P. (−)-trans-2-[[2-[4-[[[2-(4-Chlorophenyl)-ethyl]aminocarbonyl]-2-oxazolyl]cyclopentyl]methyl]benzenepropanoic acid A solution of lithium hydroxide (205 mg, 5 mmol) in water (5 mL) was added to a stirred solution of ester O (255 mg, 0.516 mmol) in distilled tetrahydrofuran (15 mL). After 6.5 hours, the mixture was diluted with ethyl acetate (100 mL) and washed with 1N hydrochloric acid solution (50 mL) and brine (50 mL). The ethyl acetate extract layer was dried (magnesium sulfate), filtered and concentrated in vacuo to obtain a solid which was triturated with ether and harvested by filtration to give Example 3 (204 mg, 82%) as a white solid.

Melting point 130°–1330° C.

$[\alpha]_D$=−6.2° (c=0.8, methanol).

EXAMPLE 4

(+)-trans-2-[[2-[4-[[[2-(4-Chlorophenyl)ethyl]-amino]carbonyl]-2-oxazolyl]cyclopentyl]methyl]-benzenepropanoic acid, slow moving isomer A. (+)-trans-2-[[2-[4-[[[2-(4-Chlorophenyl)-ethyl]amino]carbonyl]-4,5-dihydro-2-oxazolyl]cyclopentyl]methyl]benzenepropanoic acid, methyl ester The slow moving isomer L from Example 3 (400 mg, 0.778 mmol) was dissolved in dry dichloromethane (10 mL) and treated with triethylamine (140 mL, 1.3 mmol, 1.3 eq). The mixture was cooled to −10° C. and methanesulfonyl chloride (66 mL, 0.86 mmol, 1.1 eq) was added dropwise. The mixture was stirred cold for 40 minutes and then diluted with dichloromethane (50 mL). The solution was washed with 1N hydrochloric acid (2×50 mL) and a 1:1 mixture of brine and saturated sodium bicarbonate solution (50 mL). The organic layer was dried (magnesium sulfate), filtered and freed of solvent in vacuo, leaving the mesylate as a colorless glass. This glass was dissolved in acetone (40 mL) and treated with powdered potassium carbonate (1.07 g, 7.8 mmol, 10 eq.). The mixture was heated under reflux for 70 minutes, cooled and filtered to remove the solid, which was washed with more acetone. The filtrate was taken to dryness in vacuo. The residue was chromatographed on silica gel (40 g, Merck), eluting with 1–2% methanol in dichloromethane to give (255 mg, 66%), which was characterized by NMR spectra. TLC: $R_f$=0.48, silica gel, 5% methanol in dichloromethane, UV and cerium disulfate.

B. (+)-trans-2-[[2-[4-[[[2-(4-Chlorophenyl)-ethyl]amino]carbonyl]-2-oxazolyl]cyclopentyl]methyl]benzenepropanoic acid, methyl ester Nickel peroxide (250 mg) was added to a stirred solution of oxazoline A (255 mg, 0.51 mmol) in dry methylene chloride (8 mL). The mixture was stirred at room temperature under an argon atmosphere. Additional nickel peroxide (a total of 600 mg) was added in 200 mg portions over a six-hour period. The reaction was nearly complete and was left stirring at room temperature overnight. The mixture was then diluted with ethyl acetate (30 mL) and filtered through a magnesium sulfate pad. The solids were washed with ethyl acetate (5×20 mL). The filtrate was concentrated and the residue was chromatographed on a silica gel column (40 g, Merck), eluting with 20–30% ethyl acetate in hexane to obtain oxazole methyl ester B (166 mg, 66% ) as a white solid, which was characterized by NMR spectra.

TLC: $R_f$=0.36, silica gel, ethyl acetate:hexane (1:1), UV and cerium disulfate.

C. (+)-trans-2-[[2-[4-[[[2-(4-Chlorophenyl)-ethyl]amino]carbonyl]-2-oxazolyl]cyclopentyl]methyl]benzenepropanoic acid A solution of lithium hydroxide (164 mg, 4 mmol) in water (4 mL) was added to a stirred solution of ester B (166 mg, 0.336 mmol) in distilled tetrahydrofuran (10 mL). After 6.5 hours, the mixture was diluted with ethyl acetate (75 mL) and washed with 1N hydrochloric acid solution (30 mL) and brine (30 mL). The ethyl acetate extract layer was dried (magnesium sulfate), filtered and concentrated in vacuo to obtain a solid, which was triturated with ether and harvested by filtration to give Example 4 (106 mg, 66%) as a white solid.

Melting point 132°–135° C.

$[\alpha]_D$=+5.6° (c=0.6, methanol).

EXAMPLE 5

2-[[2-[4-[[(4-Cyclohexylbutyl)amino]carbonyl]-2-oxazolyl]phenyl]methyl]benzenepropanoic acid A. 3-(2-Bromophenyl)-2-propenoic acid, methyl ester To a stirred solution of 161.2 g (871 mmol) of 2-bromobenzaldehyde in 700 mL of dry tetrahydrofuran (distilled from potassium/benzophenone) at room temperature under argon, was added 298.4 g (892 mmol, 1.024 equiv) of methyl(triphenylphosphoranylidene)acetate (Aldrich) over 1 hour in 20 g portions. Reaction was mildly exothermic and the mixture became homogeneous. The resulting solution was stirred for 18 hours during which some precipitate formed. Addition of 200 mL hexane caused further precipitation. Filtration was followed by evaporation. The residue was slurried with a large volume of hexane (more precipitation) and refrigerated overnight. This was filtered, and the filtrate was passed through a plug of silica gel (approximately 1 kg), eluting with 10% ethyl acetate (EtOAc) in hexane. The eluant was concentrated in vacuo to give 201.5 g of a colorless oil. This oil was pure title compound as a 4:1 mixture of double bond isomers (trans predominating). The yield of title compound was 96%.

B. 2-Bromobenzenepropanoic acid, methyl ester

A mixture of 201.5 g (836 mmol) of the Part A acrylate and 8.4 g of 5% rhodium on alumina catalyst (MCB) in 1.0 L of methanol was stirred at room temperature under an atmosphere of hydrogen (balloon) for over 8 hours. $^1$H NMR analysis of an aliquot showed about a 1:1 mixture of title compound and trans Part A compound with no cis Part A compound. The mixture was diluted with 500 mL additional methanol and 12.6 g more catalyst was added. After hydrogenation overnight, the reaction was complete. The reaction mixture was passed through Celite and a Millipore/Fluoropore membrane filter (0.5 µm FH) with a prefilter pad, and the filtrate was concentrated in vacuo to obtain two immiscible oils. One of the oils was water-soluble and gave a highly acid aqueous solution. Solid sodium bicarbonate and sodium sulfate were carefully added (gas was evolved). The mixture was diluted with dichloromethane, filtered, and evaporated (and re-evaporated with dichloromethane to drive off methanol) to obtain 196.9 g of clear oil. This oil was 95% pure title compound with 5% of debromo title compound. The corrected yield of the title compound was 92% (187.1 g).

C. 3-(2-Bromobenzene)propan-1-ol

To a stirring solution of 196.9 g (95% pure=187.1 g, 770 mmol) of compound B in 770 mL of toluene under argon cooled to 0° C. (ice bath), 830 mL of 1.0M diisobutylaluminum hydride (DIBAL-H) in toluene solution (830 mmol, Aldrich) was added over 45 minutes. The reaction was not very exothermic. After the mixture was stirred for 1 hour, TLC indicated approximately half of the starting material remained. Next, 580 mL of 1.5 M DIBAL-H in toluene solution (870 mmol, Aldrich) was added slowly. The ice bath was removed and stirring was continued for 2 hours. The mixture was then poured slowly into 1.2 L of 6M aqueous HCl stirring in an ice bath. This quench was exothermic and gas was evolved. After the mixture was recooled to 0°, the layers were separated, and the organic layer was washed with 1M aqueous hydrochloric acid and brine. It was then dried over sodium sulfate and magnesium sulfate and evaporated (and re-evaporated with dichloromethane to drive off toluene) to obtain 173.0 g of clear, colorless oil. This oil was 95% pure title compound with 5% of debromo title compound. The corrected yield of the title compound was 99% (164.3 g).

D. 1-Bromo-2-[3-[[Dimethyl(1,1,2-trimethyl-propyl)silyl]oxy]propyl]benzene

To a solution of 29.0 g (135 mmol) of the crude Part C alcohol and 24.1 g (135 mmol, Petrarch) of thexyldimethylchlorosilane in 200 mL of dry methylene chloride (distilled from phosphorous pentoxide) was added at room temperature 20 mL (143 mmol, distilled from calcium hydride) of triethylamine and then 200 mg (1.64 mmol, Aldrich) of 4-dimethylaminopyridine. The reaction mixture was stirred at room temperature for 18 hours. The resulting slurry was diluted with 100 mL of hexane, cooled to 0° C. with stirring for 15 minutes, then filtered to remove solid triethylamine hydrochloride. The filtrate was concentrated in vacuo to give an oil. The crude oil was purified by flash chromatography (Merck silica, 15×10 cm, 1:9 ethyl acetate/petroleum ether) to afford 45.5 g (127 mmol, 94%) of the title compound as a colorless liquid.

E. 1,1-Bis(hydroxymethyl)benzene

To a solution of 5.00 g (41.0 mmol, Aldrich) of phthalide in 75 mL of ether (distilled from sodium/benzophenone) and 25 mL of tetrahydrofuran (distilled from sodium/benzophenone) cooled in an ice-bath was added 1.56 g (41 mmol, Aldrich) of lithium aluminum hydride in about 0.5 g portions at 5-minute intervals. The reaction mixture was stirred at 0° for one hour then at room temperature for 16 hours. The resulting mixture was cooled in an ice-bath, then quenched by slow sequential addition of 1.5 mL of water, 1.5 mL of 15% aqueous sodium hydroxide solution, and 4.5 mL of water. The reaction was stirred for 30 minutes, and then the precipitated aluminum salts were removed by filtration. The filtrate was concentrated in vacuo to give an oil. The oil was dissolved in 50 mL of ethyl acetate, washed with 25 mL of 1M aqueous hydrochloric acid solution and 25 mL of aqueous sodium hydroxide solution, dried (magnesium sulfate), and concentrated in vacuo to give a solid. The crude solid was recrystallized (ethyl acetate/hexane) to afford 3.50 g (25.4 mmol, 62%) of diol E as white crystals.
Melting point 63–64°.

F. 1-[[[(1,1-Dimethylethyl)diphenylsilyl]oxy]-methyl]-2-hydroxymethylbenzene

The oil was removed from 810 mg (60% in oil, 20 mmol, Aldrich) of sodium hydride dispersion by three washes with hexane, then the residue was covered with 15 mL of tetrahydrofuran (distilled from sodium/benzophenone). To the resulting stirred slurry was added dropwise a solution of 2.80 g (20.3 mmol) of diol E in 15 mL of tetrahydrofuran over about 15 min. Gas was evolved and the reaction was exothermic. After the addition was complete the reaction was heated in a warm water bath (50°) for an additional 1 hour. The resulting mixture was cooled to room temperature, and then 5.58 g (20.3 mmol, Aldrich) of t-butylchlorodiphenylsilane was added dropwise over 10 min. The reaction was stirred for one hour, then partitioned between 120 mL of ice-cold 1M aqueous hydrochloric acid solution and 75 mL of ethyl acetate. The organic layer was separated, washed with 100 mL of 1M aqueous sodium hydroxide solution, 50 mL of brine, dried (magnesium sulfate) and concentrated in vacuo to give 7.63 g (20.3 mmol, 100%) of crude protected alcohol F as a colorless oil.

G. 1-[[[(1,1-Dimethylethyl)diphenylsilyl]oxy]-methyl]-2-(iodomethyl)benzene

To a solution of 7.55 g (20.1 mmol) of alcohol F and 4.2 mL (30 mmol, distilled from calcium hydride) of triethylamine in 20 mL of dry methylene chloride (distilled from phosphorous pentoxide) cooled to −20° was added dropwise a solution of 1.8 mL (23 mmol, Aldrich) of methanesulfonyl chloride in 3 mL of methylene chloride over 5 min. The reaction was stirred for 10 minutes, then diluted with 50 mL of ice-cold hexane and added to 50 mL of ice-cold 1M aqueous hydrochloric acid solution. The organic layer was separated, washed with an additional 50 mL of ice-cold 1M aqueous hydrochloric acid solution, 25 mL brine, dried (magnesium sulfate) and concentrated in vacuo (cold water bath) to give the crude mesylate as a colorless oil. The crude mesylate was used immediately.

To a stirred solution of the crude mesylate (about 20.1 mmol) in 100 mL of reagent acetone was added 6.0 g (40.3 mmol) of sodium iodide. A precipitate formed immediately and the addition was mildly exothermic. The mixture was stirred for 15 minutes, then partitioned between 100 mL of hexane and 300 mL of water. The organic layer was separated, washed with 300 mL of 5% aqueous sodium bisulfite, 300 mL of water, 100 mL of brine, dried (magnesium sulfate) and concentrated in vacuo to give a yellow oil. The crude material was purified by flash chromatography (Merck silica, 10×5.0 cm, 1:9 ethyl acetate/hexane) to give 9.20 g (18.9 mmol, 94%) of iodide G as a yellow oil.

H. Dilithium tetrachlorocuprate

This compound was prepared as described by M. Tamura, J. Kochi, *Synthesis,* 303 (1971). To a mixture of 334 mg (2.50 mmol, Aldrich, 97%) of anhydrous copper(II) chloride and 212 mg (5.00 mmol, Aldrich) of anhydrous lithium chloride was added 25 mL of dry tetrahydrofuran (distilled from sodium/benzophenone). The mixture became homogeneous after stirring for about 15 minutes. The resulting orange solution was used without further purification or characterization.

I. 1-[[[(1,1-Dimethylethyl)diphenylsilyl]oxy]-methyl]-2-[[2-[3-[[(1,1-dimethylethyl)-diphenylsilyl]oxy]propyl]phenyl]methyl]-benzene To 243 mg (10.0 mmol, Aldrich) of freshly hammer-crushed magnesium turnings covered with 5 mL of dry tetrahydrofuran (distilled from sodium/benzophenone) was added a small crystal of iodine then 20 µL of 1,2-dibromoethane. A reaction started immediately. After about 5 minutes, 3.00 g (8.40 mmol of bromide D was added in one portion. An exothermic reaction started after warming with a heat gun and, after initiation, refluxed without external heating. After stirring for 30 minutes, the reaction mixture was refluxed for an additional one hour with the aid of an oil bath. The gray solution was cooled to room temperature and 5 mL of tetrahydrofuran was added to insure solubility of the Grignard reagent. The resulting solution was added dropwise over about 20 minutes to a solution of 4.08 g (8.40 mmol) of iodide G and 0.85 mL (0.1M in tetrahydrofuran, 0.085 mmol) of freshly prepared dilithium tetrachlorocuprate solution from part H cooled to 0°. The reaction temperature was maintained below 10° during the addition. The reaction mixture was stirred for an additional one hour then partitioned between 120 mL of saturated aqueous ammonium chloride solution and 50 mL of ether.

The organic layer was separated, washed with 50 mL of brine, dried (magnesium sulfate) and concentrated in vacuo to give 5.55 g of crude diprotected compound I.

J. 2-[2-[[[[(1,1-Dimethylethyl)diphenylsilyl]-oxy]methyl]phenyl]methyl]benzenepropanoic acid, methyl ester To a solution of 5.55 g of crude diprotected compound I in 65 mL of reagent acetone cooled in an ice-bath was added dropwise 8.0 mL of Jones reagent (2.6M in $Cr^{+6}$, prepared as described in Fieser & Fieser, Reagents for Organic Synthesis, Vol.1, p. 142). The reaction mixture was stirred for 2 hours and then the excess reagent was quenched by addition of 4 mL of isopropanol and stirred for an additional 30 min. The resulting green slurry was filtered through Celite®. The filtrate was concentrated in vacuo to give a yellow oil. The oil was dissolved in 75 mL of ether and washed with two-75-mL portions of 5% aqueous sodium bisulfite solution, followed by 25 mL of brine. The resulting solution of the crude acid was cooled in an ice-bath and treated with excess ethereal diazomethane (prepared from 8 g of N-methyl-N'-nitro-N-nitrosoguanidine). After 10 minutes, the excess diazomethane was quenched by addition of glacial acetic acid, and the solution concentrated in vacuo to give an oil. The crude oil was purified by flash chromatography (Merck silica, 15×5.0 cm, 1:9 ether/hexane) to afford 2.63 g (5.04 mmol, 60% from bromide D) of ester J as a colorless oil.

K. 2-[[2-(Hydroxymethyl)phenyl]methyl]benzenepropanoic acid, methyl ester

To a solution of 2.60 g (4.98 mmol) of ester J in 10 mL of tetrahydrofuran (distilled from sodium/benzophenone) was added 5.5 mL (1.0M in tetrahydrofuran, 5.5 mmol, Aldrich) of tetra-n-butylammonium fluoride solution at room temperature. The reaction mixture was stirred for 45 minutes and then partitioned between 50 mL of 1M aqueous hydrochloric acid solution and 25 mL of ethyl acetate. The organic layer was separated and the aqueous layer was extracted with an additional 25 mL of ethyl acetate. The organic extracts were combined, dried (magnesium sulfate) and concentrated in vacuo to give a yellow oil. The crude oil was purified by flash chromatography (Merck silica, 15×3.0 cm, 1:2 ethyl acetate/hexane) to afford 1.24 g (4.37 mmol, 88%) of alcohol K as a colorless oil.

L. 2-[(2-Carboxyphenyl)methyl]benzenepropanoic acid, methyl ester

To a solution of 600 mg (2.11 mmol) of alcohol K in 5 mL of reagent acetone cooled to 0° was added dropwise 2.0 mL of Jones reagent (vide supra). The reaction mixture was warmed to room temperature, stirred for 30 minutes, and then an additional 5 mL of acetone and 2.0 mL of Jones reagent were added. The reaction was stirred for one hour, then quenched with 2 mL of isopropanol. After 10 minutes, the resulting green slurry was filtered through Celite®. The filtrate was concentrated in vacuo and the residue partitioned between 20 mL of 1M aqueous hydrochloric acid solution and 20 mL of warm ethyl acetate. The organic layer was separated, washed with 20 mL of brine, dried (magnesium sulfate) and concentrated in vacuo to give 611 mg (2.05 mmol, 97%) of crude acid L as a white solid.

Melting point 123°–126°.

M. N-(4-Cyclohexylbutyl)-L-serinamide, monohydrochloride

To a solution of 14.3 g of 4-cyclohexyl-butylamine hydrochloride (74.7 mmol), 16.1 g of t-butoxycarbonyl-(L)-serine (78.4 mmol, 1.05 equiv), 10.1 g of 1-hydroxybenzotriazole hydrate (74.7 mmol, 1.00 equiv), and 7.9 g N-methylmorpholine (78.4 mmol, 1.05 equiv) in 200 mL of dimethylformamide stirring under argon at 0° C., was added 15.0 g of 1-(3-dimethylaminopropyl)-3-ethylcarbodiimide hydrochloride (WSC) (78.4 mmol, 1.05 equiv) in a single portion. All of the WSC dissolved. The reaction mixture was allowed to slowly warm to room temperature overnight, and a precipitate formed. The mixture was rotoevaporated (60° bath) to 90 g of oil plus solid. This oil and solid mixture was diluted with 400 mL of ethyl acetate and washed with 200 mL 0.3M aqueous hydrochloric acid twice (all solids dissolved at this point), then 200 mL of 1.0M aqueous sodium bicarbonate twice. To the organic layer was added 500 mL of toluene, and this was dried over sodium sulfate and evaporated. After coevaporation with toluene, 28.4 g of a thick solidifying oil was obtained. This material was dissolved in 150 mL of methylene chloride and, while stirring at room temperature under argon, 100 mL of trifluoroacetic acid was added (gas was evolved). After 4 hours, the solvent was evaporated. After coevaporation with chloroform, the crude product was flash-chromatographed (1.0 kg silica gel, 10% (10% concentrated aqueous ammonia in methanol in methylene chloride) to obtain 13.4 g of 95% pure compound M as a white solid. The corrected yield was 70% overall from 4-cyclohexylbutylamine hydrochloride.

N. 2-[[2-[[[2-[(4-Cyclohexylbutyl)amino]-1-(hydroxymethyl)-2-oxoethyl]amino]carbonyl]-phenyl]methyl]benzenepropanoic acid, methyl ester To a solution of 585 mg (1.96 mmol) of acid L in 10 mL of sieve-dried dimethylformamide cooled to 0° was added 278 mg (2.06 mmol, Aldrich) of 1-hydroxybenzotriazole hydrate, 545 mg (1.96 mmol) of amine hydrochloride M, then 0.60 mL (4.3 mmol, distilled from calcium hydride) of triethylamine. The mixture was stirred for several minutes, and then 395 mg (2.06 mmol) of 1-(3-dimethylaminopropyl)-3-ethylcarbodiimide hydrochloride (WSC) was added. The resulting slurry was stirred at 0° for 3 hours then at room temperature for 16 hours. The reaction was partitioned between 50 mL of 1M aqueous hydrochloric acid solution and 25 mL of ethyl acetate. The organic layer was separated, washed with two 50-mL portions of water, dried (magnesium sulfate) and concentrated in vacuo to give a solid. The crude solid was purified by flash chromatography (Merck silica, 12×5.0 cm, methylene chloride load, ethyl acetate elution) to afford 775 mg (1.48 mmol, 76%) of amide N as a colorless solid, m.p. 84°–86°.

O. 2-[[2-[4-[[(4-Cyclohexylbutyl)amino]-carbonyl]-4,5-dihydro-2-oxazolyl]phenyl]-methyl]benzenepropanoic acid, methyl ester To a solution of 725 mg (1.39 mmol) of amide N in 6 mL of acetonitrile and 2 mL of methylene chloride (distilled from phosphorous pentoxide) was added 545 mg (2.08 mmol, Aldrich) of triphenylphosphine and 0.45 mL (2.6 mmol, Aldrich) of diisopropylethylamine. The mixture was stirred until homogeneous, and then 0.20 mL (2.1 mmol) of reagent carbon tetrachloride was added in one portion. The reaction mixture was stirred for 18 hours, then partitioned between 50 mL of saturated aqueous sodium bicarbonate solution and 30 mL of ethyl acetate. The organic layer was separated, washed with 50 mL of water, 25 mL of brine, dried (magnesium sulfate) and concentrated in vacuo to give an oily solid. The crude material was purified by flash chromatography (Merck silica, 12×5.0 cm, 2:1 ethyl acetate/hexane) to give 685 mg (1.36 mmol, 98%) of oxazoline O as a pale yellow oil.

P. 2-[[2-[4-[[(4-Cyclohexylbutyl)amino]-carbonyl]-2-oxazolyl]phenyl]methyl]-benzenepropanoic acid, methyl ester To a mixture of 397 mg (1.78 mmol) of copper(II) bromide in 3 mL of ethyl acetate was added 0.53 mL (3.6 mmol) of 1,8-diazabicyclo-[5.4.0]undec-7-ene at room temperature. The mixture was stirred for 10 minutes, and then a solution of 450 mg (0.89 mmol) of oxazoline O in 3 mL of chloroform was added in one portion. The reaction mixture was stirred for 18 hours (TLC showed about 40% complete) then an additional 397 mg (1.78 mmol) of copper (II) bromide and 0.53 mL (3.6 mmol) of 1,8-diazabicyclo [5.4.0]undec-7-ene were added. The resulting dark mixture was stirred for an additional 24 hours (TLC shows reaction about 75% complete), then partitioned between 50 mL of ethyl acetate and 75 mL of 2:1 saturated aqueous ammonium chloride/concentrated ammonium hydroxide solution. The organic layer was separated, dried (magnesium sulfate) and concentrated in vacuo to give an oil. The crude material was purified by flash chromatography (Merck silica, 20×3.0 cm, 1:3 ethyl acetate/hexane) to afford 205 mg (0.41 mmol, 46%) of oxazole P as a pale yellow solid.

Q. 2-[[2-[4-[[(4-Cyclohexylbutyl)amino]-carbonyl]-2-oxazolyl]phenyl]methyl]-benzenepropanoic acid To a solution of 190 mg (0.38 mmol) of ester P in 5 mL of 4:1 tetrahydrofuran/water at room temperature was added 64 mg (1.5 mmol, Aldrich) of lithium hydroxide monohydrate. The mixture was stirred rapidly for 18 hours, then acidified with 3 mL of 1M aqueous hydrochloric acid solution and partitioned between 20 mL of ethyl acetate and 20 mL of water. The organic layer was separated, washed with 20 mL of brine, dried (magnesium sulfate) and concentrated in vacuo to give a solid. The crude solid was recrystallized (ethyl acetate/hexane) to afford 170 mg (0.35 mmol, 92%) of Example 5 as white crystals.

Melting point 117°–119°.
IR(KBr): 3432, 2924, 1714, 1656, 1604, 1523, 1489, 1449, 1189 cm$^{-1}$.
MS(CI): 489 (M+H)$^+$.
TLC: $R_f$ (silica gel, 1:9 methanol/methylene chloride)=0.56, ammonium molybdate/ceric sulfate and UV, homogeneous.
Analysis Calc'd for $C_{30}H_{36}N_2O_4$ C 73.74; H, 7.43; N, 5.73. Found: C, 73.75; H, 7.49; N, 5.56.

EXAMPLE 6

2-[[2-[4-[[(3,3-Dimethylbutyl)amino]carbonyl]-2-oxazolyl]phenyl]methyl]benzenepropanoic acid A. N-[2-[[2-(3-Methoxy-3-oxopropyl)phenyl]-methyl]benzoyl]-L-serine, phenylmethyl ester To a solution of 490 mg (1.64 mmol) of acid-ester L from Example 5 in 10 mL of sieve-dried dimethylformamide (Burdick and Jackson) cooled in an ice-bath were added 243 mg (1.80 mmol, Aldrich) of 1-hydroxybenzotriazole hydrate, 418 mg (1.80 mmol, Sigma) of L-serine benzyl ester hydrochloride and 0.55 mL (3.9 mmol, distilled from calcium hydride) of triethylamine. The mixture was stirred for several minutes, and then 346 mg (1.80 mmol, Aldrich) of 1-(3-dimethylaminopropyl)-3-ethyl-carbodiimide hydrochloride (WSC) was added in one portion. The reaction was stirred at 0° for one hour then at room temperature for 3 hours. The resulting slurry was partitioned between 50 mL of 1N aqueous hydrochloric acid solution and 50 mL of ethyl acetate. The organic layer was separated, washed with two 50-mL portions of water, dried (magnesium sulfate) and concentrated in vacuo to give an oil. The crude oil was purified by flash chromatography (Merck silica, 15×3.0 cm, 2:1 ethyl acetate/hexane) to afford 592 mg (1.25 mmol, 76%) of amide-ester A as a white solid.

Melting point 89°–91°.

B. 4,5-Dihydro-2-[2-[[2-(3-methoxy-3-oxo-propyl)phenyl]methyl]phenyl]-4-oxazole-carboxylic acid, phenylmethyl ester To a solution of 570 mg (1.20 mmol) of amide-ester A and 472 mg (1.80 mmol, Aldrich) of triphenylphosphine in 6 mL of acetonitrile (Burdick and Jackson) was added at room temperature 420 µL (2.4 mmol, Aldrich) of diisopropylethylamine then 175 µL (1.8 mmol, Mallinckrodt) of carbon tetrachloride. The reaction mixture was stirred for 16 hours and then partitioned between 25 mL of saturated sodium bicarbonate solution and 25 mL of ethyl acetate. The organic layer was separated, washed with 25 mL of brine, dried (sodium sulfate) and concentrated in vacuo to give an orange oil. The crude material was purified by flash chromatography (Merck silica, 15×3.0 cm, 1:4 ethyl acetate/hexane) to give 242 mg (0.53 mmol, 44%) of oxazoline B as a colorless oil. Also isolated was 130 mg (0.28 mmol, 24%) of a less polar by-product identified as the acrylate derived by elimination of water from starting material A.

C. 2-[2-[[2-(3-Methoxy-3-oxopropyl)phenyl]-methyl]phenyl]-4-oxazolecarboxylic acid, phenylmethyl ester A mixture of 236 mg (1.06 mmol, Aldrich) of copper(II) bromide and 315 mL (2.1 mmol, Aldrich) of 1,8-diazabicyclo[5.4.0]undec-7-ene in 2 mL of ethyl acetate (Burdick and Jackson) was stirred for 10 minutes then a solution of 240 mg (0.53 mmol) of oxazoline B in 2 mL of chloroform (Burdick and Jackson) was added in one portion. The reaction mixture was stirred for 24 hours and then added to 30 mL of 2:1 saturated aqueous ammonium chloride solution/concentrated ammonium hydroxide and extracted with 30 mL of ethyl acetate. The organic layer was separated, washed with 20 mL of 1M aqueous hydrochloric acid solution, 20 mL of brine, dried (magnesium sulfate) and concentrated in vacuo to give an oil. The crude oil was purified by flash chromatography (Merck silica, 10×1.5 cm, 1:2 ethyl acetate/hexane) to afford 142 mg (0.31 mmol, 59%) of oxazole C as an oil.

D. 2-[2-[[2-(3-Methoxy-3-oxopropyl)phenyl]-methyl]phenyl]-4-oxazolecarboxylic acid A mixture of 140 mg (0.31 mmol) of benzyl ester C and 14 mg of 20% palladium hydroxide on carbon catalyst in 3 mL of reagent ethyl acetate was stirred under an atmosphere of hydrogen (balloon) for 4 hour The reaction mixture was then passed through a 0.4 micron polycarbonate membrane and the filtrate concentrated in vacuo to give 115 mg (0.31 mmol, 100%) of acid D as a white solid.

E. 2-[[2-[4-[[(3,3-Dimethylbutyl)amino]-carbonyl]-2-oxazolyl]phenyl]methyl]-benzenepropanoic acid, methyl ester To a solution of 112 mg (0.31 mmol,) of oxazole acid D in 3 mL of dry methylene chloride (distilled from phosphorous pentoxide) was added at room temperature a small drop of dimethylformamide then 35 μL (0.40 mmol, Aldrich) of oxalyl chloride. The solution was stirred until gas evolution ceased, (about 20 minutes), then concentrated in vacuo to give the acid chloride as a pale yellow oil.

To a solution of the crude acid chloride (about 0.31 mmol) in 3 mL of dry methylene chloride cooled in an ice-bath was added 65 μL (0.46 mmol, distilled from calcium hydride) of triethylamine followed by 50 μL (0.37 mmol, Aldrich) of 3,3-dimethylbutylamine. The reaction mixture was stirred for 30 minutes, then partitioned between 20 mL of 1M aqueous hydrochloric acid solution and 20 mL of ethyl acetate. The organic layer was separated, dried (magnesium sulfate) and concentrated in vacuo to give an oil. The crude material was purified by flash chromatography (Merck silica, 12×1.5 cm, 1:2 ethyl acetate/hexane) to afford 122 mg (0.27 mmol, 88%) of ester E as a colorless oil.

F. 2-[[2-[4-[[(3,3-Dimethylbutyl)amino]-carbonyl]-2-oxazolyl]phenyl]methyl]-benzenepropanoic acid A mixture of 120 mg (0.27 mmol) of ester E and 45 mg (1.1 mmol, Aldrich) of lithium hydroxide monohydrate in 6 mL of 2:1 tetrahydrofuran/water was stirred rapidly at room temperature for 16 hours then acidified by addition of 2.2 mL of 1M aqueous hydrochloric acid solution. The resulting solution was partitioned between 20 mL of water and 20 mL of ethyl acetate. The organic layer was separated, dried (magnesium sulfate) and then concentrated in vacuo to give a solid. The crude material was recrystallized (ethyl acetate/hexane) to afford 98 mg (0.23 mmol, 85%) of Example 6 as white crystals.

Melting point 182–183°.
IR(KBr): 3424, 2956, 1713, 1658, 1603, 1522, 1186, 1109 cm$^{-1}$.
MS(CI): 435 (M+H)$^+$.
TLC: $R_f$(silica gel, 1:9 methanol/methylene chloride)=0.47, ammonium molybdate/ceric sulfate and UV, homogeneous.

Analysis Calc'd for $C_{26}H_{30}N_2O_4$: C, 71.87; H, 6.96; N, 6.45. Found: C, 71.57; H, 6.97; N, 6.31.

EXAMPLE 7

3-[[2-[4-[[(-Cyclohexylbutyl)amino]carbonyl]-2-oxazolyl]phenyl]methyl]benzeneacetic acid A. 2-(3-Bromophenyl)ethan-1-ol To a solution of 10.0 g (46.5 mmol, Aldrich) of 3-bromophenylacetic acid in 100 mL of dry tetrahydrofuran (distilled from potassium/benzophenone), cooled to 0° C., was added dropwise over 40 minutes 61 mL (61 mmol, 1M/tetrahydrofuran, Aldrich) of borane-tetrahydrofuran solution. The reaction was stirred at room temperature for 16 hours, then cooled to 0° C. and quenched by the dropwise addition of 10 mL methanol. The reaction mixture was concentrated in vacuo and azeotroped with two 10-mL portions of methanol to give 9.35 g (46.5 mmol, 100%) of alcohol A as a clear oil.

B. 1-Bromo-3-[2-[[dimethyl(1,1,2-trimethylpropyl)silyl]oxy]ethyl]benzene

To a solution of 9.35 g (46.5 mmol) of crude alcohol A, 6.9 mL (49 mmol, distilled from calcium hydride) of triethylamine and 8.30 g (46.5 mmol, Petrarch) of thexyldimethylsilyl chloride in 100 mL of dry dichloromethane (distilled from phosphorus pentoxide) was added 68 mg (0.56 mmol, Aldrich) of 4-dimethylaminopyridine. The reaction was stirred at room temperature for 48 hours, then diluted with 100 mL of hexane and cooled to 0° C. for 2 hours. The resulting slurry was filtered; the filtrate was concentrated in vacuo to give a crude brown liquid. The crude liquid was flash-chromatographed (Merck silica, 100× 300 mm, 1:99 ethyl acetate/hexane) to give 11.4 g (33.3 mmol, 72%) of silyl ether B as a colorless liquid.

C. 3-[[2-[[[(1,1-Dimethylethyl)diphenylsilyl]-oxy]methyl]phenyl]methyl]benzene-acetic acid, methyl ester To a mixture of 599 mg (24.6 mmol, Aldrich) of freshly hammer-crushed magnesium turnings in 15 mL of dry tetrahydrofuran (distilled from sodium/benzophenone) was added a small crystal of iodine followed by 60 82 L of 1,2-dibromoethane. The reaction started after heating to 70° C. (oil bath). After 5 minutes of refluxing, about a 20% portion of the required 7.06 g (20.5 mmol) of bromide B was added. An exothermic reaction started with continuous heating (70° C.); after the reaction color became clear, the remaining bromide was added in one portion. The reaction mixture was refluxed for 2.5 hours at 70° C., and then the gray solution was cooled to room temperature and 15 mL of tetrahydrofuran was added to insure solubility of the Grignard reagent. The resulting solution was added dropwise over 20 minutes to a solution of 10.0 g (20.5 mmol) of iodide G from Example 5 and 2.1 mL (0.1M in tetrahydrofuran, 0.21 mmol) of freshly prepared dilithium tetrachlorocuprate solution (Example 5, Part H) in 25 mL of dry tetrahydrofuran stirred at 0° C. The reaction temperature was maintained below 10° C. during the addition. The reaction mixture was stirred for an additional 2 hours, then partitioned between 240 mL of saturated aqueous ammonium chloride solution/100 mL of ether. The organic layer was separated, washed with 100 mL of brine, dried (magnesium sulfate) and concentrated in vacuo to give a crude yellow oil.

To a solution of crude oil in 130 mL of reagent acetone, cooled to 0° C., was added dropwise 20 mL of Jones reagent (2.6M in Cr$^{+6}$). The reaction mixture was stirred for 2 hours, and then the excess reagent was quenched by addition of 30 mL of isopropanol and stirred for an additional 30 minutes.

The resulting green slurry was filtered through Celite®. The filtrate was concentrated in vacuo to give a yellow oil. The oil was dissolved in 150 mL of ether, then washed with two 150-mL portions of 5% aqueous sodium bisulfate solution, followed by 50 mL of brine. The resulting solution of the crude acid was cooled to 0° C. and treated with excess ethereal diazomethane (prepared from 25 g of N-methyl-N'-nitro-N-nitroso-guanidine). After 2 hours, the excess diazomethane was quenched by the addition of glacial acetic acid, and the solution was concentrated in vacuo to give a crude oil. The crude oil was flash-chromatographed (Merck silica, 100×250 mm, 1:9 ether/hexane) to give 6.60 g (12.9 mmol, 63%) of silyl ether C as a colorless oil.

D. 3-[[2-(Hydroxymethyl)phenyl]methyl]benzeneacetic acid, methyl ester

To a solution of 6.59 g (12.9 mmol) of silyl ether C in 30 mL of tetrahydrofuran (distilled from potassium/benzophenone), cooled to 0° C., was added dropwise over 15 minutes 14 mL (14 mmol, 1M/tetrahydrofuran, Aldrich) of tetra-n-butylammonium fluoride solution. The reaction was stirred at room temperature for 4 hours, and then the mixture was partitioned between 125 mL of ethyl acetate/150 mL of 1M hydrochloric acid. The aqueous layer was separated and extracted with two 50-mL portions of ethyl acetate. The combined ethyl acetate layers were dried (magnesium sulfate) and concentrated in vacuo to give a crude yellow oil. The crude oil was flash-chromatographed (Merck silica, 50×200 mm, 1:2 ethyl acetate/hexane) to give 2.62 g (9.69 mmol, 75%) of alcohol D as a colorless oil.

E. 3-[(2-Carboxyphenyl)methyl]benzeneacetic acid, methyl ester

To a solution of 2.62 g (9.69 mmol) of alcohol D in 60 mL of reagent acetone, cooled to 0° C., was added dropwise over 20 minutes 17 mL (2.6M in $Cr^{+6}$) of Jones reagent. The reaction was stirred at room temperature for 2 hours, and then the excess was quenched by the addition of 20 mL of isopropanol. The mixture was stirred for 40 minutes, then filtered through Celite. The filtrate was partitioned between 120 mL of 1M hydrochloric acid/120 mL of ethyl acetate; the aqueous layer was separated and extracted with three 60-mL portions of ethyl acetate. The combined ethyl acetate layers were dried (magnesium sulfate) and concentrated in vacuo to give a crude oil. The crude oil was flash-chromatographed (Merck silica, 50×150 mm, 1:1 ethyl acetate/hexane) to give 1.92 g (6.75 mmol, 70%) of acid E as a white solid.
Melting point 78°–80° C.

F. 3-[[2-[[[2-[(4-Cyclohexylbutyl)amino]-1-(hydroxymethyl)-2-oxoethyl]amino]carbonyl]-phenyl]methyl]benzeneacetic acid, methyl ester To a solution of 960 mg (3.38 mmol) of acid E in 20 mL of sieve-dried dimethylformamide (Burdick & Jackson), cooled to 0° C., was added 941 mg (3.38 mmol) of L-serine amide hydrochloride M from Example 5, 599 mg (3.55 mmol, 80%,) of 1-hydroxybenzotriazole hydrate and 1.04 mL (7.44 mmol, distilled from calcium hydride) of triethylamine. The mixture was stirred for 5 minutes at 0° C., then 680 mg (3.55 mmol) of 1-(3-dimethylaminopropyl)-3-ethylcarbodiimide hydrochloride (WSC) was added. The reaction mixture was warmed to room temperature and stirred for 16 hours then partitioned between 50 mL of ethyl acetate/100 mL of 1M hydrochloric acid. The aqueous layer was separated and extracted with two 30-mL portions of ethyl acetate. The combined ethyl acetate layers were washed with two 100-mL portions of water, dried (magnesium sulfate) and concentrated in vacuo to give a crude solid. The solid was flash-chromatographed (Merck silica, 50×120 mm, methylene chloride load, ethyl acetate elution) to give 1.39 g (2.73 mmol, 81%) of amide F as a colorless solid.

G. 3-[[2-[4-[[(-Cyclohexylbutyl)amino]-carbonyl]-4,5-dihydro-2-oxazolyl]phenyl]-methyl]benzeneacetic acid, methyl ester A solution of 1.38 g (2.71 mmol) of amide F, 1.07 g (4.07 mmol, Aldrich) of triphenylphosphine and 900 µL (5.15 mmol) of diisopropylethylamine in 12 mL of sieve-dried acetonitrile (Burdick & Jackson)/4 mL of methylene chloride (distilled from phosphorus pentoxide) was stirred at room temperature until homogeneous. To the reaction mixture was added in one portion 400 µL (4.07 mmol) of carbon tetrachloride. The reaction was stirred at room temperature for 18 hours, then the reaction mixture was partitioned between 80 mL of ethyl acetate/100 mL of saturated sodium bicarbonate solution. The aqueous layer was separated and extracted with two 40-mL portions of ethyl acetate. The combined ethyl acetate layers were washed with 100 mL of water, followed by 50 mL of brine, dried (magnesium sulfate) and concentrated in vacuo to give a crude orange solid. The crude solid was flash-chromatographed (Merck silica, 50×120 mm, 2:1 ethyl acetate/hexane) to give 1.23 g (2.51 mmol, 92%) of oxazoline G as a pale yellow oil.

H. 3-[[2-[4-[[(-Cyclohexylbutyl)amino]-carbonyl]-2-oxazolyl]phenyl]methyl]-benzeneacetic acid, methyl ester To a solution of 1.5 mL (9.9 mmol, Aldrich) of 1,8-diazabicyclo[5.4.0]undec-7-ene in 9 mL of ethyl acetate (Burdick & Jackson) was added 1.10 g (4.94 mmol, Aldrich) of cupric bromide. The mixture was stirred for 10 minutes at room temperature, then cooled in a water bath. A solution of 1.21 g (2.47 mmol) of oxazoline G in 9 mL of chloroform (Burdick & Jackson) was added dropwise over 10 minutes to the reaction mixture. The reaction was slightly exothermic. The reaction was stirred for 20 hours at room temperature, and then a second portion of 1.10 g (4.94 mmol) of cupric bromide was added; after 18 hours a third portion of 1.10 g (4.94 mmol) of cupric bromide was added. The reaction was stirred an additional 18 hours, at room temperature, then partitioned between 150 mL of 2:1 (saturated ammonium chloride solution/concentrated ammonium hydroxide)/100 mL of ethyl acetate. The aqueous layer was separated and extracted with two 50-mL portions of ethyl acetate. The combined ethyl acetate layers were dried (magnesium sulfate) and concentrated in vacuo to give a crude oil. The crude oil was flash-chromatographed (Merck silica, 50×150 mm, 1:5 ethyl acetate/hexane, then 1:3 ethyl acetate/hexane) to give 609 mg (1.25 mmol, 50%) of oxazole ester H as a white solid.
Melting point 64°–66° C.

I. 3-[[2-[4-[[(-Cyclohexylbutyl)amino]-carbonyl]-2-oxazolyl]phenyl]methyl]-benzeneacetic acid To a solution of 606 mg (1.24 mmol) of ester H in 12 mL of distilled tetrahydrofuran/3 mL of water, stirred at room temperature, was added 105 mg (2.49 mmol, Aldrich) of lithium hydroxide monohydrate. The reaction was stirred vigorously for 6 hours at room temperature, then quenched by the addition of 5 mL (5 mmol) of 1M hydrochloric acid. The mixture was partitioned between 40 mL of ethyl acetate/40 mL of water; the aqueous layer was separated and extracted with two 20-mL portions of ethyl acetate. The combined ethyl acetate layers were washed with 40 mL of brine, dried (magnesium sulfate) and concentrated in vacuo to give a white foam. The crude foam was recrystallized from hot ethyl acetate/hexane to give 252 mg (0.53 mmol, 43%) of Example 7 as a white solid.
Melting point 104°–106° C.
IR (KBr): 3354,3061,2920,2849,1723,1636,1603,1526 cm$^{-1}$.
MS(CI): 475 (M+H)$^+$.
TLC: R$_f$ (silica gel, 1:9 methanol/methylene chloride)=0.70, ammonium molybdate/ceric sulfate and UV, homogeneous.
Analysis Calc'd for $C_{29}H_{34}N_2O_4$: C, 73.39; H, 7.22; N, 5.90 Found: C, 73.16; H, 7.20; N, 5.78

EXAMPLE 8

2-[[2-[4-[[(4-Cyclohexylbutyl)amino]carbonyl]-2-oxazolyl]phenyl]methyl]benzeneacetic acid A. 2-(2-Bromophenyl)-1-ethanol To a solution of 50.0 g (232 mmol) of 2-bomophenylacetic acid in 500 mL of dry tetrahydrofuran (distilled from potassium/benzophenone), cooled to 0°, was added dropwise over 1.5 hours 302 mL (302 mmol, 1M/tetrahydrofuran) of borane-tetrahydrofuran solution. The reaction was stirred for 16 hours at room temperature, was cooled to 0°, and an additional portion of 50 mL (50 mmol) of borane-tetrahydrofuran solution was added dropwise over 45 minutes. The reaction was stirred for 16 hours at room temperature, then recooled to 0° and quenched by the dropwise addition of 50 mL methanol. The reaction mixture was concentrated in vacuo and azeotroped with two 50-mL portions of methanol to give a yellow liquid. The crude liquid was flash-chromatographed (Merck silica, 100× 300 mm, 3:7 ethyl acetate/hexane) to give 46.7 g (232 mmol, 100%) of alcohol A as a clear oil.

B. 1-Bromo-2-[2-[[dimethyl(1,1,2-trimethyl-propyl)silyl] oxy]ethyl]benzene

To a solution of 46.7 g (232 mmol) of crude alcohol A, 34.4 mL (246 mmol, distilled from calcium hydride) of triethylamine and 45.7 g (232 mmol) of thexyldimethylsilyl chloride in 300 mL dry methylene chloride (distilled from phosphorus pentoxide) was added 341 mg (2.79 mmol) of 4-dimethylaminopyridine. The reaction was stirred at room temperature for 48 hours, then diluted with 200 mL hexane and cooled to 0° for 2 hours. The resulting slurry was filtered; the filtrate was concentrated in vacuo to give a crude brown liquid. The crude liquid was flash-chromatographed (Merck silica, 100×300 mm, 1:99 ethyl acetate/hexane) to give 72.8 g (212 mmol, 91%) of silyl ether B as a colorless liquid.

C. 2-[[2-[[[(1,1-Dimethylethyl)diphenylsilyl]-oxy] methyl]phenyl]methyl]benzenacetic acid, methyl ester To a mixture of 599 mg (24.6 mmol) of freshly hammer-crushed magnesium turnings in 15 mL of dry tetrahydrofuran (distilled from sodium/benzophenone) was added a small crystal of iodine followed by 60 µL of 1,2-dibromoethane. The reaction started after heating to 70° C. (oil bath). After 5 minutes of refluxing, about a 20% portion of the required 7.06 g (20.5 mmol) of bromide B was added. An exothermic reaction started with continous heating (70° C.); after the reaction color became clear, the remaining bromide was added in one portion. The reaction mixture was refluxed for 2.5 hours at 70° C., then the gray solution was cooled to room temperature and 15 mL of tetrahydrofuran was added to insure solubility of the Grignard reagent. The resulting solution was added dropwise over 20 minutes to a solution of 10.0 g (20.5 mmol) of iodide G from Example 5 and 2.1 mL (0.1M in tetrahydrofuran, 0.21 mmol) of freshly prepared dilithium tetrachlorocuprate solution (Example 5, Part H) in 25 mL of dry tetrahydrofuran stirred at 0° C. The reaction temperature was maintained below 10° C. during the addition. The reaction mixture was stirred for an additional 2 hours, then partitioned between 240 mL of saturated aqueous ammonium chloride solution/100 mL ether. The organic layer was separated, washed with 100 mL of brine, dried (magnesium sulfate) and concentrated in vacuo to give a crude yellow oil.

To a solution of this crude oil in 130 mL of reagent acetone, cooled to 0° C., was added dropwise 20 mL of Jones reagent (2.6M in Cr$^{+6}$). The reaction mixture was stirred for 2 hours, and then the excess reagent was quenched by addition of 30 mL of isopropanol and stirred for an additional 30 minutes. The resulting green slurry was filtered through Celite®. The filtrate was concentrated in vacuo to give a yellow oil. The oil was dissolved in 150 mL of ether, then washed with two 150-mL portions of 5% aqueous sodium bisulfate solution, followed by 50 mL of brine. The resulting solution of the crude acid was cooled to 0° C. and treated with excess ethereal diazomethane (prepared from 25 g of N-methyl-N'-nitro-N-nitrosoguanidine). After 10 minutes, the excess diazomethane was quenched by the addition of glacial acetic acid, and the solution was concentrated in vacuo to give a crude oil. The crude oil was flash-chromatographed (Merck silica, 100×250 mm, 1:9 ether/hexane) to give 6.78 g (13.3 mmol, 65%) of silyl ether C as a beige, clear oil.

D. 2-[[2-(Hydroxymethyl)phenyl]methyl]benzeneacetic acid, methyl ester

To a solution of 6.78 g (13.3 mmol), of silyl ether C in 40 mL of tetrahydrofuran (distilled from potassium/ benzophenone), cooled to 0° C., was added dropwise over 15 minutes 15 mL (15 mmol, 1M/tetrahydrofuran, Aldrich) of tetra-n-butylammonium fluoride solution. The reaction was stirred at room temperature for 5 hours, and then the mixture was partitioned between 150 mL ethyl acetate/150 mL 1M hydrochloric acid. The aqueous layer was separated and extracted with two 100-mL portions of ethyl acetate. The combined ethyl acetate layers were dried (magnesium sulfate) and concentrated in vacuo to give a crude yellow oil. The crude oil was flash-chromatographed (Merck silica, 50×200 mm, 1:2 ethyl acetate/hexane) to give 3.02 g (11.2 mmol, 84%) of alcohol D as a colorless oil.

E. 2-[(2-Carboxyphenyl)methyl]benzeneacetic acid, methyl ester

To a solution of 1.65 g (5.82 mmol) of alcohol D in 60 mL of reagent acetone, cooled to 0° C., was added dropwise over 20 minutes 22 mL (2.6M in Cr$^{+6}$) of Jones reagent. The reaction was stirred at room temperature for 2 hours then the excess was quenched by the addition of 25 mL isopropanol. The mixture was stirred for 40 minutes, then filtered through Celite®. The filtrate was partitioned between 150 mL 1M hydrochloric acid/150 mL ethyl acetate; the aqueous layer was separated and extracted with two 60-mL portions of ethyl acetate. The combined ethyl acetate layers were dried (magnesium sulfate) and concentrated in vacuo to give a crude solid. The crude solid was flash-chromatographed (Merck silica, 50×150 mm, 1:1 ethyl acetate/hexane) to give 2.46 g (8.65 mmol, 77%) of acid E as a white solid
Melting point 121°–123° C.

F. 2-[[2-[[[2-[(4-Cyclohexylbutyl)amino]-1-(hydroxymethyl)-2-oxoethyl]amino]carbonyl]-phenyl] methyl]benzeneacetic acid, methyl ester To a solution of 1.20 g (4.22 mmol) of acid E in 20 mL of sieve-dried dimethylformamide, cooled to 0° C., was added 1.18 g (4.22 mmol) of L-serine amine hydrochloride M from Example 5, 749 mg (4.43 mmol, 80%,) of 1-hydroxybenzotriazole hydrate and 1.29 mL (9.28 mmol, distilled from calcium hydride) of triethylamine. The mixture was stirred for 5 minutes at 0° C., then 849 mg (4.43 mmol) of 1-(3-dimethylaminopropyl)-3-ethylcarbodiimide hydrochloride (WSC) was added. The reaction mixture was warmed to room temperature and stirred for 16 hours then partitioned between 100 mL ethyl acetate/100 mL 1M hydrochloric acid. The aqueous layer was separated and extracted with two 50-mL portions of ethyl acetate. The combined ethyl acetate layers were washed with two 100-mL portions of water, dried (magnesium sulfate) and concentrated in vacuo to give a crude solid. The solid was flash-chromatographed (Merck silica, 50×120 mm, methylene chloride load, ethyl acetate elution) to give 1.81 g (3.56 mmol, 84%) of amide F as a white solid.

G. 2-[[2-[4-[[(4-Cyclohexylbutyl)amino]-carbonyl]-4,5-dihydro-2-oxazolyl]phenyl]-methyl]benzeneacetic acid, methyl ester A solution of 1.79 g (3.52 mmol) of amide F, 1.38 g (5.28 mmol) of triphenylphosphine and 1.16 mL (6.69 mmol) of diisopropylethylamine in 18 mL sieve-dried acetonitrile/6 mL methylene chloride (distilled from phosphorus pentoxide) was stirred at room temperature until homogeneous. To the reaction mixture was added in one portion 510 µL (5.28 mmol) of carbon tetrachloride. The reaction was stirred at room temperature for 48 hours, then the reaction mixture was partitioned between 80 mL ethyl acetate/100 mL saturated sodium bicarbonate solution. The aqueous layer was separated and extracted with two 40-mL portions of ethyl acetate. The combined ethyl acetate layers were washed with 100 mL water, followed by 50 mL of brine, dried (magnesium sulfate) and concentrated in vacuo to give a crude orange oil. The crude oil was flash-chromatographed (Merck silica, 50×120 mm, 2:1 ethyl acetate/hexane) to give 1.67 g (3.42 mmol, 97%) of oxazoline G as a pale orange oil.

H. 2-[[2-[4-[[(4-Cyclohexylbutyl)amino]-carbonyl]-2-oxazolyl]phenyl]methyl]-benzeneacetic acid, methyl ester To a solution of 2.04 mL (13.7 mmol, Aldrich) of 1,8-diazabicyclo[5.4.0]undec-7-ene in 12 mL ethyl acetate was added 1.53 g (6.84 mmol) of cupric bromide. The mixture was stirred for 10 minutes at room temperature, then placed in an ambient water bath. A solution of 1.67 g (3.42 mmol) of oxazoline G in 12 mL chloroform was added dropwise over 10 minutes to the reaction mixture. The reaction was slightly exothermic. The reaction was stirred for 16 hours at room temperature, and then a second portion of cupric bromide (1.53 g, 6.84 mmol) was added; after 18 hours, a third portion (1.53 g, 6.84 mmol) was added. The reaction was stirred an additional 16 hours at room temperature, then partitioned between 150 mL 2:1 (saturated ammonium chloride solution/concentrated ammonium hydroxide)/100 mL ethyl acetate. The aqueous layer was separated and extracted with two 50-mL portions of ethyl acetate. The combined ethyl acetate layers were dried (magnesium sulfate) and concentrated in vacuo to give a crude oil. The crude oil was flash-chromatographed (Merck silica, 50×150 mm, 1:5 ethyl acetate/hexane, then 1:3 ethyl acetate/hexane) to give 720 mg (1.48 mmol, 43%) of oxazole-ester H as a yellow oil.

I. 2-[[2-[4-[[(4-Cyclohexylbutyl)amino]-carbonyl]-2-oxazolyl]phenyl]methyl]benzeneacetic acid To a solution of 720 mg (1.48 mmol) of ester H in 12 mL distilled tetrahydrofuran/3 mL water, stirred at room temperature, was added 124 mg (2.95 mmol, Aldrich) of lithium hydroxide monohydrate. The reaction was stirred vigorously for 5 hours at room temperature, then quenched by the addition of 6 mL (6 mmol) of 1M hydrochloric acid. The mixture was partitioned between 40 mL ethyl acetate/40 mL water; the aqueous layer was separated and extracted with two 20-mL portions of ethyl acetate. The combined ethyl acetate layers were washed with 40 mL brine, dried (magnesium sulfate) and concentrated in vacuo to give a crude yellow solid. The crude solid was recrystallized from hot ethyl acetate/hexane to give 451 mg (0.95 mmol, 64%) of Example 8 as a white solid.

Melting point 137°–139° C.
IR (KBr): 3354,3061,2920,2849,1723,1636,1603,1526 $cm^{-1}$.
MS(CI): 475 $(M+H)^+$.
TLC: $R_f$(silica gel, 1:9 methanol/methylene chloride)=0.70, ammonium molybdate/ceric sulfate and UV, homogeneous.
Analysis Calc'd for $C_{29}H_{34}N_2O_4$: C, 73.39; H, 7.22; N, 5.90
Found: C, 73.16; H, 7.20; N, 5.78

EXAMPLE 9

3-[[2-[4-[[(4-Cyclohexylbutyl)amino]carbonyl]-2-oxazolyl]phenyl]methyl]benzenepropanoic acid A. 3-Bromocinnamic acid, methyl ester To a solution of 50.0 g (220 mmol, Aldrich) of 3-bromocinnamic acid in 1 L sieve-dried methanol (Burdick & Jackson), stirred at 0° C., was added dropwise a solution of acidic methanol (prepared by the addition of 2.5 mL acetyl chloride to 250 mL methanol). The reaction mixture was stirred at room temperature for 96 hours then concentrated in vacuo to give a crude green oil. The crude oil was flash-chromatographed (Merck silica, 100×200 mm, 1:1 ethyl acetate/hexane) to give 51.2 g (212 mmol, 96%) of ester A as a white solid.

B. 3-(3-Bromophenyl)propanoic acid, methyl ester

To a slurry of 9.84 g of 5% rhodium on alumina catalyst (20% by weight, Aldrich) in 50 mL sieve-dried methanol, purged with argon for 15 minutes, was added a solution of 49.2 g (204 mmol) of ester A in 100 mL sieve-dried methanol. The reaction flask was evacuated and filled with hydrogen three times, and then the reaction was stirred under hydrogen (balloon) for 80 hour The reaction mixture was filtered through a 0.4 micron polycarbonate filter. The filtrate was concentrated in vacuo to give a crude orange liquid. The crude liquid was flash-chromatographed (Merck silica, 100× 400 mm, 2:98 ethyl acetate/hexane) to give 46.5 g (191 mmol, 94%) of ester B as a yellow liquid.

C. 3-(3-Bromophenyl)-1-propanol

To a solution of 46.5 g (191 mmol) of ester B in 200 mL sieve-dried toluene (Burdick & Jackson), cooled to 0° C., was added dropwise over 1.5 hours 281 mL (421 mmol, 1.5M/toluene, Aldrich) of diisobutylaluminum hydride solution. The reaction was stirred at 0° C. for 16 hours then an additional portion of 64 mL (96 mmol) of diisobutylaluminum hydride solution was added dropwise over 45 minutes. The reaction was stirred at 0° C. for 1 hour, then quenched by the dropwise addition of 10 mL methanol. The reaction mixture was added slowly to 500 mL ice-cold 6M aqueous hydrochloric acid solution over 40 minutes. The mixture was stirred at 0° C. for 1 hour and then extracted with three 150-mL portions of ether. The combined ether layers were washed with three 250-mL portions of 1M sodium hydroxide, 200 mL brine, dried (magnesium sulfate) and concentrated in vacuo to give 40.5 g (188 mmol, 98%) of alcohol C as a clear oil.

D. 1-Bromo-3-[3-[[dimethyl(1,1,2-trimethyl-propyl)silyl]oxy]propyl]benzene

To a solution of 40.5 g (188 mmol) of crude alcohol C, 27.8 mL (199 mmol, distilled from calcium hydride) of triethylamine and 33.7 g (188 mmol, Petrarch) of thexyldimethylsilyl chloride in 300 mL dry dichloromethane (distilled from phosphorus pentoxide) was added 276 mg (2.26 mmol, Aldrich) of 4-dimethylaminopyridine. The reaction was stirred at room temperature for 48 hours then diluted with 400 mL hexane and cooled to 0° C. for 2 hours. The resulting slurry was filtered; the filtrate was concentrated in vacuo to give a crude brown liquid. The crude liquid was flash-chromatographed (Merck silica, 100×250 mm, 1% ethyl acetate/hexane) to give 60.3 g (169 mmol, 90%) of silyl ether D as a colorless liquid.

E. 3-[[2-[[[(1,1-Dimethylethyl)diphenylsilyl]-oxy]methyl]phenyl]methyl]benzenepropanoic acid, methyl ester To a mixture of 599 mg (24.6 mmol) of freshly hammer-crushed magnesium turnings in 15 mL dry tetrahydrofuran (distilled from sodium/benzophenone) was added a small crystal of iodine followed by 60 µL of 1,2-dibromoethane. The reaction started after heating to 70° C. (oil bath). After 5 minutes of refluxing, about a 20% portion of the required 7.34 g (20.5 mmol) of silyl ether D was added. An exothermic reaction started with continous heating (70° C.); after the reaction color became clear, the remaining silyl ether was added in one portion. The reaction mixture was refluxed for 2.5 hours at 70° C., and then the gray solution was cooled to room temperature and 15 mL of tetrahydrofuran was added to insure solubility of the Grignard reagent. The resulting solution was added dropwise over 20 minutes to a solution of 10.0 g (20.5 mmol) of iodide G from Example 5 and 2.1 mL (0.1M in tetrahydrofuran, 0.21 mmol) of freshly prepared dilithium tetrachlorocuprate solution (Example 5, Part H) in 75 mL of dry tetrahydrofuran stirred at 0° C. The reaction temperature was maintained below 10° C. during the addition. The reaction mixture was stirred for an additional 2 hours, then partitioned between 240 mL of saturated aqueous ammonium chloride solution/100 mL ether. The organic layer was separated, washed with 100 mL of brine, dried (magnesium sulfate) and concentrated in vacuo to give a crude yellow oil.

To a solution of crude oil in 130 mL of reagent acetone, cooled to 0° C., was added dropwise 20 mL of Jones reagent (2.6M in $Cr_{+6}$). The reaction mixture was stirred for 2 hours, and then the excess reagent was quenched by addition of 10 mL of isopropanol and stirred for an additional 30 minutes. The resulting green slurry was filtered through Celite®. The filtrate was concentrated in vacuo to give a yellow oil. The oil was dissolved in 150 mL of ether, then washed with two 150-mL portions of 5% aqueous sodium bisulfate solution, followed by 50 mL of brine. The resulting solution of the crude acid was cooled to 0° C. and treated with excess ethereal diazomethane (prepared from 25 g of N-methyl-N'-nitro-N-nitrosoguanidine). After 10 minutes, the excess diazomethane was quenched by the addition of glacial acetic acid and the solution was concentrated in vacuo to give an oil. The crude oil was flash-chromatographed (Merck silica, 100×250 mm, 1:9 ether/hexane) to give 4.86 g (9.29 mmol, 45%) of silyl ether E as a yellow oil.

F. 3-[[2-(Hydroxymethyl)phenyl]methyl]benzeneacetic acid, methyl ester

To a solution of 4.86 g (9.29 mmol) of silyl ether E in 20 mL tetrahydrofuran (distilled from potassium, benzophenone), cooled to 0° C., was added dropwise over 15 minutes 10.2 mL (10.2 mmol, 1M/tetrahydrofuran, Aldrich) of tetra-n-butylammonium fluoride solution. The reaction was stirred at room temperature for 16 hours then the mixture was partitioned between 100 mL ethyl acetate/125 mL water. The aqueous layer was separated and extracted with two 50-mL portions of ethyl acetate. The combined ethyl acetate layers were dried (magnesium sulfate) and concentrated in vacuo to give a crude yellow oil. The crude oil was flash-chromatographed (Merck silica, 50×200 mm, 1:2 ethyl acetate/hexane) to give 1.65 g (5.81 mmol, 63%) of alcohol F as a clear oil.

G. 3-[(2-Carboxyphenyl)methyl]benzeneacetic acid, methyl ester

To a solution of 1.65 g (5.82 mmol) of alcohol F in 30 mL reagent acetone (Mallinckrodt), cooled to 0° C., was added dropwise over 20 minutes 11 mL (2.6M in $Cr^{+6}$) of Jones reagent. The reaction was stirred room temperature for 2 hours, and then the excess was quenched by the addition of 10 mL isopropanol. The mixture was stirred for 30 minutes, then filtered through Celite®. The filtrate was partitioned between 60 mL 1M aqueous hydrochloric acid/80 mL warm ethyl acetate; the aqueous layer was separated and extracted with two 40-mL portions of ethyl acetate. The combined ethyl acetate layers were washed with 100 mL brine, dried (magnesium sulfate) and concentrated in vacuo to give a crude beige solid. The crude solid was flash chromatographed (Merck silica, 50×100 mm, 1% acetic acid/(1:1 ethyl acetate/hexane)) to give 1.64 g (5.49 mmol, 95%) of acid G as a beige solid Melting point 67°–70° C.

H. 3-[[2-[[[2-[(4-Cyclohexylbutyl)amino]-1-(hydroxymethyl)-2-oxoethyl]amino]carbonyl]-phenyl]methyl]benzenepropanoic acid, methyl ester To a solution of 820 mg (2.75 mmol) of acid G in 20 mL sieve-dried dimethylformamide (Burdick & Jackson), cooled to 0° C., was added 765 mg (2.75 mmol) of L-serine amide hydrochloride M from Example 5, 488 mg (2.89 mmol, 80%,) of 1-hydroxybenzotriazole hydrate and 850 µL (6.1 mmol, distilled from calcium hydride) of triethylamine. The mixture was stirred 5 minutes at 0° C., then 553 mg (2.89 mmol) of 1-(3-dimethylaminopropyl)-3-ethylcarbodiimide hydrochloride (WSC) was added. The reaction mixture was warmed to room temperature and stirred for 16 hours then partitioned between 50 mL ethyl acetate/100 mL 1M aqueous hydrochloric acid. The aqueous layer was separated and extracted with two 30-mL portions of ethyl acetate. The combined ethyl acetate layers were washed with two 100-mL portions of water, dried (magnesium sulfate) and concentrated in vacuo to give a crude solid. The solid was flash-chromatographed (Merck silica, 50×120 mm, methylene chloride load, ethyl acetate elution) to give 970 mg (1.86 mmol, 67%) of amide H as a white solid.

I. 3-[[2-[4-[[(4-Cyclohexylbutyl)amino]-carbonyl]-4,5-dihydro-2-oxazolyl]phenyl]-methyl]benzenepropanoic acid, methyl ester A solution of 958 mg (1.83 mmol) of amide H, 721 mg (2.75 mmol, Aldrich) of triphenylphosphine and 610 µL (3.48 mmol) of diisopropylethylamine in 12 mL sieve-dried acetonitrile (Burdick & Jackson)/4 mL methylene chloride (distilled from phosphorus pentoxide) was stirred at room temperature until homogeneous. To the reaction mixture was added in one portion 270 µL (2.75 mmol) of carbon tetrachloride. The reaction was stirred at room temperature for 16 hours then an additional portion of 50 mg (0.19 mmol) of triphenylphosphine was added; the reaction was stirred at room temperature for an additional 48 hour The reaction mixture was partitioned between 80 mL ethyl acetate/100 mL saturated sodium bicarbonate solution; the aqueous layer was separated and extracted with two 40-mL portions of ethyl acetate. The combined ethyl acetate layers were washed with 100 mL water, followed by 50 mL of brine, dried (magnesium sulfate) and concentrated in vacuo to give a crude yellow oil. The crude oil was flash-chromatographed (Merck silica, 50×120 mm, 2:1 ethyl acetate/hexane) to give 809 mg (1.61 mmol, 88%) of oxazoline I as a pale orange oil.

J. 3-[[2-[4-[[(4-Cyclohexylbutyl)amino]-carbonyl]-2-oxazolyl]phenyl]methyl]-benzenepropanoic acid, methyl ester To a solution of 961 μL (6.42 mmol, Aldrich) of 1,8-diazabicyclo[5.4.0]undec-7-ene in 6 mL ethyl acetate (Burdick & Jackson) was added 717 mg (3.21 mmol, Aldrich) of cupric bromide. The mixture was stirred for 10 minutes at room temperature, then cooled in a water bath. A solution of 809 mg (1.61 mmol) of oxazoline I in 6 mL chloroform (Burdick & Jackson) was added dropwise over 10 minutes to the reaction mixture. The reaction was slightly exothermic. The reaction was stirred for 16 hours at room temperature, and then a second portion of 717 mg (3.21 mmol) of cupric bromide was added; after 18 hours, a third portion of 717 mg (3.21 mmol) was added. The reaction was stirred an additional 16 hours at room temperature, then partitioned between 150 mL 2:1 (saturated ammonium chloride solution/concentrated ammonium hydroxide/100 mL ethyl acetate. The aqueous layer was separated and extracted with two 50-mL portions of ethyl acetate. The combined ethyl acetate layers were dried (magnesium sulfate) and concentrated in vacuo to give a crude oil. The crude oil was flash-chromatographed (Merck silica, 50×150 mm, 1:5 ethyl acetate/hexane, then 1:3 ethyl acetate/hexane) to give 367 mg (0.73 mmol, 45%) of oxazole J as a white solid
Melting point 73°–75° C.

K. 3-[[2-[4-[[(4-Cyclohexylbutyl)amino]-carbonyl]-2-oxazolyl]phenyl]methyl]-benzenepropanoic acid To a solution of 353 mg (0.70 mmol) of oxazole J in 6 mL distilled tetrahydrofuran/1.5 mL water, stirred at room temperature, was added 59 mg (1.4 mmol, Aldrich) of lithium hydroxide monohydrate. The reaction was stirred vigorously for 5 hours at room temperature, then quenched by the addition of 3 mL (3 mmol) of 1M aqueous hydrochloric acid. The mixture was partitioned between 30 mL ethyl acetate/30 mL water; the aqueous layer was separated and extracted with two 20-mL portions of ethyl acetate. The combined ethyl acetate layers were washed with 30 mL brine, dried (magnesium sulfate) and concentrated in vacuo to give a crude white foam. The crude foam was recrystallized from hot ethyl acetate/hexane to give 302 mg (0.62 mmol, 89%) of Example 9 as a white solid.
Melting point 124°–126° C.
IR (KBr): 3350,3124,2920,2850,1705,1653,1595,1516 cm$^{-1}$.
TLC: R$_f$(silica gel, 1:9 methanol/methylene chloride)=0.58, ammonium molybdate/ceric sulfate and UV, homogeneous.
Analysis Calc'd for $C_{30}H_{36}N_2O_4$: C, 73.74; H, 7.43; N, 5.73
Found: C, 73.79; H, 7.42; N, 5.79

EXAMPLE 10

(Z)-2-[3-[[[2-(4-Chlorophenyl)ethyl]amino]-carbonyl]-2-oxazolyl]-2-methyl-2-butenyl]-benzenepropanoic acid A. 2,3-Dimethylbut-2-ene-1,4-diol A solution of 2,3-dimethylmaleic anhydride (6.3 g, 50 mmol) in dry tetrahydrofuran (25 mL) was added dropwise to a stirred suspension of lithium aluminum hydride (3.8 g, 100 mmol) in tetrahydrofuran (50 mL) at 0° C. The suspension was warmed to room temperature and stirred for 3 hours. Excess lithium aluminum hydride was destroyed by careful addition of freshly prepared saturated sodium sulfate solution in water at 0° C. Addition was continued until all inorganics were precipitated as white solids. Anhydrous magnesium sulfate was added and the mixture was filtered. The filtrate was concentrated under reduced pressure to obtain diol A (4.5 g, 78%) as a colorless oil.

B. 2,3-Dimethyl-but-2-ene-1,4-diacetate

A stirred solution of diol A (4.5 g, 38.8 mmol), pyridine (10 mL) in dichloromethane (25 mL) was treated with dimethylaminopyridine (122 mg, 1 mmol) and acetic anhydride (10.2 g, 100 mmol). After 3 hours the mixture was diluted with ether (200 mL) and washed with saturated copper sulfate solution (4x), water, dried (magnesium sulfate), filtered and concentrated. The residue was chromatographed on a silica gel column and eluted with 5–10% ethyl acetate in hexanes to obtain diacetate B (4.85 g, 63%) as a colorless oil.

C. (Z)-2-[3-(Acetoxymethyl)-2-methyl-2-butenyl]-benzenepropanol, dimethylthexylsilyl ether A suspension of magnesium turnings (576 mg, 24 mmol) and catalytic iodine in anhydrous tetrahydrofuran (10 mL) was heated under reflux. A few drops of [3-(2-bromophenyl)]-propanol,dimethylthexylsilyl ether was added to initiate the formation of Grignard reagent. Once the iodine color was discharged, additional bromide (a total of 4 g, 12.16 mmol) was added in one portion. The mixture was heated under reflux for 1 hour, cooled to 0° C. in an ice-water bath and was then added via cannula to a solution of diacetate B (1.8 g, 9 mmol) and a 0.1M solution of dilithiumcopper tetrachloride (1 mL) in tetrahydrofuran (10 mL) at –78° C. The mixture was stirred at –78° C. for 45 minutes and at 0° C. for 1.5 hours quenched with saturated ammonium chloride solution. It was diluted with ether (150 mL) and water (50 mL). The ether extract was separated, dried (MgSO$_4$), filtered and concentrated. The residue was chromatographed on a silica gel column and eluted with 1% and 1.5% ethyl acetate in hexanes to obtain acetate/protected alcohol C (3.05 g, 81%) as a colorless oil.

D. (Z)-2-[3-(Hydroxymethyl)-2-methyl-2-butenyl]-benzenepropanoic acid, methyl ester A solution of acetate/protected alcohol C (3.05 g, 7.3 mmol) in acetone (25 mL) was treated dropwise at 0°–5° C. with a 2.67M solution of Jones reagent in acetone (7 mL). After 30 minutes, the mixture was warmed to room temperatureand stirred for 2 hour Excess Jones reagent was destroyed by addition of isopropanol (6 mL) at 0°–5° C. The mixture was diluted with ethyl acetate (100 mL) and water (50 mL). The ethyl acetate layer was separated and the aqueous layer was extracted with ethyl acetate (50 mL). The ethyl acetate extracts were combined, dried (magnesium sulfate), filtered and concentrated under reduced pressure to obtain a yellow oil, which was dissolved in ether (100 mL), cooled to 0°–5° C. and treated with excess of an etheral diazomethane solution. After 30 minutes, excess diazomethane was removed by bubbling argon through the reaction mixture. The mixture was concentrated under reduced pressure, and the residue was chromatographed on a silica gel column. Elution with 5% and 7% ethyl acetate in hexanes afforded ester D (1.63 g, 73%) as a colorless oil.

E. (Z)-2-[3-(Hydroxymethyl)-2-methyl-2-butenyl]-benzenepropanoic acid, methyl ester Powdered potassium carbonate (276 mg, 2 mmol) was added to a stirred solution of acetate-ester D (1.63 g, 5.36 mmol) in methanol (25 mL) at 0°–5° C. The mixture was stirred at 0° C. to room temperaturefor 6 hours diluted with ether (150 mL) and water (50 mL). The ether extract was separated, dried (magnesium sulfate), filtered and concentrated under reduced pressure to obtain an oil, which was chromatographed on a silica gel column and eluted with 5–20% ethyl acetate in hexanes to obtain alcohol-ester E (1.09 g, 78%) as an oil.

F. (Z)-2-[3-Formyl-2-methyl-2-butenyl]-benzenepropanoic acid, methyl ester

Activated manganese dioxide (1 g) was added to a stirred solution of alcohol-ester E (1 g, 3.29 mmol) in hexanes (50 mL). Additional 1 g portions of manganese dioxide were added at one-hour intervals (9 g total). The suspension was stirred overnight and then filtered through a pad of anhydrous magnesium sulfate. The residual solid was washed with ether (25 mL,5x). The filtrate was concentrated to obtain aldehyde-ester F (780 mg, 78%) as an oil.

G. (Z)-2-[3-Carboxy-2-methyl-2-butenyl]-benzenepropanoic acid, methyl ester

A solution of potassium dihydrogen phosphate (3 g, 22 mmol) and sodium chlorite (2.5 g, 27.5 mmol) in water (25 mL) was added dropwise to a stirred solution of aldehyde-ester F (780 mg, 2.58 mmol) and 2-methyl-2-butene (15 mL) in t-butanol (40 mL). The biphasic reaction mixture was stirred at room temperature overnight. Most of the butanol was removed by concentration under reduced pressure. The residue was diluted with water and extracted with ether (50 mL,3x). The ether extracts were combined, washed with 1N aqueous hydrochloric acid solution (30 mL), water (30 mL), dried (magnesium sulfate), filtered and concentrated to obtain acid-ester G (870 mg, contained some t-butanol) as an oil.

H. (Z)-2-[3-[[[2-[[2-(4-Chlorophenyl)ethyl]-amino]-1-(hydroxymethyl)-2-oxoethyl]amino]-carbonyl]-2-methyl-2-butenyl]benzenepropanoic acid, methyl ester A solution of acid-ester G (870 mg crude, about 2.58 mmol), N-hydroxybenztriazole (1.12 g, 8.34 mmol) and (2-p-chlorophenylethylamido)-S-serine hydrochloride (1.4 g, 5.02 mmol) in dimethylformamide (40 mL) was stirred at 0°–5° C. After a few minutes, triethylamine (2.5 g, 25 mmol) was added dropwise. After 30 minutes, 1-(3-dimethylaminopropyl)-3-ethylcarbodiimide hydrochloride (1.26 g, 6.6 mmol) was added. The mixture was stirred at 0° C. to room temperature for 22 hours diluted with water (100 mL) and extracted with ether (100 mL,2x). The ether extract was washed with 1N aqueous hydrochloric acid solution (50 mL), dried (magnesium sulfate), filtered and concentrated. The residue was chromatographed on a silica gel column and eluted with 20–75% ethyl acetate in hexanes, followed by ethyl acetate and 2% methanol in ethyl acetate to obtain diamide H (1 g, 78% from F).

I. (Z)-2-[3-[[[2-(4-Chlorophenyl)ethyl]amino]-carbonyl]-4,5-dihydro-2-oxazolyl]-2-methyl-2-butenyl]-benzenepropanoic acid, methyl ester Triphenylphosphine (1.96 g, 7.38 mmol) was added to a stirred solution of diamide H (900 mg, 1.8 mmol) in acetonitrile (25 mL). After a few minutes, N,N-diisopropylethylamine (1.3 mL, 7.56 mmol) was added. Addition of carbon tetrachloride (2.5 mL) followed. The mixture was stirred for 3 hours diluted with ethyl acetate (150 mL) and washed with 5% aqueous sodium bicarbonate solution (50 mL) and brine (50 mL). The organic extract was dried (magnesium sulfate), filtered and concentrated. The residue was chromatographed on a silica gel column and eluted with 20–40% ethyl acetate in hexanes to obtain oxazoline I (780 mg, 90%) as a light yellow oil.

J. (Z)-2-[3-[[[2-(4-Chlorophenyl)ethyl]amino]-carbonyl]-2-oxazolyl]-2-methyl-2-butenyl]-benzenepropanoic acid Nickel peroxide (350 mg) was added to a stirred solution of oxazoline I (430 mg, 0.89 mmol) in dry methylene chloride (15 mL). The mixture was stirred vigorously at room temperature under an argon atmosphere. Additional nickel peroxide (a total of 1.1 g) was added in 250 mg portions every hour. After 4 hours the mixture was diluted with ethyl acetate (150 mL) and washed with a 3M solution of sodium bisulfite (50 mL). The ethyl acetate layer was separated, washed with 1M trisodium citrate solution (50 mL, 2x) and brine (50 mL). The organic layer was dried (magnesium sulfate), filtered and concentrated. The crude residue was chromatographed on a silica gel column and eluted with 10–20% ethyl acetate in hexanes to afford ester J (220 mg, 51%) as a white solid.

K. (Z)-2-[3-[[[2-(4-Chlorophenyl)ethyl]amino]-carbonyl]-2-oxazolyl]-2-methyl-2-butenyl]-benzenepropanoic acid A solution of lithium hydroxide (246 mg, 6 mmol) in water (6 mL) was added to a stirred solution of ester J. (200 mg, 0.42 mmol) in distilled tetrahydrofuran (20 mL). After 24 hours the mixture was diluted with ether (150 mL) and washed with 1N hydrochloric acid solution (50 mL, twice). The ether extract were dried (magnesium sulfate), filtered and concentrated under reduced pressure and in vacuo to obtain Example 10 (157 mg, 81%) as a white solid Melting point 155°–158° C.

EXAMPLE 11

2-[[2-[4-[[[2-(4-Chlorophenyl)ethyl]amino]-carbonyl]-2-oxazolyl]-1-cyclohexenyl]methyl]-benzenepropanoic acid A. 4,5,6,7-Tetrahydro-1(3H)-isobenzofuranone To a stirred mixture of 4,5,6,7-Tetrahydro-1,3-isobenzofurandione (12.0 g, 78.9 mmol) in 200 mL of dry tetrahydrofuran under argon at 0° C. was added sodium borohydride (4.48 g, 118 mmol). The mixture was stirred at 0° C. for 5.5 hours and poured into a 400-mL ice-water mixture. The mixture was neutralized to pH 7 by the addition of 16N hydrochloric acid solution. The mixture was concentrated in vacuo to remove tetrahydrofuran. The mixture was then acidified to pH 1 by the addition of 1N hydrochloric acid solution. The mixture was extracted with ether (3×400 mL) and then with dichloromethane (1×400 mL). The combined organic extracts were dried (magnesium sulfate), filtered and concentrated in vacuo to give 9 g (83%) of lactone A.

TLC: silica gel, 2% methanol/dichloromethane.
$R_f$ 0.48, $I_2$.

B. 1-Cyclohexene-1,2-dimethanol

To a stirred mixture of lactone A (8.90 g, 64.5 mmol) in 200 mL of dry tetrahydrofuran under argon at 0° C. was added a 1.5M solution of diisobutylaluminum hydride in toluene (107 mL, 161 mmol) over 15 minutes. The mixture was stirred for 20 hours at room temperature and quenched slowly at 0° C. under argon with 30 mL of acetone. The mixture was diluted with 200 mL of acetone. To this well-stirred mixture was added slowly 140 g of 10:9 silica gel-water. The addition took 30 minutes on this scale. The mixture was stirred at room temperature for 30 minutes and the solid was filtered off. The solid was rinsed with acetone (4×300 mL). The filtrate was concentrated in vacuo to give 9.15 g of diol B in a quantitative yield.

TLC: silica gel, 2% methanol/dichloromethane.
$R_f$ 0.18, iodine.

C. 2-[[[(1,1-Dimethylethyl)diphenylsilyl]oxy]-methyl]-1-cyclohexene-1-methanol To a stirred mixture of 60% sodium hydride in mineral oil (12.5 g, 62.8 mmol, washed with hexane) in 100 mL of dry tetrahydrofuran under argon at 0° C. was added a solution of diol B (9.10 g, 64.1 mmol) over 20 minutes. The mixture was heated at 50° C. for one hour and then stirred at room temperature for 16 hours. To this stirred mixture at 0° C. under argon was added diphenyl-t-butylsilyl chloride (16.7 mL, 64.1 mmol). The mixture was stirred at room temperature for 3 hours and quenched slowly with 20 mL of saturated ammonium chloride solution. The mixture was concentratated in vacuo. The residue was partitioned between 200 mL of 1N hydrochloric acid solution and ether (4×200 mL). The ether extracts were dried (magnesium sulfate), filtered and concentrated in vacuo. Purification was effected by flash chromatography on 180 g of Merck silica gel 60 using 10:1 hexane-ether as eluant to give 13.2 g (54%) of silyl ether C.

TLC: silica gel, 10:1 hexane-ether, $R_f$ 0.20, $I_2$.

D. 2-[[[(1,1-Dimethylethyl)diphenylsilyl]oxy]-methyl]-1-cyclohexene-1-methanol, acetate ester To a stirred mixture of silyl ether C (5.53 g, 14.6 mmol) in pyridine (3.53 mL, 43.7 mmol) at 0° C. under argon was added acetic anhydride (2.06 mL, 21.8 mmol). The mixture was stirred at room temperature for 18 hours and diluted with 400 mL of ether. The mixture was washed with 1N hydrochloric acid solution (3×100 mL), saturated sodium bicarbonate solution (2×100 mL) and brine (1×100 ml). The ether was dried (magnesium sulfate), filtered and concentrated in vacuo to give 5.82 g (95%) of acetate D.

TLC: silica gel, 4:1 hexane-ether.

$R_f$ 0.47, iodine.

E. 1-[[2-[3-[[(1,1-Dimethylethyl)dimethylsilyl]oxy]propyl]phenyl]methyl]-2-[[[(1,1-dimethylethyl)diphenylsilyl]oxy]methyl]-1-cyclohexene To a stirred mixture of magnesium turnings (1.97 g, 80.8 mmol) and a small amount of iodine (a few crystals) in 20 mL of dry tetrahydrofuran under argon at 55° C. was added 5% of a solution of 1-bromo-2-[3-[[(1,1-dimethylethyl)dimethylsilyl]oxy]propyl]benzene (9.62 g, 26.9 mmol) in 20 mL of dry tetrahydrofuran. The iodine color dispatched and the remaining 95% of the bromide solution was added dropwise over 30 min. The mixture was heated at 70° C. for 20 minutes and then cooled to 0° C. To a stirred mixture of acetate D (7.58 g, 18.0 mmol) and 0.1M solution of dilithium copper tetrachloride in tetrahydrofuran (2.69 mL, 0.27 mmol) in 20 mL of tetrahydrofuran under argon at −78° C. was added the above precooled Grignard solution over 30 minutes. The mixture was stirred at −78° C. for 90 minutes, at 0° C. for 3 hours and then at room temperature for 20 hours. The mixture was quenched at 0° C. with argon-purged methanol (5 mL). The mixture was diluted with 300 mL of ether and 150 mL of saturated ammonium chloride solution. The aqueous layer was separated and extracted with ether (2×200 mL). The combined ether extracts were dried (magnesium sulfate), filtered and concentrated in vacuo. This material was chromatographed on 220 g of Merck silica gel 60 using 19:1 hexane-ether as eluant to give 9.2 g of an inseparable mixture of [3-[[(1,1-Dimethylethyl)dimethylsilyl]oxy]propyl]benzene and compound E.

F. 2-[[2-[[[(1,1-Dimethylethyl)diphenylsilyl]-oxy]methyl]-1-cyclohexen-1-yl]methyl]-benzenepropanoic acid, methyl ester To the above mixture containing compound E in 100 mL of acetone under argon in a cold water bath was added Jones reagent (6 mL) until an orange-red color persisted. The mixture was stirred at room temperature for one hour and quenched with isopropyl alcohol (7 mL). The mixture was concentrated in vacuo and partitioned between 160 mL of 3M sodium metabisulfite solution and ethyl acetate (3×200 mL). The ethyl acetate extracts were washed with water (2×100 mL) and brine (1×100 mL). The organic layer was dried (magnesium sulfate), filtered and concentrated in vacuo to give a crude acid. A stirred mixture of this crude acid in 100 mL of ether was treated with etheral diazomethane until a yellow color persisted. The mixture was stirred at room temperature for 30 minutes and the excess diazomethane was destroyed by the addition of acetic acid. The mixture was concentrated in vacuo to give methyl ester F.

G. 2-[[2-(Hydroxymethyl)-l-cyclohexen-1-yl]-methyl]benzenepropanoic acid, methyl ester To a stirred mixture of methyl ester F in 20 mL of dry tetrahydrofuran under argon at room temperature was added a 1M solution of n-tetrabutylammonium fluoride in tetrahydrofuran (20 mL, 20 mmol). The mixture was stirred at room temperature for 3.5 hours and then poured into a mixture of 100 mL of ethyl acetate and 70 mL of saturated ammonium chloride solution. The aqueous layer was separated and extracted with ethyl acetate (3×100 mL). The combined ethyl acetate extracts were dried (magnesium sulfate), filtered and concentrated in vacuo. Purification was effected by flash chromatography on 140 g of Merck silica gel 60 using 1:1 ether-hexane as eluant to give 1.26 g (24%) of alcohol G. TLC: silica gel, 1:1 ether-hexane, $R_f$ 0.28, cerium disulfate.

H. 2-[[2-Formyl-1-cyclohexen-1-yl]methyl]-benzenepropanoic acid, methyl ester To a stirred mixture of alcohol G (110 mg, 0.38 mmol) in 5 mL of dry dichloromethane under argon was added manganese dioxide (460 mg, 5.29 mmol). The mixture was stirred at room temperature for 1 hour, at which time more manganese dioxide (240 mg, 2.76 mmol) was added. The mixture was stirred at room temperature for one hour, and again manganese dioxide (440 mg, 5.06 mmol) was added. The mixture was stirred at room temperature for another 2 hours, and a final batch of manganese dioxide (240 mg, 2.76 mmol) was added. The mixture was stirred at room temperature for 30 minutes and the solid was filtered off. The solid was rinsed with dichloromethane (3×15 mL). The filtrate was concentrated in vacuo to give 106 mg (97%) of aldehyde H.

TLC: silica gel, 1:1 hexane-ether $R_f$ 0.44, cerium disulfate.

I. 2-[[2-Carboxy-1-cyclohexen-1-yl]methyl]-benzenepropanoic acid, methyl ester To a stirred mixture of aldehyde H (618 mg, 2.16 mmol) and 2-methyl-2-butene (10.8 mL, 102 mmol) in 45 mL of t-butanol was added a solution of sodium chlorite (1.80 g, 19.9 mmol) and sodium dihydrogen phosphate (1.8 g, 15.0 mmol) in 18 mL of water over 15 minutes. The mixture was stirred at room temperature for 19 hours and concentrated in vacuo. The residue was diluted with 40 mL of water and extracted with hexane (2×60 mL). The hexane extracts were dried (magnesium sulfate), filtered and concentrated in vacuo. This material was chromatographed on 34 g of Merck silica gel 60 using 0.5% acetic acid in 2% methanol/dichloromethane as eluant to give 544 mg (83%) of acid I.

TLC: silica gel, 1:1 hexane-ether.

$R_f$ 0.28, iodine.

J. 2-[[2-[[[2-[[2-(4-Chlorophenyl)ethyl]-amino]-1-(hydroxymethyl)-2-oxoethyl]amino]-carbonyl]-1-cyclohexenyl]methyl]benzenepropanoic acid, methyl ester To a stirred mixture of acid I (540 mg, 1.79 mmol), 1-hydroxybenzotriazole hydrate (302 mg, 1,79 mmol) and N-[2-(4-Chlorophenyl)ethyl]-L-serinamide hydrochloride (499 mg, 1.79 mmol) in 8 mL of dimethylformamide was added in order triethylamine (0.75 mL, 5.36 mmol) and ethyl-3-(3-dimethylamino)-propylcarbodiimide hydrochloride salt (343 mg, 1.79 mmol). The mixture was stirred at room temperature for 75 hours and concentrated in vacuo. The residue was diluted with 200 mL of ethyl acetate. The mixture was washed with 0.2N sodium hydroxide solution (3×30 mL), 1 N hydrochloric acid solution (3×30 mL), saturated sodium bicarbonate solution (1×30 mL) and brine (1×50 mL). The ethyl acetate layer was dried (magnesium sulfate), filtered and concentrated in vacuo. Purification was effected by flash chromatography on 40 g Merck silica gel 60 using 2% methanol/dichloromethane as eluant to give 653 mg (69%) of amide J.

TLC: silica gel, 4% methanol/dichloromethane.

$R_f$ 0.42, iodine.

K. 2-[[2-[4-[[[2-(4-Chlorophenyl)ethyl]amino]-carbonyl]-4,5-dihydro-2-oxazolyl]-1-cyclohexenyl]methyl]benzenepropanoic acid, methyl ester To a stirred mixture of amide J (650 mg, 1.23 mmol) and triethylamine (0.34 mL, 2.47 mmol) in 30 mL of dry dichloromethane under argon at 0° C. was added mesyl chloride (0.12 mL, 1.54 mmol). The mixture was stirred at 0° C. for 30 minutes and at room temperature for 1 hour The mixture was concentrated in vacuo and diluted with 30 mL of acetone. To this mixture was added anhydrous potassium carbonate (1.19 g, 8.64 mmol). The mixture was refluxed for 4 hours and cooled to room temperature. The solid was filtered off and rinsed with acetone (4×30 mL). The filtrate was concentrated in vacuo. This was chromatographed on 60 g of Merck silica gel 60 using 2% methanol/dichloromethane as eluant to give 594 mg (95%) of oxazoline K.

TLC: silica gel, 4% methanol/dichloromethane $R_f$ 0.52, iodine.

L. 2-[[2-[4-[[[2-(4-Chlorophenyl)ethyl]amino]-carbonyl]-2-oxazolyl]-1-cyclohexenyl]methyl]-benzenepropanoic acid, methyl ester To a stirred mixture of oxazoline K (580 mg, 1.14 mmol) in 10 mL of dry dichloromethane was added nickel peroxide (1.16 g, 12.8 mmol). The mixture was stirred at room temperature for 2 hours, at which time more nickel peroxide (0.58 g, 0.64 mmol) was added. The mixture was stirred at room temperature for one hour and again nickel peroxide (0.29 g, 0.32 mmol) was added. The mixture was stirred at room temperature for one hour and a final batch of nickel peroxide (0.29 g, 0.32 mmol) was added. The mixture was stirred at room temperature for another 1.5 hours and then diluted with 120 mL of ethyl acetate. The mixture was combined with 30 mL of 3M sodium metabisulfite solution and 60 mL of 1M sodium citrate solution. The aqueous layer was separated and extracted with ethyl acetate (3×120 mL). The combined ethyl acetate extracts were dried (magnesium sulfate), filtered and concentrated in vacuo. This material was chromatographed on 60 g of Merck silica gel 60 using 1:1 hexane-ether as eluant to give 330 mg (57%) of oxazole-ester L.

TLC: silica gel, 2:1 hexane-ether $R_f$ 0.38, iodine.

M. 2-[[2-[4-[[[2-(4-Chlorophenyl)ethyl]amino]-carbonyl]-2-oxazolyl]-1-cyclohexenyl]methyl]-benzenepropanoic acid To a stirred mixture of oxazole-ester L (240 mg, 0.47 mmol) in 4 mL of freshly distilled tetrahydrofuran and 1 mL of water was added lithium hydroxide monohydrate (59.6 mg, 1.42 mmol). The mixture was stirred vigorously at room temperature for 25 hours and acidified to pH 2 by the addition of 1N hydrochloric acid solution. The mixture was diluted with 10 mL of water and extracted with ethyl acetate (1×30 mL) and trichloromethane (3×60 mL). The combined organic extracts were dried (magnesium sulfate), filtered and concentrated in vacuo. The crude acid was recrystallized in 10 mL of 20% methanol/dichloromethane and 25 mL of hexane at room temperature to give 145 mg (62%) of pure Example 11.

Melting point 168°–169° C.

TLC: silica gel, 6% methanol/dichloromethane.

$R_f$ 0.45, iodine.

EXAMPLE 12

2-[2-[4-[[[2-(4-Chlorophenyl)ethyl]amino]carbonyl]-2-oxazolyl]benzoyl]benzenepropanoic acid A. 2-[2-[3-[[Dimethyl(1,1,2-trimethylpropyl)-silyl]oxy]propyl]benzoyl]benzoic acid A 250-mL oven-dried flask containing a magnetic stir-bar was charged with 0.90 g of crushed magnesium turnings (37 mmol, Mallinckrodt) and placed under an argon atmosphere. After 10 mL of dry tetrahydrofuran (distilled from potassium/benzophenone) was added, the magnesium was activated at 65° by introduction of a crystal of iodine and a solution of 1.0 g and then 4.0 g of compound D from Example 5 in 4 mL of dry tetrahydrofuran (total 13.9 mmol). The reaction mixture briefly turned colorless, then green. The mixture was then heated to a gentle reflux for 1 hour and cooled to room temperature. The mixture consisted of a green, clear solution and some unreacted magnesium.

A 250-mL flask containing a magnetic stir-bar was charged with 1.38 g of phthalic anhydride (9.3 mmol) and placed under an argon atmosphere. After addition of 10 mL dry tetrahydrofuran (distilled from potassium/benzophenone), the resulting solution was cooled to 0° and the above Grignard solution was added slowly (cannulation). After the addition was complete, the reaction mixture was warmed slowly to 70° and stirred at that temperature for 12 hours. The reaction mixture was quenched with 10% aqueous hydrochloric acid and ether was added. The organic layer was separated, and the aqueous layer was extracted twice more with ether (100 mL each). The organic layers were combined and washed with brine, dried over (magnesium sulfate), filtered, and concentrated to obtain a yellow oil. This oil was flash-chromatographed eluting with hexane/ethyl acetate (95/5–70/30) to obtain pure compound A as an oil (3.50 g, 88% yield based on anhydride).

$R_f$=0.6 in 50% (1% acetic acid in EtOAc) in hexane, UV, cerium disulfate $^{13}$C NMR (67.8 MHz, CDCl$_3$) δ: 198.4, 171.3, 144.4, 143.7, 136.4, 132.7, 131.8, 131.1, 130.6, 129.7, 129.0, 128.6, 128.3, 125.2, 62.7, 34.2, 34.2, 30.3, 25.1, 20.4, 18.6, −3.3

B. N-[2-(4-Chlorophenyl)ethyl]-N-2-[2-[2-[3-[[dimethyl(1,1,2-trimethylpropyl]silyl]-oxy]propyl]benzoyl]benzoyl]-L-serinamide To a solution of 2.0 g (4.6 mmol) of compound A, 1.13 g (4.6 mmol) of N-[2-(4-Chlorophenyl)ethyl]-L-serinamide, hydrochloride, 0.70 g (5.1 mmol) of 1-hydroxybenzotriazole hydrate, and 0.57 mL of N-methylmorpholine (0.52 g, 5.1 mmol) in 25 mL dimethylformamide (Burdick & Jackson) stirring under argon at 0°, was added 0.99 g (5.1 mmol) of 1-(3-dimethylaminopropyl)-3-ethyl-carbodiimide hydrochloride in a single portion. All of the 1-(3- dimethylaminopropyl)-3-ethyl-carbodiimide hydrochloride dissolved. The reaction mixture was allowed to slowly warm to room temperature overnight, and a precipitate formed. This mixture was diluted with 100 mL ethyl acetate and washed with 25 mL 10% aqueous hydrochloric acid twice (all solids dissolved at this point), 25 mL water, 25 mL 1.0M aqueous sodium bicarbonate twice, 25 mL water, and finally with brine. The organic layer was dried over magnesium sulfate and evaporated to obtain 2.33 g of impure compound B, a thick oil. This material was used in the next step without further purification.

$R_f$=0.45 in ethyl acetate UV, cerium disulfate.

C. N-[2-(4-Chlorophenyl)ethyl]-2-[2-[2-[3-[[dimethyl(1,1,2-trimethylpropyl]silyl]-oxy]propyl]benzoyl]phenyl]-4,5-dihydro-4-oxazolecarboxamide A stirred solution of 2.33 g of crude compound B in 25 mL of dry dichloromethane under argon was cooled to 0°. 1.19 mL of triethylamine (0.87 g, 8.6 mmol), then 0.33 mL of methane-sulfonyl chloride (0.49 g, 4.2 mmol) were added. After 40 minutes, the mixture was warmed to room temperature, and 30 minutes later it was evaporated. To the residue (crude mesylate of compound B) under argon, was added 25 mL of acetone and 2.06 g of potassium carbonate (14.9 mmol). The mixture was refluxed for 4 hours. The solid was filtered off and rinsed with chloroform. The filtrate was evaporated and flash-chromatographed, eluting with 20% ethyl acetate in hexane to obtain 1.67 g (57% overall from compound A) of pure compound C as a thick oil. $R_f$=0.45 in 50% ethyl acetate in hexane, UV, cerium disulfate.

$^{13}$C NMR (67.8 MHz, CDCl$_3$) δ: 198.5, 171.5, 165.1, 144.0, 142.1, 137.1, 136.5, 132.0, 131.7, 130.8, 129.9, 129.4, 128.4, 125.4, 70.8, 69.0, 62.3, 40.1, 34.8, 34.3, 34.1, 30.3, 25.0, 20.3, 18.4, −3.5

D. N-[2-(4-Chlorophenyl)ethyl]-2-[2-[2-[3-[[dimethyl(1,1,2-trimethylpropyl]silyl]-oxy]propyl]benzoyl]phenyl]-4-oxazole-carboxamide To a stirred suspension of 0.74 g (3.3 mmol) of cupric bromide in 8 mL of ethyl acetate (Burdick & Jackson) at room temperature under argon, was added 1.0 mL (1.0 g, 6.6 mmol) of 1,8-diazabicyclo[5.4.0]undec-7-ene. The resulting dark mixture was stirred for 15 minutes before a solution of 1.0 g of compound C (1.6 mmol) in 8 mL of chloroform (Burdick & Jackson) was added. After 1 hour, 0.74 g of cupric bromide and 1.0 mL 1,8-diazabicyclo-[5.4.0]undec-7-ene were added. After another 20 hours (thin layer chromatography showed almost complete reaction), 0.74 g cupric bromide and 1.0 mL 1,8-diazabicyclo[5.4.0]undec-7-ene were added. After 4 hours more, the reaction mixture was diluted with 50 mL ethyl acetate. This was washed with 50 mL of a 1:1 (vol:vol) mixture of saturated aqueous ammonium chloride and concentrated aqueous ammonia. Two extractions of the aqueous layer with 50 mL ethyl acetate were performed. The combined extracts were dried over magnesium sulfate and evaporated. Flash chromatography (10% to 20% ethyl acetate in hexane gradient) allowed isolation of 0.68 g (65%) of pure compound D as a white solid. $R_f$=0.5 in 50% ethyl acetate in hexane, UV, cerium disulfate.

$^{13}$C NMR (67.8 MHz, CDCl$_3$) δ: 197.8, 160.1, 159.9, 143.9, 141.0, 140.8, 137.0, 136.1, 132.1, 131.9, 137.7, 131.2, 130.6, 130.3, 129.9, 129.0, 128.9, 128.6, 125.4, 124.8, 62.3, 40.0, 35.0, 34.5, 34.0, 30.6, 25.0, 20.3, 18.4, −3.5

E. 2-[2-[4-[[[2-(4-Chlorophenyl)ethyl]amino]-carbonyl]-2-oxazolyl]benzoyl]benzenepropanoic acid A solution of compound D (0.30 g, 0.48 mmol) in 3 mL of acetone was stirred under argon at 0°. Jones reagent was added until the reaction mixture stayed orange. After one hour, the reaction was complete as indicated by thin layer chromatography. The excess of reagent was quenched with isopropyl alcohol. The resulting mixture was concentrated to obtain a white and blue precipitate. To this was added 30 mL of water, and extraction three times with 50 mL of ethyl acetate followed. The organic layers were combined, washed with brine, and dried over magnesium sulfate. The mixture was filtered and concentrated on a rotoevaporator. The residue was flash-chromatographed, eluting with a 1:1 mixture of ethyl acetate/hexane to obtain an oil. This oil was crystallized from hexane/chloroform to obtain Example 12 as a white solid (0.20 g, 84%).

Melting point 58°–62°

$R_f$=0.65 in 10% acetic acid in ethyl acetate, UV, cerium disulfate

EXAMPLE 13

2-[[2-[4-[[(4-Cyclohexylbutyl)amino]carbonyl]-2-oxazolyl]phenyl]carbonyl]benzenepropanoic acid A. 2-[2-[3-[[Dimethyl(1,1,2-trimethylpropyl)-silyl]oxy]propyl]benzoyl]benzoic acid To a mixture of crushed magnesium turnings (1.8 g, 74.04 mmol) and 10 mL tetrahydrofuran (distilled from potassium/benzophenone) under argon at room temperature was added a solution of compound D from Example 5 (2.0 g, 5.6 mmol) in 1 mL distilled tetrahydrofuran with stirring. The reaction mixture was activated by addition of one drop of 1,2-dibromoethane (Aldrich). Bubbling was noted. An additional 8.0 g of compound D from Example 5 (22.4 mmol) dissolved in 5 mL distilled tetrahydrofuran was added to the reaction vessel. Bubbling continued and a green color developed. The reaction vessel quickly warmed and was allowed to stir under argon until it had returned to room temperature (about 1 hour). During this time bubbling ceased and the mixture became a deep green.

A solution of phthalic anhydride (2.76 g, 18.4 mmol) in 10 mL of distilled tetrahydrofuran was prepared and placed under argon, and then stirred at 0° for 5 minutes. The Grignard solution prepared above was added slowly by syringe. The resulting mixture was allowed to warm to room temperature and then stirred overnight. The mixture was diluted with diethyl ether (about 18 mL). Excess Grignard reagent was quenched by addition of 10% (aqueous) hydrochloric acid (about 10 mL), after which the organic layer was removed. The remaining aqueous layer was washed twice with ether. The three organic layers were combined and dried over sodium sulfate, filtered, and concentrated. The resulting yellow oil was purified by flash chromatography (silica, 1% acetic acid in (10%–50% ethyl acetate in hexane gradient)) to give 7.48 g of compound A (92%, 6.88 g) in the form of a clear oil. This oil represented an 88% yield based on phthalic anhydride.

TLC (50% ethyl acetate/1% acetic acid/49% hexane): $R_f$=0.60, p-anisaldehyde stain.

$^{13}$C NMR (67.8 Hz in CDCl$_3$): δ 198.2, 171.4, 144.3, 143.2, 137.0, 134.1, 132.2, 131.8, 131.1, 130.5, 129.7, 128.8, 126.5, 125.0, 63.2, 34.4, 30.3, 25.1, 21.2, 20.5, 18.5, −3.5.

B. N-(4-Cyclohexylbutyl)-N-2-[2-[2-[3-[[dimethyl(1,1,2-trimethylpropyl)silyl]-oxy]propyl]benzoyl]benzoyl]serine To a solution of 1.14 g of amine hydrochloride M from Example 5 (4.10 mmol), 1.75 g 2 (92%, 1.61 g, 3.78 mmol., 0.92 equiv), 0.58 g of 1-hydroxybenzotriazole hydrate (4.6 mmol, 1.1 equiv), and 0.52 mL N-methylmorpholine (0.47 g, 1.1 equiv), in 15 mL dimethylformamide (Burdick and Jackson), stirring under argon at room temperature, was added 880 mg of 1-(3-dimethylaminopropyl)-3-ethylcarbodiimide hydrochloride (4.6 mmol, 1.1 equiv). The mixture was stirred for 2 hours at which time another 150 mg of acid A (92%, 138 mg, 0.33 mmol, 0.08 equiv) was added. The reaction mixture was stirred overnight. The mixture was then diluted with ethyl acetate to an approximate volume of 100 mL, then washed twice with about 25 mL 1M (aq) hydrochloric acid, and washed twice with about 25 mL of 1M (aqueous) sodium bicarbonate. The organic layer was dried over sodium sulfate and concentrated to obtain crude compound B. The crude product was purified by flash chromatography (silica, 0.5% concentrated aqueous ammonium hydroxide 4.5% methanol, in methylene chloride) to give 2.25 g of compound B (95%, 2.14 g), a yellow-white solid, in 80% yield.

TLC (ethyl acetate):

$R_f$=0.40, p-anisaldehyde stain.

$^{13}$C NMR (67.8 MHz in CDCl$_3$): δ 198.5, 168.5, 167.8, 142.2, 138.0, 136.8, 130.8, 130.4, 129.9, 129.4, 128.6, 126.7, 124.8, 62.2, 55.0, 53.1, 49.8, 37.1, 36.8, 34.5, 33.5, 32.7, 29.9, 29.1, 27.2, 26.9, 24.9, 23.7, 19.9, 17.8, –4.8.

C. N-(4-Cyclohexylbutyl)-2-[2-[2-[3-[[dimethyl(1,1,2-trimethylpropyl)silyl]-oxy]propyl]benzoyl]phenyl]-4,5-dihydro-4-oxazolecarboxamide A solution of 1.99 g of compound B (95%, 1.89 g, 2.91 mmol), 2.43 g of triphenylphosphine (9.18 mmol, 3 equiv), and 0.83 mL of diisopropylethylamine (1.18 g, 9.18 mmol, 3 equiv) in about 20 mL of acetonitrile and about 5 mL of methylene chloride was prepared and placed under argon at room temperature. To this mixture was added 0.90 mL of carbon tetrachloride (1.40 g, 9.18 mmol, 3 equiv). The reaction mixture was allowed to stir overnight. To the mixture was added about 25 mL 1M (aqueous) sodium bicarbonate. The mixture was extracted three times with about 20 mL of methylene chloride. The combined organic extracts were dried over sodium sulfate and concentrated. Purification by flash chromatography (silica, 25% ethyl acetate in hexane) resulted in 1.82 g of oxazoline C (85%, 1.55 g) in the form of a brown oil, representing an 80% yield.

TLC (25% ethyl acetate in hexane):

$R_f$=0.22, p-anisaldehyde stain.

$^{13}$C NMR (67.8 MHz in CDCl$_3$): δ 198.6, 171.4, 165.1, 144.2, 142.2, 136.5, 131.8, 131.3, 131.1, 129.9, 129.5, 128.5, 125.6, 125.4, 70.9, 69.1, 62.4, 39.2, 37.4, 37.0, 34.4, 34.1, 33.2, 30.5, 29.6, 26.6, 26.3, 24.0, 20.3, 18.5, –3.4.

D. N-(4-Cyclohexylbutyl)-2-[2-[2-[3-[[dimethyl(1,1,2-trimethylpropyl)silyl]-oxy]propyl]benzoyl]phenyl]-4-oxazole-carboxamide A slurry of 390 mg of freshly prepared nickel peroxide in about 5 mL of methylene chloride was placed under argon. To this was added 500 mg of oxazoline C (85%, 425 mg, 0.67 mmol). The mixture was allowed to stir for 1 hour. The mixture was then filtered through Celite® and the solvent evaporated to give 390 mg of crude oxazole D.

TLC (25% ethyl acetate in hexane):

$R_f$=0.30, p-anisaldehyde stain.

$^{13}$C NMR (67.8 MHz in CDCl$_3$): δ 198.0, 160.3, 159.8, 144.1, 141.0, 140.8, 137.1, 136.1, 132.0, 131.8, 131.3, 130.6, 130.3, 129.1, 128.8, 125.4, 124.9, 62.5, 39.1, 37.5, 37.1, 34.7, 34.2, 33.3, 30.8, 29.9, 28.2, 26.6, 26.3, 24.1, 20.3, 18.5, –3.4.

E. 2-[[2-[4-[[(4-Cyclohexylbutyl)amino]-carbonyl]-2-oxazolyl]phenyl]carbonyl]-benzenepropanoic acid A solution of 390 mg crude oxazole D in about 3 mL of acetone (Burdick and Jackson) was stirred under argon at 0°. Jones reagent was added until the reaction mixture remained orange in color. The mixture was allowed to stir for 1 hour. At that time, excess Jones reagent was quenched by the addition of isopropanol. To this mixture was added about 30 mL of water. The mixture was washed three times with about 50 mL of ethyl acetate. The organic layers were combined, dried over sodium sulfate, and concentrated to yield 380 mg of crude Example 13 in the form of a brown solidifying oil. Flash chromatography (silica, 1% acetic acid in (5% ethyl acetate in hexane)) produced 79.2 mg of Example 13. This represents an overall 23% yield from compound C.

TLC (20% acetone in toluene):

$R_f$=0.33, UV, homogeneous, p-anisaldehyde stain.

IR (dichloromethane film): 3406, 3142, 3063, 2922, 2850, 1722, 1599 cm$^{-1}$.

MS(CI): 503 (M+H)$^+$.

Analysis calc'd for $C_{30}H_{34}N_2O_4$-0.35 mol $H_2O$: C, 70.81; H, 6.87; N, 5.51.

Found C, 71.00; H, 7.31; N, 5.32.

EXAMPLE 14

2-[2-[4-[[[2-(4-Chlorophenyl)ethyl]amino]-carbonyl]-2-oxazolyl]phenoxy]benzenepropanoic acid A. 2-Iodobenzoic acid, benzyl ester To a stirred mixture of 2-iodobenzoic acid (8.70 g, 35.1 mmol) and potassium carbonate (20.2 g, 176 mmol) in 100 mL of acetone was added benzyl bromide (5.00 g, 29.2 mmol). The mixture was stirred at room temperature for 23 hours and the solid was filtered off. The solid was rinsed with acetone (2×30 mL). The filtrate was concentrated in vacuo. The residue was dissolved in 200 mL of ether and washed with saturated sodium bicarbonate solution (2×50 mL) and brine (1×50 mL). The ether layer was dried (magnesium sulfate), filtered and concentrated in vacuo to give 8.63 g (87%) of benzyl 2-iodobenzoate A.

TLC: silica gel, 2% methanol/dichloromethane $R_f$ 0.84, iodine.

B. 3-(2-Hydroxyphenyl)-2-propenoic acid, methyl ester

To a stirred mixture of ortho-hydroxycinnamic acid (1.00 g, 6.09 mmol) in 10 mL of ether and 10 mL of methanol was added etheral diazomethane until the mixture became yellowish. The mixture was stirred at room temperature for 15 minutes, and the excess diazomethane was destroyed with the addition of acetic acid. The mixture was concentrated in vacuo and diluted with 100 mL of ethyl acetate. This ethyl acetate solution was washed with saturated sodium bicarbonate solution (3×60 mL) and brine (1×60 mL). The organic layer was dried (magnesium sulfate), filtered and concentrated in vacuo to give 1.02 g (94%) of methyl ortho-hydroxycinnamate B.

TLC: silica gel, 2% methanol/dichloromethane, $R_f$ 0.80, iodine.

C. (E)-2-[2-(3-Methoxy-3-oxo-1-propenyl)-phenoxy]benzoic acid, phenylmethyl ester To a stirred mixture of benzoate A (1.67 g, 4.96 mmol), cinnamate B (0.74 g, 4.13 mmol) and anhydrous potassium carbonate (1.14 g, 8.26 mmol) in 6 mL of dry pyridine under argon was added cupric oxide (0.82 g, 10.3 mmol). The mixture was heated at 125° C. under argon for 19 hours and cooled to room temperature. The mixture was filtered through a 2" pad of Celite and the pad was rinsed with ethyl acetate (5×60 mL). The filtrate was washed with 1N hydrochloric acid solution (3×100 mL) and brine (1×100 mL). The organic layer was dried (magnesium sulfate), filtered and concentrated in vacuo. This concentrate was chromatographed on 40 g of Merck silica gel 60 using hexane-ether 4:1 as eluant to give 850 mg (53%) of desired diaryl ether C.

TLC: silica gel, 2% methanol/dichloromethane
$R_f$ 0.60, iodine.

D. (E)-2-[2-(3-Methoxy-3-oxopropyl)phenoxy]-benzoic acid, phenylmethyl ester

Diaryl ether C was dissolved in 100 mL of ethyl acetate and washed with 1N lithium hydroxide solution (2×30 mL), 10% potassium hydrogen sulfate solution (2×30 mL) and brine (1×30 mL). The organic layer was dried (magnesium sulfate), filtered and concentrated in vacuo. To a stirred mixture of this diaryl ether (1.05 g, 2.71 mmol) in 20 mL of ethyl acetate and 5 mL of methanol under argon at room temperature was added 20% palladium dihydroxide on carbon (0.21 g, 20% based on the weight of ester C). The atmosphere was switched to hydrogen with several vacuum-fill cycles. The mixture was stirred at room temperature for 24 hours, and the catalyst was filtered off through a 4 μM polycarbonate film. The solid was rinsed with ethyl acetate (4×30 mL). The filtrate was concentrated in vacuo and chromatographed on 34 g of Merck silica gel 60 using 4% methanol/dichloromethane as eluant to give 220 mg of desired acid D and some impure acid. This impure acid was then triturated in 20 mL of 4:1 hexane-ether to give 408 mg of pure acid D. The total yield was 608 mg (76%). TLC: silica gel, 4% methanol/dichloromethane.
$R_f$ 0.32, iodine.

E. (S)-2-[2-[[[2-[[2-(4-Chlorophenyl)ethyl]-amino]-1-(hydroxymethyl)-2-oxoethyl]amino]-carbonyl]phenoxy]benzenepropanoic acid, methyl ester To a stirred mixture of acid D (408 mg, 1.37 mmol), 1-hydroxybenzotriazole monohydrate (231 mg, 1.37 mmol), N-[2-(4-Chlorophenyl)ethyl]-L-serinamide, hydrochloride and triethylamine (0.57 mL, 4.10 mmol) in 20 mL of dimethylformamide under argon at room temperature was added ethyl-3-(3-dimethylamino) propylcarbodiimide hydrochloride salt (262 mg, 1.37 mmol). The mixture was stirred at room temperature for 18 hours and concentrated in vacuo. The residue was diluted with 400 mL of ethyl acetate and washed with 0.2N sodium hydroxide solution (2×70 mL), 1N hydrochloric acid solution (2×70 mL), saturated sodium bicarbonate solution (1×70 mL) and brine (1×70 mL). The ethyl acetate layer was dried (magnesium sulfate), filtered and concentrated in vacuo. Purification was effected by flash chromatography on 36 g of Merck silica gel 60 using 2% methanol/dichloromethane as eluant to give 525 mg (74%) of amide E.
TLC: silica gel, 4% methanol/dichloromethane.
$R_f$ 0.46, iodine.

F. 2-[2-[4-[[[2-(4-Chlorophenyl)ethyl]amino]-carbonyl]-4,5-dihydro-2-oxazolyl]phenoxy]-benzenepropanoic acid, methyl ester To a stirred mixture of amide E (520 mg, 0.99 mmol) under argon at 0° C. in 5 mL of dry dichloromethane was added sequentially triethylamine (0.28 mL, 1.98 mmol) and mesyl chloride (0.096 mL, 1.24 mmol). The mixture was stirred at 0° C. for 10 minutes and at room temperature for 1 hour. The mixture was concentrated in vacuo and diluted with 10 mL of acetone. To this mixture was added potassium carbonate (0.69 g, 4.96 mmol). The mixture was refluxed under argon for 2 hours and cooled to room temperature. The solid was filtered off and rinsed with acetone (4×30 mL). The filtrate was concentrated in vacuo and chromatographed on 44 g of Merck silica gel 60 using 2% methanol/dichloromethane as eluant to give 490 mg (98%) of oxazoline F.

TLC: silica gel, 4% methanol/dichloromethane.
$R_f$ 0.78, iodine.

G. 2-[2-[4-[[[2-(4-Chlorophenyl)ethyl]amino]-carbonyl]-2-oxazolyl]phenoxy]benzenepropanoic acid, methyl ester To a stirred mixture of cupric bromide (444 mg, 1.99 mmol) under argon at room temperature in 4 mL of ethyl acetate was added 1,8-diazabicyclo [5.4.0]undec-7-ene (0.60 mL, 3.98 mmol). The mixture was stirred at room temperature for 30 minutes, at which time a solution of oxazoline F (480 mg, 0.95 mmol) in 4 mL of chloroform was added. This mixture was stirred at room temperature for 16 hours. To this stirred mixture was again added cupric bromide (222 mg, 1.00 mmol) and 1,8-diazabicyclo[5.4.0]undec-7-ene (0.30 mL, 1.99 mmol). The mixture was stirred at room temperature for 8 hours, at which time once more cupric bromide (222 mg, 1.00 mmol) and 1,8-diazabicyclo [5.4.0]undec-7-ene (0.30 mL, 1.99 mmol) were added. The mixture was stirred at room temperature for 16 hours. Another batch of cupric bromide (222 mg, 1.00 mmol) and 1,8-diazabicyclo[5.4.0]undec-7-ene (0.30 mL, 1.99 mmol) were added. The mixture was stirred at room temperature for another 8 hours and again cupric bromide (222 mg, 1.00 mmol) and 1,8-diazabicyclo[5.4.0]undec-7-ene (0.30 mL, 1.99 mmol) were added. The mixture was stirred at room temperature for 16 hours and poured into a mixture of 100 mL of ethyl acetate and 70 mL of 1:1 saturated ammonium chloride solution and concentrated ammonium hydroxide solution. The aqueous layer was separated and extracted with ethyl acetate (3×100 mL). The combined ethyl acetate extractions were dried (magnesium sulfate), filtered and concentrated in vacuo. This concentrate was chromatographed on 45 g of Merck silica gel 60 using 350 mL of each of 1:1 and 1:2 hexane-ether as eluants to give 267 mg (56%) of oxazole G.
TLC: silica gel, 2% methanol/dichloromethane
$R_f$ 0.64, iodine.

H. 2-[2-[4-[[[2-(4-Chlorophenyl)ethyl]amino]-carbonyl]-2-oxazolyl]phenoxy]benzenepropanoic acid To a stirred mixture of oxazole G (260 mg, 0.52 mmol) under argon at room temperature in 5 mL of freshly distilled tetrahydrofuran and 1 mL of water was added lithium hydroxide monohydrate (64.8 mg, 1.55 mmol). The mixture was stirred at room temperature for 26 hours and acidified to pH 2 by the addition of 1N hydrochloric acid solution. The resulting mixture was diluted with 20 mL of water, saturated with sodium chloride and extracted with ethyl acetate (4×40 mL). The combined ethyl acetate extracts were dried (magnesium sulfate), filtered and concentrated in vacuo. This concentrate was chromatographed on 20 g of Merck silica gel 60 using 4% methanol/dichloromethane as eluant to give 200 mg of acid. This acid was crystallized in 6 mL of 3:2 hexane-ethyl acetate at −5° C. to give 190 mg (75%) of pure Example 14, as a solid.
Melting point 127°–128° C.
TLC: silica gel, 4% methanol/dichloromethane.
$R_f$ 0.28, iodine.
$^{13}$C NMR of 11 (67.5 MHz, CDCl$_3$) δ: 177.5, 160.9, 159.1, 155.0, 154.3, 141.2, 137.3, 136.8, 132.4, 132.1, 131.4, 131.0, 130.4, 130.1, 128.6, 128.1, 124.2, 123.2, 118.6, 118.4, 117.5, 40.3, 35.4, 34.4, 26.3.

EXAMPLE 15

2-[3-[4-[[(4-Cyclohexylbutyl)amino]carbonyl]-2-oxazolyl]propyl]benzenepropanoic acid A. 2-(4-Hydroxy-1-butyn-1-yl)benzaldehyde To a suspension of palladium chloride (11.0 mg, 0.618 mmol) and cuprous iodide (Aldrich gold label, 43.5 mg, 0.229 mmol) in triethylamine (distilled from calcium hydride, 53 mL) was added, sequentially, triphenylphosphine (439 mg, 1.67 mmol), 3-butyn-1-ol (8.0 mL, 106 mmol), and 2-bromobenzaldehyde (10.6 mL, 88.3 mmol). The mixture was refluxed for 7 hours. The mixture was cooled to room temperature, diluted with ether (300 mL) and filtered. The pad was washed with ether (3×50 mL) and the combined filtrates were concentrated in vacuo to an oil: 16.1 g; $^1$H NMR (270 MHz, deuteriochloroform) δ 10.4 (1H, s), 7.85 (d, J=7 Hz), 7.35–7.50 (m, 3H), 3.0–4.0 (br s, 1H), 3.85 (t, J=6 Hz, 2H), 2.74 (t, J=6 Hz, 2H);
$^{13}$C NMR (complete decoupling, 67.8 MHz, deuteriochloroform) δ 192.0, 135.7, 133.6, 133.2, 127.9, 127.7, 126.6, 94.5, 77.9, 60.6, 23.7.
$R_f$ (silica, 50% ethyl acetate/hexanes) 0.31.

B. 2-(4-Hydroxy-1-butyn-1-yl)benzeneprop-2-enoic acid, methyl ester

A solution of aldehyde A in tetrahydrofuran (600 mL) and methyl (triphenylphosphoranylidine)-acetate (29.5 g, 88 mmol) was stirred at room temperature for 5 hour The reaction was then concentrated in vacuo and chromatographed (silica, flash, 100 mm dia., 4 L of 67% ether/hexanes then 4 L of 75% ether/hexanes, load compound dissolved in benzene) to yield 17.0 g (84%) of an oil:
$^1$H NMR (270 MHz, deuteriochloroform) δ 8.18 (d, J=16 Hz, 1H), 7.53–7.56 (m, 1H), 7.41–7.44 (m, 1H), 7.23–7.26 (m, 2H), 6.47 (d, J=16 Hz, 1H), 3.87 (t, J=6 Hz, 2H), 3.78 (s, 3H), 3.21 (br s, 1H), 2.75 (t, J=6 Hz, 2H);
$^{13}$C NMR (complete decoupling, 67.8 MHz, deuteriochloroform) δ 167.4, 142.9, 135.3, 132.5, 129.5, 127.8, 125.8, 124.3, 118.6, 93.6, 79.4, 60.8, 51.5, 23.7;
$R_f$ (silica, 50% ethyl acetate/hexanes) 0.31.

C. 2-(4-Hydroxybutyl)benzenepropanoic acid, methyl ester

A solution of unsaturated alcohol-ester B (7.0 g, 30.4 mmol) in methanol (250 mL) was added to 10% palladium on carbon (700 mg) under argon. The argon was replaced with hydrogen (balloon, four pump/purge cycles), and the mixture was stirred for 3 hours. The reaction was filtered through Celite® and the pad was rinsed with methanol (20 mL). The combined filtrates were concentrated in vacuo. The residue was taken up in ether (250 mL) and filtered through Celite®. The filtrate was then concentrated in vacuo. An oil (7.0 g, 98%) was obtained: $^1$H NMR (270 MHz, deuteriochloroform) δ 7.11 (s, 4H), 3.64 (m, 5H), 2.91–2.95 (m, 2H), 2.54–2.63 (m, 5H), 1.62–1.63 (m, 4H);
$^{13}$C NMR (complete decoupling, 67.8 MHz, deuteriochloroform) δ 173.3, 140.0, 137.8, 129.1, 128.5, 126.2, 125.9, 62.1, 51.4, 35.0, 32.3, 32.0, 27.4, 27.1.

D. 2-[2-(Methoxycarbonyl)ethyl]benzenebutanoic acid

To a 0° C. solution of alcohol C (0.500 g, 2.12 mmol) in acetone (25 mL) was added freshly prepared Jones Reagent (2.67M, 6 mL, contains 1 mg manganese sulfate monohydrate/mL). The reaction was stirred for 30 minutes, quenched with 2-propanol (10 mL) and then concentrated in vacuo. The residue was partitioned between methylene chloride (75 mL) and water (50 mL). The aqueous layer was then extracted with methylene chloride (2×25 mL). The combined organic layers were washed with sodium chloride (half-saturated, 50 mL, contining 0.5 g sodium metabisulfite. The combined organic layers were dried (sodium sulfate) and concentrated in vacuo. The residual oil was taken up in ether (100 mL) and was washed (water, 25 mL containing 0.5 g sodium metabisulfite; 1N citric acid, 20 mL; water, 25 mL), dried (sodium sulfate) and concentrated in vacuo. A transparent colorless oil (0.50 g, 94%) was obtained: $^1$H NMR (270 MHz, deuteriochloroform) δ 7.13 (s, 4H), 3.65 (br s, 3H), 1.91–2.95 (m, 10H);
$^{13}$C NMR (complete decoupling, 67.8 MHz, deuteriochloroform) δ 178.9, 173.1, 138.8, 137.9, 129.1, 128.6, 126.1, 51.3, 34.9, 33.2, 31.4, 27.2, 25.6.
$R_f$ (silica, 20% methanol/chloroform) 0.54.

E. 2-[4-[[2-[(4-Cyclohexylbutyl)amino]-1-(hydroxymethyl)-2-oxoethyl]amino]-4-oxo-butyl]benzenepropanoic acid, methyl ester To a mixture of acid D (1.04 g, 4.16 mmol) and amine M from Example 5 (trifluoracetic acid salt, about 5.0 mmol) was added triethylamine (0.70 mL, 5.0 mmol), 1-(3-dimethylaminopropyl)-3-ethylcarbodiimide hydrochloride (956 mg, 5.0 mmol), and 1-hydroxybenzotriazole (674 mg, 5.0 mmol). The reaction was stirred for 2 hours and was then diluted with ether (200 mL) and washed (50 mL of 0.5N hydrochloric acid, 50 mL of water, 50 mL of 0.5N sodium carbonate, 50 mL of saturated sodium chloride). The combined organic layers were dried (magnesium sulfate) and concentrated in vacuo. The resultant gel was chromatographed (flash, silica, 50 mm dia., ethyl acetate) to yield a solid (1.37 g, 69%):
$^1$H NMR (270 MHz, deuteriochloroform) δ 7.04–7.23 (m, 6H), 3.80–4.60 (m, 3H), 3.66 (s, 3H), 3.17–3.25 (m, 2H), 2.91–2.97 (m, 2H), 2.55–2.68 (m, 4H), 2.30–2.36 (m, 2H), 0.84–1.94 (m, 19H).
$^{13}$C NMR (complete decoupling, 67.8 MHz, deuteriochloroform) δ 173.6, 173.3, 170.5, 139.0, 138.0, 129.2, 128.7, 126.4, 126.3, 63.0, 54.2, 51.5, 39.5, 37.4, 36.9, 35.7, 35.0, 33.2, 31.7, 29.5, 27.4, 26.6, 26.5, 26.2, 24.0.
$R_f$ (silica, ethyl acetate) 0.24.

F. 2-[3-[4-[[(4-Cyclohexylbutyl)amino]-carbonyl]-4,5-dihydro-2-oxazolyl]propyl]-benzenepropanoic acid, methyl ester Carbon tetrachloride (1.2 mL, 12 mmol) was added to a solution of ester E (944 mg, 1.99 mmol), triethylamine (0.83 mL, 5.97 mmol) and triphenylphosphine (1.56 g, 5.97 mmol) in acetonitrile (50 mL). The reaction was stirred for 3 hours, diluted with ethyl acetate (250 mL) and washed (50 mL saturated sodium chloride containing 5 mL of water, 50 mL of saturated sodium chloride). The combined organic layers were dried (magnesium sulfate) and concentrated in vacuo. The residue was chromatographed (flash, silica, 50 mm dia., 70% ethyl acetate/hexanes) to yield an oil (778 mg, 86%):
$^1$H NMR (270 MHz, deuteriochloroform) δ 7.15 (s, 4H), 6.57 (br m, 1H), 4.37–4.61 (m, 3H), 3.68 (s, 3H), 3.19–3.28 (m, 2H), 2.94–3.00 (m, 2H), 2.57–2.73 (m, 4H), 2.36–2.41 (m, 2H), 1.89–1.97 (m, 2H), 0.82–1.68 (m, 17H).
$R_f$ (silica, ethyl acetate) 0.38.

G. 2-[3-[4-[[(4-Cyclohexylbutyl)amino]-carbonyl]-2-oxazolyl]propyl]benzenepropanoic acid, methyl ester A mixture of oxazoline F (340 mg, 0.745 mmol) and nickel peroxide/Celite (1.22 mmol oxidant/g, 4.9 g) in benzene (20 mL) was refluxed for 1 hour The reaction was cooled to room temperature and filtered. The pad was washed with benzene (50 mL) and the combined filtrates were concentrated in vacuo. An oil (220 mg) was obtained. This material was combined with material from a 0.49-mmol scale reaction and the whole was chromatographed (silica, flash, 25 mm dia., 30% ethyl acetate/hexanes) to yield 302 mg (54%) of an oil:
$^1$H NMR (90 MHz, deuteriochloroform) δ 8.08 (s, 1H), 7.15 (s, 4H), 6.84–7.15 (m, 1H), 3.68 (s, 3H), 3.29–3.44 (m, 2H), 2.50–3.06 (m, 8H), 1.10–2.15 (m, 19H);

$^{13}$C NMR (complete decoupling, 22.5 MHz, deuteriochloroform) δ 173.1, 164.1, 160.5, 140.3, 138.8, 138.1, 136.2, 129.3, 128.8, 126.5, 51.5, 39.0, 37.4, 37.0, 35.1, 33.2, 31.6, 29.9, 27.8, 27.4, 26.6, 26.2, 24.1; $R_f$ (silica, ethyl acetate) 0.71.

H. 2-[3-[4-[[(4-Cyclohexylbutyl)amino]-carbonyl]-2-oxazolyl]propyl]benzenepropanoic acid To a solution of ester G (427 mg, 0.94 mmol) in methanol (10 mL) was added 2N potassium hydroxide (4 mL) and then sufficient methylene chloride to yield a homogeneous solution (ca. 4 mL). The reaction was stirred for 4 hours and then concentrated in vacuo to remove the organic solvents. The residue was taken up in methylene chloride (30 mL) and was acidified with 1N hydrochloric acid to pH 1.5. The methylene chloride layer was separated and the aqueous layer was further extracted with methylene chloride (3×10 mL). The combined organic layers were dried (sodium sulfate) and concentrated in vacuo. The oil was chromatographed (silica, flash, 15 mm dia., 50% ethyl acetate/hexanes then ethyl acetate) to yield an oil which crystallized when swirled with hexanes. The chromatography column was flushed with 5% methanol/methylene chloride to recover the remainder of the product. The combined materials were dissolved in ethyl acetate (5 mL) and were filtered through a 0.45 m Gelman acrodisk CR filter. The filtrate was concentrated and the solid was recrystallized from ethyl acetate/hexanes (about 10 mL) to yield 267 mg (67%) of a white powder. A small second crop was obtained from the mother liquors. For the first crop:
Melting point 95.0°–96.0°C.
$^1$H NMR (90 MHz, deuteriochloroform) d 9.79 (br s, 1H), 8.71 (s, 1H), 7.16 (s, 5H), 3.08–3.42 (m, 2H), 2.64–3.08 (m, 8H), 0.88–2.13 (m, 19H).
$^{13}$C NMR (complete decoupling, 22.5 MHz, deuteriochloroform) d 177.0, 164.4, 160.9, 141.0, 138.9, 135.9, 129.3, 128.9, 126.6, 39.2, 37.5, 37.0, 35.1, 33.3, 31.7, 29.8, 27.9, 27.6, 27.3, 26.6, 26.3, 24.1.
IR (KBr) 3414 (s), 3129 (m), 3103 (m), 3064 (m), 3030 (m), 3019 (m), 2923 (vs), 2851 (s), 1710 (s, 1651 (s), 1603 (s), 1521 (m), 1492 (w), 1448 (w), 1382 (w), 1377 (w), 1314 (w), 1294 (w), 1213 (w), 1199 (w), 1179 (w), 1105 (w), 933 (w), 827 (w), 755 (w) cm$^{-1}$; LRMS (CI, CH$_2$Cl$_2$/NH3 DEP, pos. ion spectrum) m/z (rel. int.) 442 (28), 441 (100), 398 (19), 397 (18), 393 (16), 242 (14), 201 (17), 156 (15).
$R_f$ (silica, ethyl acetate) 0.39.
Anal. calc'd for $C_{22}H_{36}N_2O_4 \cdot 0.12$ H$_2$O C, 70.54; H, 8.25; N, 6.33.
Found: C, 70.55; H, 8.35; N, 6.30.

EXAMPLE 16 cis-2-[[5-[4-[[[2-(4-Chlorophenyl)ethyl]amino]-carbonyl]-2-oxazolyl]-1,3-dioxolan-4-yl]methyl]-benzenepropanoic acid A. (Z)-4-[(Benzyl)oxy]-2-buten-1-ol Preparation of compound A is known in the art. See, e.g., S. Hagishita and K. Seno, *Chem. Pharm. Bull.* 37 (1989), 327.

B. (Z)-4-(Benzyloxy)-2-butenyl acetate

A stirred solution of compound A (7.13 g, 40 mmol), pyridine (7.5 mL) in dichloromethane (30 mL) was treated with acetic anhydride (5 g, 49 mmol). After 24 hours the mixture was diluted with ether (150 mL) and washed with water (50 mL), saturated copper sulfate solution (25 mL,3x), dried (magnesium sulfate), filtered and concentrated. The residue was coevaporated with toluene (10 mL, 3x) to obtain the title compound (5.93 g) as a colorless oil.

C. (Z)-2-[4-(Benzyloxy)-2-butenyl]benzenepropan-1-ol, dimethylthexylsilyl ether

A suspension of magnesium turnings (1.3 g, 54 mmol) and catalytic iodine in anhydrous tetrahydrofuran (30 mL) was heated under reflux. A few drops of [3-(2-bromophenyl)]-propanol, dimethylthexylsilyl ether was added to initiate the formation of Grignard reagent. Once the iodine color was discharged, additional bromide (a total of 6 g, 18.24 mmol) was added in one portion. The mixture was heated under reflux for 1 hours cooled to 0° C. in an ice-water bath and was then added via cannula to a solution of compound B (3.3 g, 15 mmol) and a 0.1M solution of dilithium copper tetrachloride (1 mL) in tetrahydrofuran (10 mL) at −78° C. The mixture was stirred at −78° C. for 30 minutes and at 0° C. for 2 hours, then quenched with saturated ammonium chloride solution. The tetrahydrofuran layer was separated and the aqueous layer was extracted with ether (50 mL, 2x). The organic extracts were combined, dried (magnesium sulfate), filtered and concentrated. The residue was chromatographed on a silica gel column and eluted with hexanes and 0.5–1.5% ethyl acetate in hexanes to obtain the title compound (8.5 g) contaminated with some low $R_f$ impurities.

D. (Z)-2-[4-(Benzyloxy)-2-butenyl]benzenepropanoic acid, methyl ester

A solution of compound C (8.5 g) in acetone (50 mL) was treated dropwise at 0°–5° C. with a 2.67M solution of Jones reagent in acetone (10 mL). After 2 hours the mixture was warmed to room temperature and stirred for additional 1 hour. Excess Jone reagent was destroyed by addition of isopropanol(10 mL) at 0°–5° C. The mixture was diluted with water (100 mL) and extracted with ethyl acetate (100 mL, twice). The ethyl acetate layer was separated and the aqueous layer was extracted with ethyl acetate. The ethyl acetate extracts were combined, dried (magnesium sulfate), filtered and concentrated under reduced pressure to obtain a yellow oil, which was dissolved in methanol (30 mL) and cooled to 0°–5° C. Acetyl chloride (2 mL) was added dropwise. The mixture was warmed to room temperature and stirred for 2 hours. The mixture was concentrated under reduced pressure, and the residue was chromatographed on a silica gel column. Elution with 5% ethyl acetate in hexanes afforded the title compound (2.4 g, 50% overall yield from B) as a colorless oil.

E. (cis)-2-[4-(Benzyloxy)-2,3-dihydroxybutyl]benzenepropanoic acid, methyl ester A solution of 4-methyl-morpholine-N-oxide (530 mg, 4.52 mmol) in water (5 mL) was added dropwise to a stirred solution of compound D (1 g, 3.09 mmol) in distilled tetrahydrofuran (20 mL). A few drops of an etheral solution of osmium tetroxide (0.25 g/4 mL of ether) was added. After stirring overnight, the osmate ester was decomposed by addition of an aqueous sodium metabisulfite solution (15 mL). After 15 minutes, the mixture was diluted with ethyl acetate (75 mL) and water (50 mL). The ethyl acetate extract was separated, dried (magnesium sulfate), filtered and concentrated. The residue was chromatographed on a silica gel column and eluted with 10–30% ethyl acetate in hexanes to obtain the title compound (980 mg, 89%).

F. (cis)-2-[[5-(Benzyloxymethyl)-1,3-dioxolan-4-yl]methyl]benzenepropanoic acid, methyl ester A solution of compound E (1.07 g, 3 mmol), N-bromosuccinimide (1.07 g, 6 mmol) in dry dimethylsulfoxide (20 mL) was heated to 58° C. After 8 hours additional N-bromosuccinimide (1.07 g, 6 mmol) was added. The mixture was heated for additional 16 hours cooled and diluted with ethyl acetate (100 mL) and water (100 mL). The ethyl acetate extract was separated, dried (magnesium sulfate), filtered and concentrated. The crude oil was dissolved in methanol (25 mL) and treated with acetyl chloride (1 mL). After 3 hours at room temperature, methanol was removed under reduced pressure. The residue was dissolved in ethyl acetate (75 mL) and washed with satd. NaHCO$_3$ solution (50 mL), dried (magnesium sulfate), filtered and concentrated. The residue was chromatographed on a silica gel column and eluted with 10–30% ethyl acetate in hexanes to obtain the title compound (800 mg, 72%) as a colorless oil.

G. 2-[[5-(Hydroxymethyl)-1,3-dioxolan-4-yl]-methyl]-benzenepropanoic acid, methyl ester Palladium hydroxide on charcoal (160 mg, 20% w/w) was added to a stirred solution of compound F (800 mg, 2.96 mmol) in ethyl acetate (30 mL). The reaction flask was equipped with a hydrogen-filled balloon via three-way stopcock. Air inside the flask was removed under reduced pressure and it was filled with hydrogen from the balloon. This operation was repeated thrice. After 3 hours the balloon was removed, and anhydrous magnesium sulfate was added to the reaction mixture. It was filtered and residual solids were washed with ether (three times). The filtrate was concentrated to obtain the title compound (580 mg, 96%) as an oil.

H. 2-[[5-Carboxy-1,3-dioxolan-4-yl]methyl]-benzenepropanoic acid, methyl ester

A 2.67M solution of Jones reagent in water (1 mL) was added to a stirred solution of compound G (170 mg, 0.61 mmol) in acetone (10 mL) at 0°–5° C. The mixture was stirred at 0°–5° C. for one hour and then at room temperature for 4 hours. Excess Jones reagent was destroyed by addition of isopropanol. The mixture was diluted with ethyl acetate (50 mL) and water (30 mL). The ethyl acetate layer was separated and the aqueous. layer was extracted with ethyl acetate (30 mL). The ethyl acetate extracts were combined, dried (magnesium sulfate), filtered and concentrated to obtain the title compound (160 mg, 90%) as an oil.

I. cis-2-[[5-[[[2-[2-(4-Chlorophenyl)ethyl]-amino]-1-(hydroxymethyl)-2-oxoethyl]amino]-carbonyl]-1,3-dioxolan-4-yl]methyl]benzenepropanoic acid, methyl ester A solution of compound H (430 mg crude, 1.46 mmol), N-hydroxybenztriazole (0.56 g, 4.5 mmol) and (2-p-chlorophenylethylamido)-S-serine hydrochloride (0.558 g, 2 mmol) in dimethylformamide (20 mL) was stirred at 0°–5° C. After 5 minutes, triethylamine (1.7 mL, 12 mmol) was added dropwise. After 30 minutes, 1-(3-dimethylaminopropyl)-3-ethyl carbodiimide hydrochloride (0.63 g, 3.3 mmol) was added. The mixture was stirred at 0° C. to room temperature for 24 hours diluted with ethyl acetate (150 mL) and washed with 1N aqueous hydrochloric acid solution (50 mL, 2x), water (50 mL), dried (magnesium sulfate), filtered and concentrated. The residue was chromatographed on a silica gel column and eluted with ethyl acetate, followed by 2–5% methanol in ethyl acetate to obtain the title compound (0.58 g, 77%) as a mixture of diastereomers.

J. cis-2-[[5-[4-[[[2-(4-Chlorophenyl)ethyl]-amino]-carbonyl]-4,5-dihydro-2-oxazolyl]-1,3-dioxolan-4-yl]methyl]-benzenepropanoic acid, methyl ester Triphenylphosphine (0.98 g, 3.69 mmol) was added to a stirred solution of compound I (580 mg, 1.12 mmol) in acetonitrile (25 mL). After a few min, N,N-diisopropylethyl amine (660 µl, 3.78 mmol) was added. Addition of carbon tetrachloride (1.2 mL) followed. The mixture was stirred for 24 hours diluted with ethyl acetate (150 mL) and washed with saturated sodium bicarbonate solution (50 mL) and brine (50 mL). The organic extract was dried (magnesium sulfate), filtered and concentrated. The residue was chromatographed on a silica gel column and eluted with 50% ethyl acetate in hexanes, followed by 2% and 5% methanol in dichloromethane to obtain the title compound (930 mg), contaminated with triphenylphosphine oxide as a light yellow oil.

K. (cis)-2-[[5-[4-[[[2-(4-Chlorophenyl)ethyl]-amino]-carbonyl]-2-oxazolyl]-1,3-dioxolan-4-yl]methyl]-benzenepropanoic acid, methyl ester Nickel peroxide (500 mg) was added to a stirred solution of compound J (930 mg crude) in dry methylene chloride (20 mL). The mixture was stirred vigorously at room temperature under an argon atmosphere. Additional nickel peroxide (a total of 3 g) was added in 500 mg portions every hour. After 6 hours the mixture was diluted with ethyl acetate (100 mL) and filtered through a pad of anhydrous magnesium sulfate. Residual solids were washed with ethyl acetate (15 mL, 6x). The filtrate was concentrated and the residue was chromatographed on a silica gel column and eluted with 10–30% ethyl acetate in hexanes to obtain (110 mg, 20% overall yield from diamide I) as a colorless oil.

L. (Z)-2-[3-[[[2-(4-Chlorophenyl)ethyl]amino]-carbonyl]-2-oxazolyl]-2-methyl-2-butenyl]-benzenepropanoic acid A solution of lithium hydroxide (82 mg, 2 mmol) in water (2 mL) was added to a stirred solution of compound K (110 mg, 0.22 mmol) in distilled tetrahydrofuran (6 mL). After 6 hours the mixture was diluted with ethyl acetate (50 mL) and washed with 1N hydrochloric acid solution (20 mL). The ethyl acetate extract were dried (magnesium sulfate), filtered and concentrated under reduced pressure and in vacuo to obtain a solid, which was triturated with ether to give Example 16 (55 mg, 51%) as a white solid. Melting point 123°–128° C.

EXAMPLE 17

(+)-(5R-trans)-2-[[5-[4-[[[2-(4-Chlorophenyl)-ethyl]amino]carbonyl]-2-oxazolyl]-1,3-dioxolan-4-yl]methyl]benzenepropanoic acid A. (E)-4-[(Benzyl)oxy]-2-buten-1-ol Alcohol A from Example 16 (4.5 g, 25.2 mmol) was dissolved in dichloromethane (15 mL) and added dropwise to a stirred mixture of pyridinium chlorochromate (8.15 g, 37.8 mmol) and Celite® (8.4 g) in dichloromethane (150 mL). The mixture was stirred at room temperature for 3 hours, then diluted with ethyl acetate (150 mL) and filtered through Celite®. The pad was washed with more ethyl acetate. The filtrate was washed with water (200 mL), dried (magnesium sulfate) and freed of solvent in vacuo. The remaining brown oil was partially dissolved in ethanol (50 mL), cooled in an ice bath, and treated with sodium borohydride (950 mg, 25.2 mmol). The reaction appeared complete by TLC in 5 minutes. The reaction was quenched with saturated ammonium chloride solution and the product was extracted into ethyl acetate (3×100 mL). The combined extracts were dried (magnesium sulfate) and freed of solvent in vacuo. The remaining material was purified by chromatography on silica gel (150 g, Merck), eluting non-polar impurities with 20 % ethyl acetate in hexane and then eluting the desired trans alcohol with ethyl acetate:hexane (1:1) to give alcohol A as a colorless oil (1.765 g, 39%). TLC: $R_f$=0.52, silica gel, ethyl acetate:hexane (1:1), UV and cerium disulfate.

B. (E)-4-(Benzyloxy)-2-butenyl acetate

A stirred solution of alcohol A (1.765 g, 9.9 mmol), and pyridine (2.0 mL, Burdick and Jackson) in dichloromethane (20 mL) was treated with acetic anhydride (2.62 mL, 30 mmol). After 20 hours, the mixture was diluted with ether (120 mL) and washed with water (50 mL), saturated copper sulfate solution (3×50 mL), and water (50 mL), dried (magnesium sulfate), filtered and concentrated in vacuo. The residue was chromatographed on silica gel (60 g, Merck), eluting with 10 and 20% ethyl acetate in hexane to give (2.11 g, 97%) as a colorless oil, which was characterized by NMR. TLC: $R_f$=0.52, silica gel, 20% ethyl acetate in hexane, UV & cerium disulfate.

C. (E)-2-[4-(Benzyloxy)-2-butenyl]benzenepropan-1-ol, dimethylthexylsilyl ether

A suspension of magnesium turnings (832 mg 34.7 mmol) and catalytic iodine in anhydrous tetrahydrofuran (10 mL) was heated under reflux. A few drops of [3-(2-bromophenyl)]-propanol, dimethylthexylsilyl ether was added to initiate the formation of Grignard reagent. Once the iodine color was discharged, additional bromide (a total of 3.86 g, 11.73 mmol) was added portionwise. The mixture was heated under reflux for 90 minutes, cooled to 0° C. in an ice-water bath and was then added via cannula to a solution of acetate B (2.11 g, 9.59 mmol) and a 0.1M solution of dilithium copper tetrachloride (1.53 mL) in tetrahydrofuran (5 mL) at −78° C. The mixture was stirred at −78° C. for 60 minutes and at 0° C. for 90 minutes and quenched with saturated ammonium chloride solution (25 mL). Ether (50 mL) and water (25 mL) were added and the layers were separated. The organic layer was dried (magnesium sulfate), filtered and concentrated. The residue was chromatographed on a silica gel column (60 g, Merck) packed in hexane and eluted with 1–2% ethyl acetate in hexane to obtain silyl ether C (3.16 g, 75%), which was characterized by NMR.

TLC: $R_f$=0.33, silica gel, 5% ethyl acetate in hexane, UV and cerium disulfate.

D. (E)-2-[4-(Benzyloxy)-2-butenyl]benzenepropanoic acid

A solution of silyl ether C (3.165 g, 7.227 mmol) in acetone (25 mL) was treated dropwise at 0°–5° C. with a 2.67M solution of Jones reagent in acetone (5 mL). After 1 hour, the mixture was warmed to room temperature and stirred for an additional 3 hours. Excess Jones reagent was destroyed by addition of isopropanol (5 mL). The mixture was diluted with water (50 mL) and extracted with ethyl acetate (2×100 mL). The ethyl acetate extracts were combined, dried (magnesium sulfate), filtered and concentrated in vacuo to obtain acid D as a yellow oil.

E. (E)-2-[4-(Benzyloxy)-2-butenyl]benzenepropanoic acid, methyl ester

The acid D was dissolved in methanol (20 mL), cooled to 0°–5° C. and acetyl chloride (1 mL) was added dropwise. The mixture was warmed to room temperature and stirred for 2 hours. The mixture was concentrated in vacuo and the residue was chromatographed on a silica gel column 60 g, Merck). Elution with 2 and 5% ethyl acetate in hexane afforded ester E (1.46 g, 62% yield from silyl ether C) as a colorless oil, which was characterized by NMR spectra. TLC: $R_f$=0.53, silica gel, 20% ethyl acetate in hexane, UV and cerium disulfate.

F. (trans)-2-[4-(Benzyloxy)-2,3-dihydroxybutyl]benzenepropanoic acid, methyl ester A solution of 4-methyl-morpholine-N-oxide (773 mg, 6.60 mmol) in water (7.3 mL) was added dropwise to a stirred solution of ester E (1.461 g, 4.51 mmol) in distilled tetrahydrofuran (29 mL). A few drops of an etheral solution of osmium tetroxide (0.25 g/4 mL of ether) was added and the mixture was left stirring overnight at room temperature. The osmate ester was decomposed by addition of an aqueous solution of sodium metabisulfite (25 mL). After 15 minutes, the mixture was diluted with ethyl acetate (100 mL) and water (70 mL). The layers were separated and the aqueous layer was reextracted with ethyl acetate (20 mL). The combined ethyl acetate extracts were dried (magnesium sulfate), filtered and concentrated. The residue was chromatographed on a silica gel column (60 g, Merck), diol F (eluting with 20–50% ethyl acetate in hexane to obtain 1.513 g, 94%) which was characterized by NMR spectra.

TLC: $R_f$=0.38, silica gel, ethyl acetate:hexane (1:1), UV and cerium disulfate.

G. trans-2-[[5-(Benzyloxymethyl)-1,3-dioxolan-4-yl]methyl]benzenepropanoic acid, methyl ester A solution of diol F (1.387 g, 3.87 mmol), N-bromosuccinimide (1.38 g, 7.75 mmol, 2 eq.) in dry dimethylsulfoxide (25 mL, Burdick and Jackson) was heated to 55° C. After 18 hours, additional N-bromosuccinimide (0.69 g, 3.88 mmol, 1 eq) was added. The mixture was heated at 60° for 3 hours, additional N-bromosuccinimide (0.69 g, 1 eq.) was added and heating at 60° C. was continued for an additional 3 hours. The reaction mixture was then cooled and diluted with ethyl acetate (100 mL) and water (100 mL). The ethyl acetate layer was separated, dried (magnesium sulfate), filtered and freed of solvent in vacuo. The crude oil was dissolved in methanol (20 mL), cooled to 0° C. and treated with acetyl chloride (2 mL). The mixture was allowed to warm to room temperature and was stirred 1 hour. The methanol was removed in vacuo. The residue was chromatographed on silica gel (65 g, Merck), eluting with 15% ethyl acetate in hexane to obtain dioxolane G. (977 mg, 68%) as a colorless oil which was characterized by NMR spectra. Starting material (239 mg, 17%) was also isolated during the chromatography by eluting with 50% ethyl acetate in hexane after the desired product was obtained.

H. trans-2-[[5-(Hydroxymethyl)-1,3-dioxolan-4-yl]methyl]benzenepropanoic acid, methyl ester Palladium hydroxide on charcoal (195 mg, 20% w/w) was added to a stirred solution of dioxolane G (977 mg, 2.64 mmol) in ethyl acetate (35 mL). The reaction flask was equipped with a hydrogen filled balloon via a three-way stopcock. Air inside the flask was removed under reduced pressure and it was filled with hydrogen from the balloon. This operation was repeated four times. After 4 hours, the balloon was removed and anhydrous magnesium sulfate was added to the reaction mixture. It was filtered and residual solids were washed with ether (3x). The filtrate was concentrated to obtain alcohol-ester H (700 mg, 100%) as an oil.

I. trans-2-[[5-Carboxy-1,3-dioxolan-4-yl]-methyl]benzenepropanoic acid, methyl ester A 2.67M solution of Jones reagent in water (4.35 mL) was added dropwise to a stirred solution of alcohol H (740 mg, 2.64 mmol) in acetone (43 mL) at 0°–5° C. The mixture was stirred at 0°–5° C. for 1 hour and then at room temperature for 4 hours. Excess Jones reagent was destroyed by addition of isopropanol (4 mL). The mixture was diluted with ethyl acetate (150 mL) and water (75 mL). The ethyl acetate layer was separated and the aqueous layer was reextracted with ethyl acetate (60 mL). The ethyl acetate extracts were combined, dried (magnesium sulfate), filtered and concentrated to obtain acid-ester I (762 mg, 98%) as an oil, which was characterized by NMR spectra and used without purification.

J. trans-2-[[5-[[[2-[[2-(4-Chlorophenyl)-ethyl]amino]-1-(hydroxymethyl)-2-oxoethyl]-amino]carbonyl]-1,3-dioxolan-4-yl]methyl]-benzenepropanoic acid, methyl ester, fast moving isomer (FMI)

K. trans-2-[[5-[[[2-[[2-(4-Chlorophenyl)-ethyl]amino]-1-(hydroxymethyl)-2-oxoethyl]-amino]carbonyl]-1,3-dioxolan-4-yl]methyl]-benzenepropanoic acid, methyl ester, slow moving isomer (SMI)

A solution of acid-ester I (760 mg, 2.58 mmol), N-hydroxybenztriazole (436 mg, 3.23 mmol, 1.25 eq) and (2-p-chlorophenylethylamido)-S-serine hydrochloride (865 mg, 3.1 mmol, 1.2 eq) in dimethylformamide (25 mL, Burdick and Jackson) was stirred at 0°–5° C. After 5 minutes, triethyl amine (0.9 mL, 6.46 mmol, 2.5 eq) was added dropwise. After 30 minutes, 1-(3-dimethylaminopropyl)-3-ethyl carbodiimide hydrochloride (617 mg, 3.23 mmol, 1.25 eq) was added. The mixture was allowed to warm to room temperature and stirred for 24 hours. The reaction was diluted with ethyl acetate (160 mL) and washed with 1N hydrochloric acid solution (2×60 mL) and water (60 mL), dried (magnesium sulfate), filtered and taken to dryness in vacuo. The residue was chromatographed on a silica gel column (65 g, Merck) and eluted with 2% methanol in dichloromethane to give some of the faster moving isomer (238 mg) and the rest of the product was obtained as a mixture of isomers (730 mg). The mixture was rechromatographed on silica gel (65 g, Merck), eluting with 1–4% methanol in dichloromethane to give the fast-moving isomer J, total 415 mg, 31%) and the slow-moving isomer K, 352 mg, 26%) as well as some material of mixed isomers (125 mg, 9%). The samples were characterized by NMR spectra. TLC: $R_f$=0.36 (isomer J) & 0.30 (isomer K), silica gel, ethyl acetate, UV and cerium disulfate.
Rotations: J: $[\alpha]_D$=−8.0° (c=1.3, methanol) K: $[\alpha]_D$=−13.2° (c=1.0, methanol)

L. (+)-trans-2-[[5-[4-[[[2-(4-Chlorophenyl)-ethyl]amino]carbonyl]-4,5-dihydro-2-oxazolyl]-1,3-dioxolan-4-yl]methyl]benzenepropanoic acid, methyl ester Triphenylphosphine (0.68 g, 2.59 mmol, 3.3 eq) was added to a stirred solution of isomer J (407 mg, 0.786 mmol) in acetonitrile (20 mL). After a few min, N,N-diisopropylethylamine (460 µl, 2.65 mmol, 3.4 eq) was added. Dropwise addition of dry carbon tetrachloride (1.0 mL) followed. The mixture was stirred for 2 hours, diluted with ethyl acetate (100 mL) and washed with saturated sodium bicarbonate solution (50 mL) and brine (50 mL). The organic extract was dried (magnesium sulfate), filtered and concentrated in vacuo. The residue was chromatographed on a silica gel column (50 g, Merck), eluting with 15% acetone in toluene to give (378 mg), contaminated with triphenylphosphine oxide. This semi-solid was triturated with cold ether. The solid removed by filtration was triphenylphosphine oxide. The filtrate was taken to dryness in vacuo to give oxazoline L (261 mg, 66%), which was characterized by NMR spectra. TLC: $R_f$=0.6, silica gel, 5% methanol in dichloromethane, UV and cerium disulfate.

M. (+)-trans-2-[[5-[4-[[[2-(4-Chlorophenyl)-ethyl]amino]carbonyl]-2-oxazolyl]-1,3-dioxolan-4-yl]methyl]benzenepropanoic acid, methyl ester Nickel peroxide (250 mg) was added to a stirred solution of oxazoline L (261 mg, maximum of 0.52 mmol) in dry methylene chloride (7 mL). The mixture was stirred at room temperature under an argon atmosphere. Additional nickel peroxide (a total of 800 mg) was added in 100–200 mg portions over a six-hour period. The reaction was nearly complete and was left stirring at room temperature overnight. The mixture was then diluted with ethyl acetate (30 mL) and filtered through a magnesium sulfate pad. The solids were washed with ethyl acetate (4×20 mL). The filtrate was concentrated and the residue was chromatographed on a silica gel column (20 g, Merck) eluting with 20–50% ethyl acetate in hexane to obtain (98 mg, 25% overall yield from amine J) as colorless oil, characterized by NMR spectra.
TLC: $R_f$=0.35, silica gel, ethyl acetate:hexane (1:1), UV and cerium disulfate.

N. (+)-(5R-trans)-2-[[5-[4-[[[2-(4-Chlorophenyl)ethyl]amino]carbonyl]-2-oxazolyl]-1,3-dioxolan-4-yl]methyl] benzenepropanoic acid A solution of lithium hydroxide (82 mg, 2 mmol) in water (2 mL) was added to a stirred solution of Example 17 (98 mg, 0.196 mmol) in distilled tetrahydrofuran (6 mL). After 6.5 hours, the mixture was diluted with ethyl acetate (50 mL) and washed with 1N hydrochloric acid solution (20 mL) and brine (20 mL). The ethyl acetate extract layer was dried (magnesium sulfate), filtered and concentrated in vacuo to obtain a solid which was triturated with ether to give Example 17 (85 mg, 89%) as a white solid.
Melting point 111–115°
C. $[\alpha]_D$=+21.9° (c=0.6, methanol).

EXAMPLE 18

(−)-trans-2-[[5-[4-[[[2-(4-Chlorophenyl)ethyl]-amino]carbonyl]-2-oxazolyl]-1,3-dioxolan-4-yl]-methyl]benzenepropanoic acid A. trans-2-[[5-[4-[[[2-(4-Chlorophenyl)ethyl]-amino]-carbonyl]-4,5-dihydro-2-oxazolyl]-1,3-dioxolan-4-yl]methyl]-benzenepropanoic acid, methyl ester Triphenylphosphine (588 mg, 2.24 mmol, 3.3 eq) was added to a stirred solution of isomer K from Example 17 (352 mg, 0.679 mmol in acetonitrile (18 mL). After a few minutes, N,N-diisopropylethylamine (400 µl, 2.29 mmol, 3.4 eq) was added. Dropwise addition of dry carbon tetrachloride (0.8 mL) followed. The mixture was stirred for 2 hours, diluted with ethyl acetate (100 mL) and washed with saturated sodium bicarbonate solution (50 mL) and brine (50 mL). The organic extract was dried (magnesium sulfate), filtered and concentrated in vacuo. The residue was chromatographed on a silica gel column (50 g, Merck), eluting with 8–15% acetone in toluene to give oxazoline A (390 mg), contaminated with triphenyl phosphine oxide. The material was characterized by NMR spectra.
TLC: $R_f$=0.6, silica gel, 5% methanol in dichloromethane, UV and cerium disulfate.

B. (−)-trans-2-[[5-[4-[[[2-(4-Chlorophenyl)-ethyl]amino]-carbonyl]-2-oxazolyl]-1,3-dioxolan-4-yl]methyl] benzenepropanoic acid, methyl ester Nickel peroxide (250 mg) was added to a stirred solution of oxazoline A (390 mg) in dry methylene chloride (7 mL). The mixture was stirred at room temperature under an argon atmosphere. Additional nickel peroxide (a total of 800 mg) was added in 100–200 mg portions over a six-hour period. The reaction was nearly complete and was left stirring at room temperature overnight. The mixture was then diluted with ethyl acetate (30 mL) and filtered through a magnesium sulfate pad. The solids were washed with ethyl acetate (5×20 mL). The filtrate was concentrated and the residue was chromatographed on a silica gel column (20 g, Merck), eluting with 20–40% ethyl acetate in hexane to obtain ester B (111 mg, 33% overall yield from K in Example 17) as a colorless oil, characterized by NMR spectra.
TLC: $R_f$=0.35, silica gel, ethyl acetate:hexane (1:1), UV and cerium disulfate.

C. (−)-trans)-2-[[5-[4-[[[2-(4-Chlorophenyl)-ethyl]amino]carbonyl]-2-oxazolyl]-1,3-dioxolan-4-yl]methyl]benzenepropanoic acid, A solution of lithium hydroxide (82 mg, 2 mmol) in water (2 mL) was added to a stirred solution of ester B (111 mg, 0.22 mmol) in distilled tetrahydrofuran (6 mL). After 7 hours, the mixture was diluted with ethyl acetate (50 mL) and washed with 1N hydrochloric acid solution (20 mL) and brine (20 mL). The ethyl acetate extract layer was dried (magnesium sulfate), filtered and concentrated in vacuo to obtain a solid which was triturated with ether to give Example 18 (97 mg, 91%) as a white solid.
Melting poiunt: 111°–118° C.
$[\alpha]_D = -18.90°$ (c=0.55, methanol).

EXAMPLE 19

(2α,4α,5α)-2-[[5-[4-[[[2-(4-Chlorophenyl)ethyl]-amino]carbonyl]-2-oxazolyl]-2-methyl-1,3-dioxolan-4-yl]methyl]benzenepropanoic acid A. 2-(2-Hydroxymethyl)phenylethan-1-ol A solution of homophthalic anhydride (6.21 g, 38.3 mmol) in dry tetrahydrofuran (100 mL) was added dropwise to a stirred suspension of lithium aluminum hydride (2.18 g, 57.5 mmol) in tetrahydrofuran (60 mL) at 0° C. The suspension was stirred at 0° C. to room temperature overnight. Excess lithium aluminum hydride was destroyed by careful addition of freshly prepared saturated sodium sulfate solution in water. Addition was continued until all inorganics were precipitated as white solids. Anhydrous magnesium sulfate was added and the mixture was filtered. The filtrate was concentrated under reduced pressure and the residual oil was chromatographed on a silica gel column. Elution with 20–75% ethyl acetate in hexanes afforded diol A (3.05 g, 52%) as an oil.

B. 2-[2-(Hydroxymethyl)phenyl]thexylsilyloxyethane

A solution of diol A (13.39 g, 88.1 mmol) in tetrahydrofuran (120 mL) was added dropwise to a stirred suspension of sodium hydride (2.33 g, 96.9 mmol) in tetrahydrofuran (250 mL), cooled at 0°–5° C. in an ice-water bath. After addition the mixture was warmed to room temperature and stirred for 30 min. It was cooled to 0°–5° C. and dimethylthexylsilyl chloride (20.47 g, 114.5 mmol) was added dropwise. After stirring overnight, excess sodium hydride was destroyed by addition of 5% aqueous sodium bicarbonate solution. The white precipitate was filtered and the layers were separated. The aqueous layer was extracted with ether (twice). The organic extracts were combined, dried (magnesium sulfate), filtered and concentrated. The residue was chromatographed on a silica gel column and eluted with hexanes, followed by 2–5% ethyl acetate in hexanes to obtain silyl ether B (9.89 g, 38%).

C. 2-(2-Formylphenyl)thexylsilyloxyethane

Pyridinum dichromate (18.9 g, 50.25 mmol) was added to a stirred suspension of silyl ether B (9.87 g, 33.5 mmol) and Celite® (18.9 g) in dichloromethane (280 mL). After 6 hours, the mixture was diluted with ether (350 mL) and filtered through anhydrous magnesium sulfate. Residual solids were washed with ether (three times). The filtrate was concentrated under reduced pressure and the residual oil was chromatographed on a silica gel column. Elution with 20% ethyl acetate in hexanes afforded aldehyde C (9.05 g, 92%).

D. 4-[2-[(2-Thexylsilyloxy)ethyl]benzene]-prop-2-enoic acid, methyl ester

Methyl(triphenylphosphoranylidene) acetate (12.38 g, 37.1 mmol) was added to a stirred solution of aldehyde C (9.03 g, 30.9 mmol) in methanol (300 mL) at 0°–5° C. After 2.5 hours, solvents were removed by distillation under reduced pressure. The residual solid was triturated with ether and filtered. the filtrate was concentrated under reduced pressure and the residue was chromatographed on a silica gel column. Elution with 10% ethyl acetate in hexanes afforded olefin ester D (9.14 g, 85%) as a mixture of E- and Z-isomers.

E. 4-[2-[(2-Thexylsilyloxy)ethyl]benzene]-propanoic acid, methyl ester

Palladium hydroxide on charcoal (900 mg, 10% w/w) was added to a stirred solution of olefin ester D (9.11 g, 26.16 mmol) in ethyl acetate (250 mL). The reaction flask was equipped with a hydrogen filled balloon via three-way stopcock. Air inside the flask was removed under reduced pressure and it was filled with hydrogen from the balloon. This operation was repeated thrice. After 24 hours, the balloon was removed and anhydrous magnesium sulfate was added to the reaction mixture. It was filtered and residual solids were washed with ether. The filtrate was concentrated to obtain sidechain-saturated ester E (9.08 g, 99%) as a colorless oil.

F. 3-[2-[(2-Thexylsilyloxy)ethyl]benzene]-propanol

A solution of ester E (5.00 g, 14.27 mmol) in dry tetrahydrofuran (60 mL) was added dropwise to a stirred suspension of lithium aluminum hydride (0.54 g, 14.27 mmol) in tetrahydrofuran (40 mL) at 0° C. The suspension was stirred at 0° C. to room temperature for 3 hours. Excess lithium aluminum hydride was destroyed by careful addition of freshly prepared saturated sodium sulfate solution in water. Addition was continued until all inorganics were precipitated as white solids. Anhydrous magnesium sulfate was added and the mixture was filtered. The filtrate was concentrated under reduced pressure to obtain alcohol F (4.76 g, 100% crude) as an oil.

G. 3-[2-[(2-Thexylsilyloxy)ethyl]benzene]-propanol, t-butyldimethylsilyl ether

A solution of alcohol F (4.73 g, 14.27 mmol) in dichloromethane (65 mL) was treated with triethylamine (8.2 mL, 58.68 mmol), 4-dimethylamino pyridine (366 mg, 3 mmol) and t-butyldiphenyl-chlorosilane (4.84 g, 17.61 mmol). After 2.5 hours, the mixture was diluted with ether (200 mL) and washed with 5% aqueous sodium bicarbonate solution (twice). The combined aqueous layer was extracted with ether (twice). The combined ether extracts were dried (magnesium sulfate), filtered and concentrated. The residue was chromatographed on a silica gel column and eluted with hexanes, followed by 5% ethyl acetate in hexanes to obtain diprotected compound G (7.53 g, 94% overall yield from E) as a colorless oil.

H. 2-[2-[(3-t-Butyldimethylsilyloxy)propyl]-benzene]ethanol

A solution of diprotected compound G (7.53 g, 13.43 mmol) in acetone (300 mL) was treated dropwise at 0° C. with a 0.5N aqueous hydrochloric acid solution (37 mL). After 30 minutes at 0° C. and 6 hours at room temperature, the mixture was diluted with ethyl acetate (200 mL) and washed with 5% aqueous sodium bicarbonate solution (twice). The aqueous layer was extracted with ethyl acetate (twice). The ethyl acetate extracts were combined, dried (magnesium sulfate), filtered and concentrated. The residual oil was chromatographed on a silica gel column and eluted with 10–20% ethyl acetate in hexanes to obtain alcohol H (4.44 g, 79%) as an oil.

I. 2-[2-[(3-t-Butyldimethylsilyloxy)propyl]-benzene] acetaldehyde

Pyridinium dichromate (6.0 g, 15.91 mmol) was added to a stirred suspension of alcohol H (4.44 g, 10.61 mmol) and Celite® (6 g) in dichloromethane (90 mL). After overnight, the mixture was diluted with ether (200 mL) and filtered through anhydrous magnesium sulfate. Residual solids were washed with ether (three times). The filtrate was concentrated under reduced pressure and the residual oil was chromatographed on a silica gel column. Elution with 2–5% ethyl acetate in hexanes afforded aldehyde I (2.53 g, 57%).

J. 4-[2-[(3-t-Butyldimethylsilyloxy)propyl]-benzene]-Z-but-2-enoic acid, methyl ester A 0.67M solution of potassium hexamethyldisilazane (1.67 mL, 1 mmol) in toluene was added dropwise to a stirred solution of bis(2,2,2-trifluoroethyl) (methoxycarbonylmethyl)phosphonate (318 mg, 1 mmol) and 1,4,7,10,13,16-hexaoxacyclooctadecane (1.32 g, 5 mmol) in tetrahydrofuran (20 mL) at −78° C. A solution of aldehyde I (416 mg, 1 mmol) in tetrahydrofuran (3 mL) was added. The mixture was stirred at −78° C. for one hour and then quenched with saturated aqueous ammonium chloride solution. The mixture was diluted with water and extracted with ether (three times). The ether extract was dried (sodium sulfate), filtered and concentrated. The crude oil was chromatographed on a silica gel column and eluted with 2–4% ethyl acetate in hexanes to obtain olefin ester J (300 mg, 64%).

K. 4-[2-[(3-t-Butyldimethylsilyloxy)propyl]-benzene-2,3-dihydroxybutanoic acid, methyl ester A solution of N-methylmorpholine-N-oxide (300 mg, 2.54 mmol) in water (2 mL) was added to a stirred solution of olefin ester J (750 mg, 1.59 mmol) in tetrahydrofuran (10 mL). A few drops of an etheral solution of osmium tetroxide (0.25 g in 4 mL of ether) was added. After 24 hours, additional etheral solution of osmium tetroxide (4 drops) was added and the mixture was stirred for an additional 24 hours. A saturated solution of sodium metabisulfite (20 mL) was added and stirred for 10 minutes. The mixture was diluted with ethyl acetate and the layers were separated. The aqueous layer was extracted with ethyl acetate (twice). The combine ethyl acetate extracts were dried (magnesium sulfate), filtered and concentrated. the residue was chromatographed on a silica gel column and eluted with 20–50% ethyl acetate in hexanes to obtain diol K (590 mg, 74%).

L. (2α,4α,5α)-2-[5-[4-Carbomethoxy-2-methyl-1,3-dioxolan-4-yl]methyl]benzenebutanol, t-butyldiphenylsilyl ether A solution of diol K (590 mg, 1.16 mmol) in dry toluene (4 mL) was treated with acetaldehyde (0.65 mL, 11.65 mmol) and catalytic p-toluene-sulfonic acid at 0° C. After 48 hours, the mixture was diluted with ethyl acetate (60 mL) and washed with 5% aqueous sodium bicarbonate solution. The ethyl acetate extract was dried (magnesium sulfate), filtered and concentrated. The residue was chromatographed on a silica gel column and eluted with 20% ethyl acetate in hexanes to obtain dioxolane L (420 mg, 69%).

M. (2α,4α,5α)-2-[5-[4-Carboxy-2-methyl-1,3-dioxolan-4-yl]methyl]benzenebutanol,t-butyl-diphenylsilyl ether A solution of lithium hydroxide (100 mg, 2.39 mmol) in water (4 mL) was added to a stirred solution of dioxolane L (400 mg, 0.75 mmol) in distilled tetrahydrofuran (16 mL). After 2.5 hours the mixture was acidified with 1N hydrochloric acid solution to pH 7 at 0° C. and extracted with ethyl acetate (three times). The ethyl acetate extracts were combined, washed with brine, dried (magnesium sulfate), filtered and concentrated under reduced pressure to obtain acid M (380 mg, 100%).

N. (2α,4α,5α)-N-(4-Chlorophenyl)ethyl]-N-2-[[5-[[2-[2-[[(1,1-dimethylethyl)-diphenyl silyl]oxy]ethyl]phenyl] methyl]-2-methyl-1,3-dioxolan-4-yl]carbonyl]-L-serinamide A solution of acid M (380 mg, 0.73 mmol), N-hydroxybenztriazole (150 mg, 1.09 mmol) and (2-p-chlorophenylethylamido)-S-serine hydrochloride (300 mg, 1.09 mmol) in dimethylformamide (10 mL) was stirred at 0°–5° C. After a few minutes, triethyl amine (510 ml, 3.65 mmol) was added dropwise. After 5 minutes, 1-(3-dimethylaminopropyl)-3-ethyl carbodiimide hydrochloride (210 mg, 1.09 mmol) was added. The mixture was stirred at 0° C. to room temperature overnight, diluted with ethyl acetate and washed with 1N aqueous hydrochloric acid solution, saturated sodium bicarbonate solution. The ethyl acetate extract was dried (magnesium sulfate), filtered and concentrated. The residue was chromatographed on a silica gel column and eluted with 2% and 4% methanol in dichloromethane to obtain diamide N (380 mg, a mixture of diastereomers, 70%).

O. (2α,4α,5α)-2-[[5-[4-[[[2-(4-Chlorophenyl)-ethyl]-amino]carbonyl]-4,5-dihydro-2-oxazolyl]-2-methyl-1,3-dioxan-4-yl]methyl]-benzenebutanol, t-butyldiphenylsilyl ether Triphenylphosphine (400 mg, 1.54 mmol) was added to a stirred solution of diamide N (380 mg, 0.51 mmol) in acetonitrile (7.5 mL). After a few minutes, N,N-diisopropylethyl amine (280 µL, 1.58 mmol) was added. Addition of carbon tetrachloride (500 µL) followed. The mixture was stirred for 2.5 hours, diluted with ethyl acetate (60 mL) and washed with 5% aqueous sodium bicarbonate solution and brine. The organic extract was dried (magnesiun sulfate), filtered and concentrated. The residue was chromatographed on a silica gel column and eluted with 0.5% and 1% methanol in dichloromethane to obtain oxazoline O (240 mg, 65%) as a mixture of diastereomers.

P. (2α,4α,5α)-2-[[5-[4-[[[2-(4-Chlorophenyl)-ethyl]-amino]carbonyl]-2-oxazolyl]-2-methyl-1,3-dioxan-4-yl] methyl]benzenebutanol, t-butyldiphenylsilyl ether Nickel peroxide (240 mg) was added to a stirred solution of oxazoline O (240 mg, 0.33 mmol) in dry methylene chloride (4.5 mL). The mixture was stirred vigorously at room temperature under an argon atmosphere. Additional nickel peroxide (a total of 1.24 g) was added in 200-mg portions every hour. After overnight, the mixture was diluted with ethyl acetate (75 mL) and washed with a 3M solution of sodium bisulfite (50 mL). The ethyl acetate layer was separated, washed with 1M trisodium citrate solution (50 mL) and brine (50 mL). The organic layer was dried (magnesium sulfate), filtered and concentrated. The crude residue was chromatographed on a silica gel column and eluted with 20% and 30% ethyl acetate in hexanes to afford silyl ether P (79 mg, 32%).

Q. (2α,4α,5α)-2-[[5-[4-[[[2-(4-Chlorophenyl)-ethyl] amino]carbonyl]-2-oxazolyl]-2-methyl-1,3-dioxan-4-yl] methyl]benzenebutanol A solution of silyl ether P (109 mg, 0.15 mmol) in tetrahydrofuran (3 mL) was treated dropwise with a 1M solution of tetra-n-butylammonium fluoride in tetrahydrofuran (1 mL) at 0°–5° C. After 3 hours the mixture was diluted with ethyl acetate (75 mL) and washed with brine (50 mL) and water (50 mL). The ethyl acetate extract was dried (magnesium sulfate), filtered and concentrated. The residue was chromatographed on a silica gel column and eluted with 30%, followed by 50% ethyl acetate in hexanes to obtain alcohol Q (52 mg, 71%) as a colorless oil.

R. (2α,4α,5α)-2-[[5-[4-[[[2-(4-Chlorophenyl)-ethyl]amino]carbonyl]-2-oxazolyl]-2-methyl-1,3-dioxan-4-yl]methyl]benzenepropanoic acid A solution of alcohol Q (52 mg, 0.11 mmol) in acetone (3 mL) was treated dropwise at 0°–5° C. with a 2.67M solution of Jones reagent in acetone (0.5 mL). After 2 hours, excess Jones reagent was destroyed by addition of isopropanol at 0°–5° C. The mixture was diluted with ethyl acetate (75 mL) and water (50 mL). The ethyl acetate layer was separated, washed with water (25 mL), dried (magnesium sulfate), filtered and concentrated to obtain a colorless oil, which was diluted with ether (5 mL), and the precipitated white solid was filtered, washed with ether (twice) and dried in vacuo to obtain Example 19 (32 mg, 60%) as a white solid. Melting point 171°–175° C.

EXAMPLE 20

[2α,4α,5α(Z)]-6-[2-(2-Chlorophenyl)-4-[4-[[(4-cyclohexylbutyl)aminocarbonyl]-2-oxazolyl]-1,3-dioxan-5-yl]-4-hexenoic acid A. 2-Allyl-4-(benzyloxy)-3-hydroxy-1-butanol and B. 3-Allyl-4-(benzyloxy)-3-hydroxy-1-butanol A solution of 4-benzyloxy-2,3-epoxy-1-butanol (6.28 g, 32.37 mmol) in anhydrous tetrahydrofuran (75 mL) was added dropwise at −40° C. over a period of 45 minutes, to a 2M solution of allyl magnesium chloride (48.5 mL, 97 mmol) and tetrahydrofuran (50 mL). The solution was stirred at −40° C. for 1 hour, warmed to 0° C. and quenched by addition of aqueous ammonium chloride solution. The tetrahydrofuran layer was separated and the aqueous layer was extracted with ethyl acetate (three times). The combined organic extract was dried (magnesium sulfate), filtered and concentrated to obtain a mixture of compounds A and B.

C. (5α,6α)-5-Allyl-6-(benzyloxymethyl)-2,2-dimethyl-1,3-dioxane 2,2-Dimethoxypropane (12 mL, 97 mmol) was added with stirring to a solution of crude diols A and B, catalytic p-toluenesulfonic acid in acetone (50 mL). The mixture was stirred at room temperature overnight, diluted with ether and washed with aqueous sodium bicarbonate solution (twice). The organic extract was dried (magnesium sulfate), filtered and concentrated. The crude oil was chromatographed on a silica gel column and eluted with 2–10% ethyl acetate in hexanes to obtain dioxane C (5.85 g, 65% overall yield from 4-benzyloxy-2,3-epoxy-1-butanol) as a colorless oil.

D. (5α,6α)-6-(Benzyloxymethyl)-5-(2,3-dihydroxypropyl)-2,2-dimethyl-1,3-dioxane

A solution of dioxane C (4.3 g, 15.58 mmol) in tetrahydrofuran (75 mL) was treated dropwise with an aqueous solution of 4-morpholine-N-oxide (2.73 g, 23.37 mmol in 10 mL water) and catalytic osmium tetroxide. After 24 hours, the mixture was treated with saturated sodium bisulfite solution (50 mL) and ethyl acetate (100 mL). The ethyl acetate extract was separated and the aqueous layer was extracted with ethyl acetate (twice). The combined extract was dried (magnesium sulfate), filtered and concentrated to obtain crude diol D (4.27 g, 88%) as an oil.

E. (5α,6α)-6-(Benzyloxymethyl)-5-(formyl-methyl)-2,2-dimethyl-1,3-dioxane

A solution of crude diol D (4.27 g, 13.77 mmol) in methanol (100 mL) was treated dropwise at 0°–5° C. with a solution of sodium periodate (3.68 g, 17.22 mmol) in water (30 mL). After 1 hour, the precipitated solids were filtered and washed with ether. The filtrate was washed with aqueous sodium bicarbonate solution (twice) and brine. The aqueous extracts were combined and extracted with ether (twice). The combined ether extracts was dried (magnesium sulfate), filtered and concentrated. The crude oil was chromatographed on a silica gel column and eluted with 5–20% ethyl acetate in hexanes to obtain aldehyde E (3.25 g, 85%) as an oil.

F. (5α,6α)-5-(Formylmethyl)-6-(hydroxymethyl)-2,2-dimethyl-1,3-dioxane

Palladium hydroxide (650 mg, 20% w/w) was added with stirring to a solution of aldehyde E (3.25 g, 11.69 mmol) in ethyl acetate (100 mL). The flask was equipped with a hydrogen-filled balloon via a three-way stopcock. Air inside the flask was evacuated under reduced pressure and was then filled with hydrogen from the balloon. This operation was repeated thrice. After 3 hours, the balloon was removed and the reaction mixture was filtered through a pad of anhydrous potassium carbonate. Solids were washed with ethyl acetate (three times). The combined filtrate was concentrated to obtain crude dioxane F (1.98 g, 90%) as an oil.

G. [5α(Z),6α]-6-(Hydroxymethyl)-5-[5-(methoxycarbonyl)-2-pentenyl]-2,2-dimethyl-1,3-dioxane A suspension of carboxybutyltriphenylphosphonium bromide (13.55 g, 31.59 mmol) in dry tetrahydrofuran (150 mL) was treated dropwise with a 1.8M solution of potassium-tert-amylate in toluene (35.2 mL, 63.36 mmol) at 0°–5° C. The yellow-orange suspension was stirred for 1 hour at 0°–5° C and a solution of dioxane F (1.98 g, 10.53 mmol) in tetrahydrofuran (25 mL) was added dropwise. The suspension was stirred at 0° C. to room temperature for 3 hours and was then quenched by addition of water (150 mL). The organic layer was separated and the aqueous. layer was extracted with ethyl acetate (twice). The aqueous layer was carefully acidified to pH 4–5 by addition of 0.5N hydrochloric acid solution at 0°–5° C. The acidified aqueous layer was extracted with ethyl acetate (three times) and the extracts were dried (magnesium sulfate), filtered and concentrated. The white residue was suspended in ethyl acetate/ether (1:5, 90 mL) and filtered. The filtrate was cooled in an ice-water bath and treated with an etheral diazomethane solution with stirring until the yellow color persisted. After 30 minutes, excess diazomethane was removed by bubbling argon through the solution. The solution was concentrated and the residue was chromatographed on a silica gel column. Elution with 5–25% ethyl acetate in hexanes afforded alcohol-ester G (1.45 g, 51%) as a colorless oil.

H. [5α(Z),6α]-6-(t-Butyldiphenylsilyloxymethyl)-5-[5-methoxycarbonyl-2-pentenyl]-2,2-dimethyl-1,3-dioxane A solution of alcohol-ester G (1.3 g, 4.78 mmol), triethylamine (2.8 mL, 20 mmol) and 4-dimethylaminopyridine (122 mg, 1 mmol) in dry dichloromethane (20 mL) was treated dropwise with tert-butyldiphenylchlorosilane (2 g, 7 mmol). After 4 hours, the reaction mixture was diluted with ether (100 mL) and washed with 5% aqueous sodium bicarbonate solution (twice). The aqueous layers were combined, extracted with ether (twice). The combined ether extract was dried (magnesium sulfate), filtered and concentrated. The residue was chromatographed on a silica gel column and eluted with 5–20% ethyl acetate in hexanes to obtain silyl ether-ester H (2.5 g, containing some t-butyldiphenylsilanol) as an oil.

I. [2α,5α(Z),6α]-6-(t-Butyldiphenylsilyloxymethyl)-2-(2-chlorophenyl)-5-[5-(methoxycarbonyl)-2-pentenyl]-1,3-dioxane A solution of silyl ether-ester H (510 mg, 1 mmol) in dry toluene (3 mL) was treated with 2-chlorobenzaldehyde (580 mg, 4 mmol) and catalytic p-toluenesulfonic acid. After 4 hours, the mixture was diluted with ethyl acetate (75 mL) and washed with 5% aqueous sodium bicarbonate solution. The ethyl acetate extract was dried (magnesium sulfate), filtered and concentrated. The residue was chromatographed on a silica gel column and eluted with 2–5% ethyl acetate in hexanes to obtain chlorophenyl compound I (587 mg, 98%) as an oil.

J. [2α,5α(Z),6α]-[2-(2-Chlorophenyl)]-6-(hydroxymethyl)-5-[5-(methoxycarbonyl)-2-pentenyl]-1,3-dioxane A solution of compound I (587 mg, 0.98 mmol) in tetrahydrofuran (8 mL) was treated dropwise with a 1M solution of tetra-n-butylammonium fluoride in tetrahydrofuran (1.2 mL) at 0°–5° C. After 1.5 hours, the mixture was diluted with ether (75 mL) and washed with brine. The ether extract was dried (magnesium sulfate), filtered and concentrated. The residue was chromatographed on a silica gel column and eluted with 20%, followed by 50% ethyl acetate in hexanes to obtain alcohol-ester J (320 mg, 93%) as an oil.

K. [2α,5α(Z),6α]-6-Carboxy-[2-(2-chlorophenyl)]-5-[5-(methoxycarbonyl)-2-pentenyl]-1,3-dioxane A solution of alcohol-ester J (320 mg, 0.9 mmol) in acetone (5 mL) was treated dropwise with stirring with a 2.67M solution of Jones reagent in acetone (3 mL) at 0°–5° C. The mixture was stirred at 0°–5° C. for 15 minutes and at room temperature for 3 hours. Excess Jones reagent was destroyed by addition of isopropanol. The reaction mixture was partitioned between ethyl acetate and water. The The aqueous layer was extracted with ethyl acetate (twice). The combined organic extract was dried (magnesium sulfate), filtered and concentrated to obtain crude acid-ester K (385 mg) as an oil.

L. [2α,5α(Z),6α]-6-[2-(2-Chlorophenyl)-4-[[[2-[(4-Cyclohexylbutyl)amino]-1-(hydroxymethyl)-2-oxoethyl]amino]carbonyl]-1,3-dioxan-5-yl]-4-hexenoic acid, methyl ester A solution of acid-ester K (385 mg crude, 0.9 mmol), N-hydroxybenzotriazole (375 mg, 2.25 mmol) and (4-cyclohexylbutylamido)-S-serine hydrochloride (545 mg, 1.96 mmol) in dimethylformamide (20 mL) was stirred at 0–5° C. for 5 minutes. Triethylamine (660 mg, 6.54 mmol) was added dropwise. After 25 minutes, 1-(3-dimethylaminopropyl)-3-ethyl carbodiimide hydrochloride (420 mg, 2.18 mmol) was added. The mixture was stirred at 0° C. to room temperature for 18 hours, diluted with ethyl acetate (50 mL) and washed with 1N aqueous hydrochloric acid solution (50 mL), water (50 mL), 5% aqueous sodium bicarbonate solution (50 mL). The ethyl acetate extract was dried (magnesium sulfate), filtered and concentrated. The residue was chromatographed on a silica gel column and eluted with 20–75% ethyl acetate in hexanes to obtain diamide L (340 mg, a mixture of diastereomers contaminated with an unknown UV active product).

M. [2α,5α(Z),6α]-6-[2-(2-Chlorophenyl)-4-[4-[[(4-cyclohexylbutyl)amino]carbonyl]-4,5-dihydro-2-oxazolyl]-1,3-dioxan-5-yl]-4-hexenoic acid, methyl ester Triphenylphosphine (301 mg, 1.15 mmol) was added with stirring to a solution of diamide L (340 mg, about 0.57 mmol) in acetonitrile (6 mL). After a few minutes, N,N-diisopropylethyl amine (220 ml, 1.26 mmol) was added. Addition of carbon tetrachloride (400 ml) followed. The mixture was stirred for 8 hours, diluted with ethyl acetate (50 mL) and washed with aqueous sodium bicarbonate solution and brine. The organic extract was dried (magnesium sulfate), filtered and concentrated. The residue was chromatographed on a silica gel column and eluted with 20–75% ethyl acetate in hexanes to obtain oxazoline M (172 mg, 52% overall yield from 11) as a mixture of diastereomers.

N. (2α,5α(Z),6α)-6-[2-(2-Chlorophenyl)-4-[4-[[(4-cyclohexylbutyl)amino]carbonyl]-2-oxazolyl]-1,3-dioxan-5-yl]-4-hexenoic acid, methyl ester Nickel peroxide (127 mg) was added with stirring to a solution of oxazoline M (127 mg, 0.22 mmol) in dry methylene chloride (3 mL). The mixture was stirred vigorously at room temperature under an argon atmosphere. Additional nickel peroxide (a total of 927 mg) was added in 100-mg portions every hour. After 8.5 hours, the mixture was diluted with ethyl acetate (75 mL) and washed with a 3M solution of sodium bisulfite (75 mL). The ethyl acetate layer was separated, washed with 1M trisodium citrate solution (2x 50 mL), water (50 mL) and brine (50 mL). The organic layer was dried (magnesium sulfate), filtered and concentrated. Crystallization from ether at −20° C. afforded ester N (34 mg) as a white solid. The mother liquor was chromatographed on 0.25 mm silica gel plates (eluting solvent 30% ethyl acetate in hexanes) to obtain additional ester N (20 mg).

O. [2α,5α(Z),6α]-6-[2-(2-Chlorophenyl)-4-[4-[[(4-cyclohexylbutyl)amino]carbonyl]-2-oxazolyl]-1,3-dioxan-5-yl]-4-hexenoic acid A 1M solution of lithium hydroxide in water (2 mL, 2 mmol) was added with stirring to a solution of ester N (33 mg, 0.058 mmol) in distilled tetrahydrofuran (4 mL). After 8 hours, the mixture was diluted with ethyl acetate (30 mL) and 0.5N hydrochloric acid solution (15 mL). The aqueous layer was extracted with ethyl acetate (30 mL). The ethyl acetate extracts were combined, washed with water, and brine, dried (magnesium sulfate), filtered and concentrated. The residual oil was triturated with hexanes to obtain a white solid (30 mg) which was washed with ether (5 mL) and dried in vacuo to obtain Example 20 (22.5 mg, 69.9% yield). Melting point 115°–123° C.

$^1$H NMR (CDCl$_3$): δ 8.2 (s, 1H), 7.8 (dd, 1H), 7.2–7.4 (m, 4H), 7.0 (t,1H), 6.1 (s, 1H), 5.4 (m, 3H), 4.3 (d, 1H), 4.2 (d, 1H), 3.4 (m, 2H), 2.8 (m, 1H), 2.4 (bs, 4H), 2.0 (m, 2H), 1.7 (m, 6H), 1.3 (m, 8H), 0.9 (m, 2H).

$^{13}$C NMR (CDCl$_3$): δ 178.1, 161.0, 141.7, 136.8, 131.0, 130.7, 129.9, 128.7, 128.4, 127.6, 100.2, 76.5, 69.9, 39.7, 38.1, 38.0, 37.5, 34.2, 33.8, 30.3, 27.1, 26.8, 24.7, 23.8, 23.1.

EXAMPLE 21

(2α,5α,6α)-2-[[2-(2-Chlorophenyl)-4-[4-[[(4-cyclohexylbutyl)amino]carbonyl]-2-oxazolyl]-1,3-dioxan-5-yl]methyl]benzenepropanoic acid A. 4-(Benzyloxy)-3-[[2-(4,4-dimethyl-2-oxazolinyl)phenyl]methyl]-1,2-butanediol A solution of 2-(2-methylphenyl)-4,4-dimethyl-2-oxazoline (5.46 g, 28.9 mmol) in anhydrous tetrahydrofuran (75 mL) at 0° C. was treated dropwise with a 2.5M solution of n-butyl lithium in hexanes (10.3 mL, 25.8 mmol). The bright red solution was stirred at 0° C. for 20 minutes, cooled to −40° C. in a dry ice-acetone bath and a solution of 4-benzyloxy-2,3-epoxy-1-butanol (2 g, 10.3 mmol) in tetrahydrofuran (10 mL) was added. After 1 hour at −40° C., the mixture was warmed to −10° C. over a period of 1 hour and was then quenched with aqueous ammonium chloride solution. The tetrahydrofuran layer was separated and the aqueous layer was extracted with ethyl acetate (three times). The extracts were combined, dried (magnesium sulfate), filtered and concentrated. The crude oil was chromatographed on a silica gel column and eluted with 15–30% ethyl acetate in hexanes to obtain oxazoline diol A (2.23 g, 56%) as an oil.

B. 4-(Benzyloxy)-3-[[2-(carbomethoxy)phenyl]-methyl]-1,3-butanediol

A solution of oxazoline diol A (3 g, 7.83 mmol) in anhydrous methanol (30 mL) was treated at 0°–5° C. with acetyl chloride (3.2 mL). After 5 minutes, the ice bath was removed and the mixture was heated under reflux for 6 hours. The reaction mixture was cooled and the solvent was removed under reduced pressure. The residue was chromatographed on a silica gel column and eluted with 5–60% ethyl acetate in hexanes to obtain diol ester B (1.57 g, 58%) as a colorless oil.

C. (5α,6α)-2-[[6-(Benzloxymethyl)-2,2-dimethyl-1,3-dioxan-5-yl]methyl]benzoic acid, methyl ester Catalytic amount of p-toluenesulfonic acid was added to a stirred solution of diol ester B (2.08 g, 6.05 mmol) in 2,2-dimethoxypropane (10 mL). The mixture was stirred overnight, diluted with ethyl acetate (200 mL) and washed with aqueous sodium bicarbonate solution. The ethyl acetate extract was separated, dried (magnesium sulfate), filtered and concentrated. The residual oil was chromatographed on a silica gel column and eluted with 5–20% ethyl acetate in hexanes to obtain dioxane ester C (1.85 g, 80%) as an oil.

D. (5α,6α)-2-[[6-(Benzyloxymethyl)-2,2-dimethyl-1,3-dioxan-5-yl]methyl]benzenemethanol A solution of dioxane ester C (1.85 g, 4.82 mmol) in anhydrous tetrahydrofuran (10 mL) was added with stirring at 0°–5° C. to a suspension of lithium aluminum hydride (380 mg, 10 mmol) in tetrahydrofuran (40 mL). After this addition, the cooling bath was removed and the mixture was stirred at room temperature overnight. The reaction mixture was cooled on an ice-water bath and treated dropwise with a saturated aqueous sodium sulfate solution. Addition was continued until all salts were precipitated as white granular solids. Anhydrous magnesium sulfate was added and the reaction mixture was filtered. Solids were washed with ethyl acetate. The filtrate was concentrated and the residue was chromatographed on a silica gel column. Elution with 10–30% ethyl acetate in hexanes afforded alcohol D (1.33 g, 77%) as a colorless oil.

E. (5α,6α)-2-[[6-(Benzyloxymethyl)-2,2-dimethyl-1,3-dioxan-5-yl]methyl]benzaldehyde Pyridinium dichromate (2.9 g, 7.7 mmol) was added to a stirred suspension of alcohol D (1.37 g, 3.85 mmol) and Celite (2.9 g) in dichloromethane (35 mL). The mixture was stirred overnight, diluted with ethyl acetate (100 mL) and filtered through anhydrous magnesium sulfate. Solids were washed with ethyl acetate. The filtrate was washed with water (twice), dried (magnesium sulfate), filtered and concentrated to obtain aldehyde E (1.3 g crude) as an oil.

F. (5α,6α)-2-[[6-(Benzyloxymethyl)-2,2-dimethyl-1,3-dioxan-5-yl]methyl]benzeneprop-2-enoic acid, methyl ester Methyl(triphenylphosphoridinyl)acetate (2.34 g, 7 mmol) was added to a stirred solution of aldehyde E (1.3 g, 3.67 mmol) in methanol (50 mL). The mixture was stirred overnight, concentrated and chromatographed on a silica gel column. Elution with 10–20% ethyl acetate in hexanes and concentration afforded benzyl ether-ester F (1.26 g, 80% overall from) as a colorless oil.

G. (5α,6α)-2-[[6-(Hydroxymethyl)-2,2-dimethyl-1,3-dioxan-5-yl]methyl]benzenepropanoic acid, methyl ester Palladium hydroxide on charcoal (280 mg, 20% w/w) was added to a stirred solution of ether-ester F (1.42 g, 3.46 mmol) in ethyl acetate (50 mL). The reaction flask was equipped with a hydrogen-filled balloon via three-way stopcock. Air inside the flask was removed under reduced pressure, and it was filled with hydrogen from the balloon. This operation was repeated thrice. After 3 hours, the balloon was removed and anhydrous magnesium sulfate was added to the reaction mixture. It was filtered and residual solids were washed with ether. The filtrate was concentrated to obtain alcohol-ester G (970 mg, 87%) as an oil.

H. (5α,6α)-2-[[6-(t-Butyldiphenylsilyloxymethyl)-2,2-dimethyl-1,3-dioxan-5-yl]-methyl]benzenepropanoic acid, methyl ester A solution of alcohol-ester G (1.3 g, 4.04 mmol) in dichloromethane (20 mL) was treated with triethylamine (2.8 mL, 20 mmol), 4-dimethylaminopyridine (122 mg, 1 mmol) and t-butyldiphenylchlorosilane (2 g, 7 mmol). After 16 hours, the mixture was diluted with ether (150 mL) and washed with 5% aqueous sodium bicarbonate solution (100 mL). The ether extract was dried (magnesium sulfate), filtered and concentrated. The residue was chromatographed on a silica gel column and eluted with hexanes, followed by 2% and 5% ethyl acetate in hexanes to obtain silyl ether-ester H (3.6 g, containing t-butyldiphenylsilanol) as a colorless oil.

I. (2α,5α,6α)-2-[[2-(2-Chlorophenyl)-6-(t-butyldiphenylsilyloxymethyl)-1,3-dioxan-5-yl]methyl]benzenepropanoic acid, methyl ester A solution of ether-ester H (3.6 g, about 4.04 mmol) in dry toluene (14 mL) was treated with 2-chlorobenzaldehyde (4.5 mL, 31.2 mmol) and catalytic p-toluenesulfonic acid. After 5 hours, the mixture was diluted with ether (100 mL) and washed with 5% aqueous sodium bicarbonate solution (25 mL). The ether extract was dried (magnesium sulfate), filtered and concentrated. The residue was chromatographed on a silica gel column and eluted with hexanes, followed by 2% and 5% ethyl acetate in hexanes to obtain chlorophenyl compound I (3.51 g, contained t-butyldiphenylsilanol) a a colorless oil.

J. (2α,5α,6α)-2-[[2-(2-Chlorophenyl)-6-(hydroxymethyl)-1,3-dioxan-5-yl]methyl]-benzenepropanoic acid, methyl ester A solution of compound I (3.51 g, about 4.04 mmol) in dry tetrahydrofuran (30 mL) was treated dropwise at 0°–5° C. with a 1M solution of tetra-n-butylammonium fluoride (6 mL), 6 mmol). After 3.5 hours, the mixture was diluted with ether (125 mL) and washed with water (75 mL), brine (50 mL). The ether extract was dried (magnesium sulfate), filtered and concentrated. The residue was chromatographed on a silica gel column and eluted with 10–50% ethyl acetate in hexanes to obtain alcohol-ester J (1.35 g, 81% overall yield from alcohol-ester G).

K. (2α,5α,6α)-2-[[6-Carboxy-2-(2-chlorophenyl)-1,3-dioxan-5-yl]methyl]benzenepropanoic acid, methyl ester A solution of alcohol-ester J (207 mg, 0.5 mmol) in acetone (6 mL) was treated dropwise at 0°–5° C. with a 2.67M solution of Jones reagent in acetone (1 mL). After 2 hours, additional Jones reagent (0.5 mL) was added, and the mixture was stirred at 0°–5° C. for 1 hour and at room temperature for 1.5 hours. Excess Jones reagent was destroyed by addition of isopropanol at 0°–5° C. The mixture was diluted with ethyl acetate (75 mL) and water (50 mL). The ethyl acetate layer was separated, washed with water (25 mL), dried (magnesium sulfate), filtered and concentrated. The semi-solid residue was triturated with ether/hexanes mixture (1:4, 15 mL) to obtain acid-ester K (140 mg, 65%) as a white solid.

L. [2α,5α,6α(S)]-2-[[2-(2-Chlorophenyl)-6-[[[2-[(4-cyclohexylbutyl)amino]-1-(hydroxymethyl)-2-oxoethyl]amino]carbonyl]-1,3-dioxan-5-yl]methyl]benzenepropanoic acid, methyl ester A solution of acid-ester K (130 mg, 0.3 mmol), N-hydroxybenztyriazole (188 mg, 1.13 mmol) and (4-cyclohexylbutylamido)-S-serine hydrochloride (250 mg, 0.87 mmol) in dimethylformamide (10 mL) was stirred at 0°–5° C. for 5 minutes. Triethylamine (560 μl, 4 mmol) was added dropwise. After 25 minutes, 1-(3-dimethylaminopropyl)-3-ethyl carbodiimide hydrochloride (191 mg, 1 mmol) was added. The mixture was stirred at 0° C. to room temperature for 19 hours, diluted with ethyl acetate (50 mL) and washed with 1N aqueous hydrochloric acid solution (25 mL), saturated sodium bicarbonate solution (25 mL). The ethyl acetate extract was dried (magnesium sulfate), filtered and concentrated. The residue was chromatographed on a silica gel column and eluted with 30–75% ethyl acetate in hexanes to obtain diamide L (110 mg, a mixture of diastereomers contaminated with an unknown UV active product).

M. (2α,5α,6α)-2-[[2-(2-Chlorophenyl)-6-[4-[[(4-cyclohexylbutyl)amino]carbonyl]-4,5-dihydro-2-oxazolyl]-1,3-dioxan-5-yl]-methyl]benzene propanoic acid, methyl ester Triphenylphosphine (327 mg, 1.23 mmol) was added to a stirred solution of diamide L (270 mg, 0.41 mmol) in acetronitrile (6 mL). After a few minutes, N,N-diisopropylethylamine (220 μl, 1.26 mmol) was added. Addition of carbon tetrachloride (400 μl) followed. The mixture was stirred for 8 hours, diluted with ethyl acetate (50 mL) and washed with aqueous sodium bicarbonate solution and brine. The organic extract was dried (magnesium sulfate), filtered and concentrated. The residue was chromatographed on a silica gel column and eluted with 20–60% ethyl acetate in hexanes to obtain oxazoline M (240 mg, contaminated with an unknown UV active product) as a mixture of diastereomers.

N. (2α,5α,6α)-2-[[2-(2-Chlorophenyl)-6-[4-[[(4-cyclohexylbutyl)amino]carbonyl]-2-oxazolyl]-1,3-dioxan-5-yl]methylbenzene propanoic acid, methyl ester Nickel peroxide (180 mg) was added to a stirred solution of oxazoline M (240 mg, 0.37 mmol) in dry methylene chloride (4 mL). The mixture was stirred vigorously at room temperature under an argon atmosphere. Additional nickel peroxide (a total of 1.5 g) was added in 150 mg portions every hour. After 8 hours, the mixture was diluted with ethyl acetate (75 mL) and washed with a 3M solution of sodium bisulfite (50 mL). The ethyl acetate layer was separated, washed with 1M trisodium citrate solution (50 mL) and brine (50 mL). The organic layer was dried (magnesium sulfate), filtered and concentrated. The crude residue was chromatographed on a silica gel column and eluted with hexanes, followed by 10–30% ethyl acetate in hexanes to afford oxazole-ester N (89 mg, 22% overall yield from acid-ester K) as a white solid.

O. (2α,5α,6α)-2-[[2-(2-Chlorophenyl)-6-[4-[[(4-cyclohexylbutyl)amino]carbonyl]-2-oxazolyl]-1,3-dioxan-5-yl]methyl]benzenepropanoic acid A 1M solution of lithium hydroxide in water (2 mL, 2 mmol) was added to a stirred solution of ester N (89 mg, 0.14 mmol) in distilled tetrahydrofuran (6 mL). After 8 hours, the mixture was diluted with ethyl acetate (50 mL) and 0.5N hydrochloric acid solution (50 mL) and saturated brine (50 mL). The ethyl acetate extract was dried (magnesium sulfate), filtered and concentrated. The residual oil was triturated with ether/hexanes (1:4) to obtain Example 21 (75 mg, 86% yield).
Melting point 89°–95° C.
$^1$H NMR (CDCl$_3$): δ 8.4 (s, 1H), 8.0 (m, 1H), 7.2–7.4 (m, 9H), 6.2 (s, 1H), 5.5 (s, 1H), 4.1 (bs, 2H), 2.2–3.6 (m, 9H), 0.9–1.7 (m, 17H).
$^{13}$C NMR (CDCl$_3$): δ 176.9, 161.0, 160.9, 142.2, 139.4, 137.3, 136.7, 135.1, 133.2, 131.4, 131.0, 129.9, 129.5, 128.7, 127.6, 127.4, 127.0, 100.4, 76.8, 68.9, 39.8, 38.7, 38.0, 37.5, 35.6, 33.8, 30.2, 28.3, 27.8, 27.1, 26.8, 24.7.

EXAMPLE 22 cis-2-[[4-[[[2-(4-Chlorophenyl)ethyl]amino]-carbonyl]-2-oxazolyl]-1,3-dioxan-5-yl]methyl]-benzenepropanoic acid A. (5α,6α)-2-[[6-(Benzyloxymethyl)-2,2-dimethyl-1,3-dioxan-5-yl]methyl]benzenepropanoic acid, methyl ester 10% Palladium on charcoal (200 mg, 20% w/w) was added to a stirred solution of olefin F from Example 21 (1.03 g, 2.51 mmol) in ethyl acetate (30 mL). The reaction flask was equipped with a hydrogen filled balloon via three-way stopcock. Air inside the flask was removed under reduced pressure, and it was filled with hydrogen from the balloon. This operation was repeated thrice. After 2 hours, the balloon was removed and anhydrous magnesium sulfate was added to the reaction mixture. It was filtered and residual solids were washed with ether. The filtrate was concentrated to obtain dioxane A (1.01 g, 98%) as an oil.

B. (2R*,3S*)-2-[3-Hydroxy-2-(hydroxymethyl)-4-(benzyloxy)butyl]benzenepropanoic acid, methyl ester A solution of dioxane A (1.01 g, 2.45 mmol) in distilled tetrahydrofuran (20 mL) was treated dropwise with a 1N aqueous hydrochloric acid solution (5 mL). After 6 hours, the mixture was diluted with ethyl acetate (75 mL) and washed with water (100 mL). The aqueous layer was extracted with ethyl acetate (50 mL, 2x). The ethyl acetate extracts were combined, washed with saturated sodium bicarbonate solution (30 mL), brine (30 mL), dried (magnesium sulfate), filtered and concentrated to obtain crude 1,3-diol B (870 mg, 95%) as an oil.

C. (5α,6α)-2-[[6-(Benzyloxymethyl)-1,3-dioxan-5-yl]methyl]benzenepropanoic acid, methyl ester N-bromosuccinimide (833 mg, 4.68 mmol) was added to a stirred solution of diol B (870 mg, 2.34 mmol) in Burdick-Jackson dry dimethylsulfoxide (25 mL). The mixture was heated to 55° C. After 8 hours, additional N-bromosuccinimide (833 mg) was added, and heating was continued for 24 hours. The mixture was cooled, diluted with saturated sodium bicarbonate solution (100 mL) and extracted with ether (100 mL, 3x). The combined ether extract was dried (magnesium sulfate), filtered and concentrated. The residue was chromatographed on a silica gel column and eluted with 10–15% ethyl acetate in hexanes to obtain unsubstituted dioxane C (710 mg, 79%) as an oil.

D. (5α,6α)-2-[[6-(Hydroxymethyl)-1,3-dioxan-5-yl]methyl]benzenepropanoic acid, methyl ester Palladium hydroxide on charcoal (140 mg, 20% w/w) was added to a stirred solution of dioxane benzyl ether C (710 mg, 1.84 mmol) in ethyl acetate (20 mL). The reaction flask was equipped with a hydrogen-filled balloon via three-way stopcock. Air inside the flask was removed under reduced pressure, and it was filled with hydrogen from the balloon. This operation was repeated thrice. After 24 hours, the balloon was removed and anhydrous magnesium sulfate was added to the reaction mixture. It was filtered and residual solids were washed with ether. The filtrate was concentrated to obtain an oil, which was chromatographed on a silica gel column and eluted with 20% ethyl acetate in hexanes, followed by 50% ethyl acetate in hexanes to obtain alcohol D (475 mg, 87%) as an oil.

E. (5α,6α)-2-[[6-Carboxy-1,3-dioxan-5-yl]-methyl] benzenepropanoic acid, methyl ester A solution of alcohol D (430 mg, 1.46 mmol) in acetone (8 mL) was treated dropwise at 0°–5° C. with a 2.67M solution of Jones reagent in acetone (3 mL). After 1.5 hours, additional Jones reagent (1 mL) was added and the mixture was stirred at 0°–5° C. and then at room temperature for 3 hours. Excess Jones reagent was destroyed by addition of isopropanol at 0°–5° C. The mixture was diluted with ethyl acetate (75 mL) and water (100 mL). The ethyl acetate layer was separated, washed with water (50 mL), dried (magnesium sulfate), filtered and concentrated to obtain acid-ester E (390 mg, 87%) as a colorless oil.

F. [5α,6α(S)]-2-[[6-[[[2-[[2-(4-Chlorophenyl)ethyl] amino]-1-(hydroxymethyl)-2-oxoethyl]amino]carbonyl]-1, 3-dioxan-5-yl]-methyl]benzenepropanoic acid, methyl ester A solution of acid-ester E (390 mg, 1.27 mmol), N-hydroxybenztriazole (563 mg, 4.17 mmol) and (2-p-chlorophenylethylamido)-S-serine hydrochloride (700 mg, 2.51 mmol) in dimethylformamide (20 mL) was stirred at 0°–5° C. After a few minutes, triethylamine (1.01 g, 10 mmol) was added dropwise. After 25 minutes, 1-(3-dimethylaminopropyl)-3-ethyl carbodiimide hydrochloride (630 mg, 3.3 mmol) was added. The mixture was stirred at 0° C. to room temperature for 20 hours, diluted with ethyl acetate (100 mL) and washed with 1N aqueous hydrochloric acid solution (50 mL), saturated sodium bicarbonate solution (50 mL). The ethyl acetate extract was dried (magnesium sulfate), filtered and concentrated. The residue was chromatographed on a silica gel column and eluted with 50% ethyl acetate in hexanes, followed by ethyl acetate and 2–5% methanol in ethyl acetate to obtain diamide F (400 mg, a mixture of diastereomers, 51% overall yield from alcohol D) as a foam.

G. (5α,6α)-2-[[6-[4-[[[2-(4-Chlorophenyl)-ethyl]amino] carbonyl]-4,5-dihydro-2-oxazolyl)]-1,3-dioxan-5-yl] methyl]benzenepropanoic acid, methyl ester Triphenylphosphine (654 mg, 2.46 mmol) was added to a stirred solution of diamide F (400 mg, 0.75 mmol) in acetonitrile (15 mL). After a few minutes, N,N-diisopropylethyl amine (440 μl, 2.52 mmol) was added. Addition of carbon tetrachloride (800 μl) followed. The mixture was stirred for 24 hours, diluted with ethyl acetate (100 mL) and washed with aqueous sodium bicarbonate solution and brine. The organic extract was dried (magnesium sulfate), filtered and concentrated. The residue was chromatographed on a silica gel column and eluted with 50% ethyl acetate in hexanes, followed by ethyl acetate and 2–5% methanol in ethyl acetate to obtain oxazoline G (450 mg, contaminated with triphenylphosphine oxide) as a mixture of diastereomers.

H. (5α,6α)-2-[[6-4-[[[2-(4-Chlorophenyl)-ethyl)amino] carbonyl]-2-oxazolyl]-1,3-dioxan-5-yl]methyl] benzenepropanoic acid, methyl ester Nickel peroxide (270 mg) was added to a stirred solution of oxazoline G (450 mg, containing triphenylphosphine oxide) in dry methylene chloride (8 mL). The mixture was stirred vigorously at room temperature under an argon atmosphere. Additional nickel peroxide (a total of 2.02 g) was added in 250 mg portions every hour. After overnight, the mixture was diluted with ethyl acetate (100 mL) and washed with a 3M solution of sodium bisulfite (50 mL). The ethyl acetate layer was separated, washed with 1M trisodium citrate solution (50 mL, 2x) and brine (50 mL). The organic layer was dried (magnesium sulfate), filtered and concentrated. The crude residue was chromatographed on a silica gel column and eluted with 20–50% ethyl acetate in hexanes to afford oxazole-ester H (103 mg, 25% overall yield from diamide F) as an oil.

I. cis-2-[[4-[[[2-(4-Chlorophenyl)ethyl]amino]-carbonyl] -2-oxazolyl]-1,3-dioxan-5-yl]-methyl]benzenepropanoic acid A 1M solution of lithium hydroxide in water (2 mL, 2 mmol) was added to a stirred solution of ester H (103 mg, 0.2 mmol) in distilled tetrahydrofuran (6 mL). After 6 hours, the mixture was diluted with ethyl acetate (50 mL) and acidified with 1N hydrochloric acid solution (4 mL). The mixture was diluted with water (50 mL). The ethyl acetate extract was separated, dried (magnesium sulfate), filtered and concentrated. The residual foam was triturated with ether/hexanes (1:4) to obtain Example 22 (62 mg, 78%) as a white solid.

Melting point 156° 161° C.

EXAMPLE 23

2-[[2-[4-[[(4-Cyclohexylbutyl)amino]carbonyl]-2-oxazolyl]phenyl]methyl]benzenebutanoic acid A. 2-Bromobenzeneethan-1-ol To a solution of 10.0 g (29.1 mmol) of bromide B from Example 8 in 100 mL of dry tetrahydrofuran (distilled from potassium/benzophenone), cooled to 0°, was added dropwise over 20 minutes 44 mL (44 mmol, 1M/tetrahydrofuran) of tetrabutylammonium fluoride solution. The reaction was stirred at 0° for 1.5 hours, then partitioned between 400 mL of ethyl acetate/400 mL of water. The aqueous layer was separated and extracted with two 100-mL portions of ethyl acetate; the combined ethyl acetate layers were dried (magnesium sulfate) and concentrated in vacuo to give a crude yellow oil. The crude oil was flash-chromatographed (Merck silica gel, 50×250 mm, 1:4 ethyl acetate/hexane) to give 5.52 g (27.5 mmol, 94%) of alcohol A as a colorless oil.

B. 1-Bromo-2-(formylmethyl)benzene

To a solution of 5.52 g (27.5 mmol) of alcohol A in 100 mL of dry methylene chloride (distilled from phosphorus pentoxide), stirred at room temperature, was added in several portions 15.1 g (35.7 mmol) of Dess Martin periodinane. The reaction was slightly exothermic. The mixture was stirred at room temperature for 1 hour, then diluted with 1 L of ether/(35 g of sodium thiosulfate in 665 mL of saturated sodium hydrogen carbonate) and stirred until the organic layer was clear. The organic layer was separated and washed with 500 mL of saturated sodium hydrogen carbonate solution, followed by 500 mL of brine. The organic layer was dried (magnesium sulfate) and concentrated in vacuo to give a yellow oil. The crude oil was flash-chromatographed (Merck silica, 50×250 mm, 1:9 ethyl acetate/hexane) to give 3.90 g (19.6 mmol, 71%) of aldehyde B as a colorless oil.

C. 4-(2-Bromophenyl)-2-butenoic acid, methyl ester

To a solution of 8.52 g (25.5 mmol) of methyl (triphenylphosphoranylidene)acetate in 40 mL of dry tetrahydrofuran (distilled from potassium/benzophenone), stirred at room temperature, was added dropwise over 40 minutes a solution of 3.90 g (19.6 mmol) of aldehyde B in 25 mL of dry tetrahydrofuran. The reaction was stirred at room temperature for 16 hours, then the mixture was diluted with 100 mL of hexane and cooled to 0° for 2 hours. The slurry was filtered; the filtrate was concentrated in vacuo to give a yellow solid. The crude solid was flash-chromatographed (Merck silica, 50×250 mm, 2:98 ethyl acetate/(hexane) to give 3.65 g (14.3 mmol, 73%) of alkene C as a colorless oil.

D. 4-(2-Bromophenyl)butanoic acid, methyl ester

To a slurry of 180 mg (0.05 equivalent by weight) of 5% rhodium on alumina in 10 mL of sieve-dried methanol, stirred at room temperature, was added a solution of 3.65 g (14.1 mmol) of alkene C in 30 mL sieve-dried methanol. The reaction vessel was evacuated and filled with hydrogen three times, then stirred under a hydrogen atmosphere (balloon) for 5 hours. The resulting slurry was filtered through a 0.4 micron polycarbonate filter. The filtrate was concentrated in vacuo to give a yellow oil. The crude oil was flash-chromatographed (Merck silica, 50×250 mm, 3:97 ethyl acetate/hexane) to give 3.36 g (13.1 mmol, 92%) of alkane D as a colorless oil.

E. 4-(2-Bromophenyl)-1-butanol

To a solution of 3.36 g (13.1 mmol) of ester D in 10 mL sieve-dried toluene, cooled to 0°, was added dropwise over 30 minutes 29 mL (29 mmol), 1M/toluene) of diisobutyla-luminum hydride solution. The reaction was stirred at 0° for 2.5 hours, then quenched by the dropwise addition of 5 mL of methanol, followed by 60 mL of ice-cold 6M aqueous hydrochloric acid solution. The mixture was stirred at 0° for 30 minutes, then extracted with three-50 mL portions of ether. The combined ether layers were washed with two 50-mL portions of 1M aqueous sodium hydroxide solution and 50 mL of brine, dried over magnesium sulfate and concentrated in vacuo to give a crude oil. The crude oil was flash-chromatographed (Merck silica, 50×250 mm, 1:4 ethyl acetate/hexane) to give 2.56 g (11.2 mmol, 85%) of alcohol E as a colorless oil.

F. 1-Bromo-2-[3-[[dimethyl(1,1,2-trimethyl-propyl)silyl] oxy]butyl]benzene

To a solution of 2.56 g (11.2 mmol) of alcohol E, 1.87 mL (13.4 mmol, distilled from calcium hydride) of triethylamine and 2.39 g (13.4 mmol) of thexyldimethylsilyl chloride in 20 mL of methylene chloride (distilled from phosphorus pentoxide), stirred at room temperature, was added 68 mg (0.56 mmol) of 4-dimethylaminopyridine. The reaction was stirred for 16 hours, then diluted with 100 mL of hexane and cooled to 0° for 2 hours. The resulting slurry was filtered; the filtrate was concentrated in vacuo to give a crude brown oil. The crude oil was flash-chromatographed (Merck silica, 50×250 mm, 5:95 ethyl acetate/hexane) to give 3.85 g (10.4 mmol, 93%) of silyl ether F as a colorless oil, (azeotroped with toluene before use).

G. 2-[2-[[[[(1,1-Dimethylethyl)diphenylsilyl]-oxy] methyl]phenyl]methyl]benzenebutanoic acid, methyl ester To a mixture of 303 mg (12.4 mmol) of freshly hammer-crushed magnesium turnings in 5 mL dry tetrahydrofuran (distilled from sodium/benzophenone) was added a small crystal of iodine followed by 30 μL of 1,2-dibromoethane. The reaction started after heating to 70° (oil bath). After 5 minutes of refluxing, about 20% portion of the required 3.85 g (10.4 mmol) of bromide F was added. An exothermic reaction started with continuous heating (70°); after the reaction color became clear, the remaining bromide was added in one portion. The reaction mixture was refluxed for 2.5 hours at 70°, then the gray solution was cooled to room temperature and 10 mL of tetrahydrofuran was added to insure solubility of the Grignard reagent. The resulting solution was added dropwise over 20 minutes to a solution of 5.05 g (10.4 mmol) of iodide G from Example 5 and 1.0 mL (0.1M in tetrahydrofuran, 0.10 mmol) of freshly prepared dilithium tetrachlorocuprate solution (compound H from Example 5) in 5 mL of dry tetrahydrofuran stirred at 0°. The reaction temperature was maintained below 10° during the addition. The reaction mixture was stirred for an additional 16 hours, then partitioned between 240 mL of saturated aqueous ammonium chloride/100 mL ether. The organic layer was separated, washed with 100 mL of brine, dried (magnesium sulfate) and concentrated in vacuo to give a crude yellow oil.

To a solution of crude oil in 70 mL of reagent acetone, cooled to 0°, was added dropwise 10 mL of Jones reagent (2.6M in $Cr^{+6}$, prepared as described in Fieser & Fieser, Reagents for Organic Synthesis, Vol. 1, p. 142). The reaction mixture was stirred for 2 hours, then the excess reagent was quenched by addition of 15 mL of isopropanol and stirred for an additional 30 minutes. The resulting green slurry was filtered through Celite®. The filtrate was concentrated in vacuo to give a yellow oil. The oil was dissolved in 70 mL of ether, then washed with two 70-mL portions of 5% aqueous sodium bisulfite solution, followed by 50 mL of brine. The resulting solution of the crude acid was cooled to 0° and treated with excess ethereal diazomethane (prepared from 13 g of N-methyl-N'-nitro-N-nitrosoguanidine). After 1 hour, the excess diazomethane was quenched by the addition of glacial acetic acid and the solution was concentrated in vacuo to give a crude oil. The crude oil was flash-chromatographed (Merck silica, 50 x 250 mm, 1:9 ether/hexane) to give 2.53 g (4.71 mmol, 45%) of compound G as a clear oil.

H. 2-[[2-(Hydroxymethyl)phenyl]methyl] benzenebutanoic acid, methyl ester

To a solution of 2.53 g (4.71 mmol) of silyl ether G in 20 mL tetrahydrofuran (distilled from potassium, benzophenone), cooled to 0°, was added dropwise over 15 minutes 7.1 mL (7.1 mmol, 1M/tetrahydrofuran) of tetra-n-butylammonium fluoride solution. The reaction was stirred at room temperature for 4 hours, then the mixture was partitioned between 100 mL of ethyl acetate/100 mL of aqueous 1M hydrochloric acid. The aqueous layer was separated and extracted with two 50-mL portions of ethyl acetate. The combined ethyl acetate layers were dried (magnesium sulfate) and concentrated in vacuo to give a crude yellow oil. The crude oil was flash-chromatographed (Merck silica, 50×200 mm, 1:2 ethyl acetate/hexane) to give 1.06 g (3.56 mmol, 76%) of alcohol H as a colorless oil.

I. 2-[(2-Carboxyphenyl)methyl]benzenebutanoic acid, methyl ester

To a solution of 1.06 g (5.82 mmol) of alcohol H in 40 mL of reagent acetone, cooled to 0°, was added dropwise over 10 minutes 8 mL (2.6M in $Cr^{+6}$, Fieser & Fieser, Vol. 1., p. 142) of Jones reagent. The reaction was stirred at room temperature for 2 hours; the excess Jones reagent was quenched by the addition of 5 mL of isopropanol. The mixture was stirred for 40 minutes, then filtered through Celite®. The filtrate was concentrated in vacuo, then partitioned between 90 mL of 1M hydrochloric acid/90 mL of ethyl acetate; the aqueous layer was separated and extracted with two 40-mL portions of ethyl acetate. The combined ethyl acetate layers were dried (magnesium sulfate) and concentrated in vacuo to give a crude solid. The crude solid was flash-chromatographed (Merck silica, 50×200 mm, 1:1 ethyl acetate/hexane) to give 964 mg (3.09 mmol, 87%) of acid I as a white solid.

J. 2-[[2-[[[2-[(4-Cyclohexylbutyl)amino]-1-(hydroxymethyl)-2-oxoethyl]amino]carbonyl]-phenyl]methyl]benzenebutanoic acid, methyl ester To a solution of 950 mg (3.05 mmol) of acid I in 20 mL of sieve-dried dimethylformamide, cooled to 0°, was added 849 mg (3.05 mmol) of L-serine amine hydrochloride M from Example 5, 541 mg (3.19 mmol, 80%) of hydroxybenztriazole hydrate and 940 μL (6.70 mmol, distilled from calcium hydride) of triethylamine. The mixture was stirred for 5 minutes at 0°, then 613 mg (3.19 mmol) of 1-(3-dimethylaminopropyl)-3-ethylcarbodiimide hydrochloride) was added. The reaction mixture was warmed to room temperature and stirred for 16 hours, then partitioned between 100 mL of ethyl acetate/100 mL of aqueous 1M hydrochloric acid solution. The aqueous layer was separated and extracted with two 50-mL portions of ethyl acetate. The combined ethyl acetate layers were washed with two 100-mL portions of water, dried (magnesium sulfate) and concentrated in vacuo to give a crude solid. The solid was flash-chromatographed (Merck silica, 50×250 mm, methylene chloride load, ethyl acetate elution) to give 1.69 g (3.16 mmol, 103%) of amide J as a white solid.
Melting point: 73°–75°.

K. 2-[[2-[4-[[(4-Cyclohexylbutyl)amino]-carbonyl]-4,5-dihydro-2-oxazolyl]phenyl]-methyl]benzenebutanoic acid, methyl ester A solution of 1.63 g (3.05 mmol) of amide J, 1.19 g (4.57 mmol) of triphenylphosphine and 1.01 mL (5.79 mmol) of diisopropylethylamine in 18 mL of sieve-dried acetonitrile/6 mL of methylene chloride (distilled from phosphorus pentoxide) was stirred at room temperature until homogeneous. To the reaction mixture was added in one portion 440 μL (4.57 mmol) of carbon tetrachloride. The reaction was stirred at room temperature for 16 hours, then the mixture was partitioned between 80 mL of ethyl acetate/100 mL of saturated aqueous sodium hydrogen carbonate solution. The aqueous layer was separated and extracted with two 40-mL portions of ethyl acetate. The combined ethyl acetate layers were washed with 100 mL of water, followed by 50 mL of brine, dried (magnesium sulfate) and concentrated in vacuo to give a crude yellow oil. The crude oil was flash-chromatographed (Merck silica, 50×250 mm, 2:1 ethyl acetate/hexane) to give 1.52 g (2.94 mmol, 97%) of oxazoline K as a pale yellow oil.

L. 2-[[2-[4-[[(4-Cyclohexylbutyl)amino]-carbonyl]-2-oxazolyl]phenyl]methyl]-benzenebutanoic acid, methyl ester To a solution of 1.74 mL (11.6 mmol) of 1,8-diazabicyclo [5.4.0]undec-7-ene in 12 mL ethyl acetate was added 1.29 g (5.80 mmol) of cupric bromide. The mixture was stirred for 10 minutes at room temperature, then cooled in a water bath. A solution of 1.50 g (2.90 mmol) of oxazoline K in 12 mL of chloroform was added dropwise over 10 minutes to the reaction mixture. The reaction was slightly exothermic. The reaction was stirred for 16 hours at room temperature, then a second portion of 1.29 g (5.80 mmol) of cupric bromide was added; after 18 hours, a third portion of 1.29 g (5.80 mmol) of cupric bromide was added. The reaction was stirred for an additional 16 hours at room temperature, then partitioned between 150 mL of 2:1 (saturated aqueous ammonium chloride solution/concentrated ammonium hydroxide/100 mL of ethyl acetate. The aqueous layer was separated and extracted with two 50-mL portions of ethyl acetate. The combined ethyl acetate layers were dried (magnesium sulfate) and concentrated in vacuo to give a crude oil. The crude oil was flash-chromatographed (Merck silica, 50×150 mm, 1:5 ethyl acetate/hexane, then 1:3 ethyl acetate/hexane) to give 611 mg (1.19 mmol, 41%) of oxazole L as a yellow solid.
Melting point: 69°–71°.

M. 2-[[2-[4-[[(4-Cyclohexylbutyl)amino]-carbonyl]-2-oxazolyl]phenyl]methyl]benzenebutanoic acid To a solution of 500 mg (0.97 mmol) of ester L in 8 mL of dry tetrahydrofuran (distilled from potassium, benzophenone)/2 mL of water, stirred at room temperature, was added 82 mg (1.9 mmol) of lithim hydroxide monohydrate. The reaction was stirred vigorously for 16 hours at room temperature and then quenched by the addition of 4 mL (4 mmol) of aqueous 1M hydrochloric acid. The mixture was partitioned between 30 mL of ethyl acetate/30 mL of water, the aqueous layer was separated and extracted with two 20-mL portions of ethyl acetate. The combined ethyl acetate layers were washed with 30 mL of brine, dried (magnesium sulfate) and concentrated in vacuo to give a crude yellow solid. The crude solid was recrystallized from hot ethyl acetate/hexane to give 380 mg (0.76 mmol, 78%) of Example 23 as a white solid.
Melting point: 128°–129°.
IR (KBr): 3219, 3059, 2920, 2851, 1711, 1649, 1595 cm$^{-1}$.
MS (CI): 503 (M+H)$^+$.
TLC: R$_f$(silica gel, 1:9 methanol/methylene chloride)=0.58, ammonium molybdate/cerium disulfate and UV, homogeneous.
Analysis calc'd for $C_{31}H_{38}N_2O_4$: C, 74.08; H, 7.62; N, 5.57
Found: C, 73.96; H, 7.62; N, 5.50

What is claimed is:
1. A compound of the formula

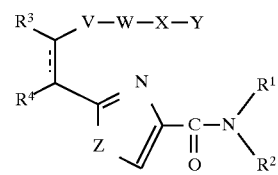

wherein:
V is —(CH$_2$)$_m$—, —O—, or

but if V is —O— or

R$^3$ and R$^4$ must complete
an aromatic ring;
W is —(CH$_2$)$_2$—, —CH=CH— or phenylene;
X is a single bond, —CH=CH—, —(CH$_2$)$_n$—, or —O—(CH$_2$)$_n$—; or X is branched alkylene or —O-branched alkylene wherein W is linked to Y through a straight chain bridge of n carbon atoms;

Y is —CO$_2$H, —CO$_2$alkyl, —CO$_2$alkali metal, —CH$_2$OH, —CONHSO$_2$R$^5$, —CONHR$^6$, or —CH$_2$-5-tetrazolyl;

Z is O or NH;

m is 1, 2, or 3;

n is 1, 2, or 3;

R$^1$ is hydrogen, alkyl, alkenyl, alkynyl, aralkyl, aryl, cycloalkyl, cycloalkylalkyl, cycloheteroalkyl, cycloheteroalkylalkyl, heteroaryl or heteroarylalkyl, or amide, each of R$^1$ being unsubstituted or optionally substituted with alkyl, aryl, cycloalkyl, or cycloalkylalkyl;

R$^2$ is hydrogen, alkyl, aryl, or aralkyl; or

R$^1$ and R$^2$ together with the nitrogen to which they are linked may form a 5- to 8-membered ring;

R$^3$ and R$^4$ are each independently hydrogen or alkyl; or R$^3$ and R$^4$ together complete a cycloalkyl, cycloalkenyl, phenyl, naphthyl, partially saturated naphthyl, pyridinyl, piperidinyl, pyrrolyl, pyrimidinyl, triazinyl, bornanyl, bornenyl, norbornanyl, norbornenyl, bicyclooctanyl, furanyl, pyranyl, dioxanyl, dioxolyl, dioxazolyl, oxazolyl, isoxazolyl, oxazinyl, isoxazinyl, imidazolyl, morpholinyl, oxepinyl, diazepinyl, thiophenyl, thiopyranyl, or thiazolyl ring, optionally substituted through a carbon atom with a halo, lower alkyl, phenyl, halo(lower alkyl), halophenyl, oxo or hydroxyl group;

R$^5$ is alkyl, aryl or aralkyl;

R$^6$ is hydrogen, alkyl, aryl, or aralkyl;

"alkyl" and "alkylene" refer to straight and branched chain groups of 1 to 12 carbon atoms;

"alkenyl" refers to groups of 2 to 12 carbon atoms having at least one double bond;

"alkynyl" refers to groups of 2 to 12 carbon atoms having at least one triple bond;

"cycloalkyl" refers to saturated cyclic hydrocarbon groups of 3 to 8 carbon atoms;

"cycloalkenyl" refers to unsaturated, nonaromatic, cyclic hydrocarbon groups of 5 to 8 carbon atoms;

"aryl" refers to monocyclic or bicyclic aromatic groups of 6 to 10 carbon atoms;

"cycloheteroalkyl" refers to 5-, 6-, or 7-membered saturated rings that include 1 or 2 heteroatoms selected from nitrogen, oxygen and sulfur and that are linked to the "N" of the —NR$^1$R$^2$ group through a carbon atom either beta or gamma to a heteroatom;

"cycloheteroalkylalkyl" refers to 5-, 6-, or 7-membered saturated rings that include 1 or 2 heteroatoms selected from nitrogen, oxygen and sulfur and that are linked to the "N" of the —NR$^1$R$^2$ group through a —(CH$_2$)$_x$— chain wherein x is 1 to 12:

"heteroaryl" refers to 5- or 6-membered rings that include 1 or 2 heteroatoms selected from nitrogen, oxygen and sulfur and that are not linked to the "N" of the —NR$^1$R$^2$ group directly through a heteroatom;

"heteroarylalkyl" refers to 5- or 6-membered rings that include 1 or 2 heteroatoms selected from nitrogen, oxygen and sulfur and that are linked to the "N" of the —NR$^1$R$^2$ group through a —(CH$_2$)$_x$— chain wherein x is 1 to 12: and "amide" refers to groups of the formula —(CH$_2$)$_t$—C(O)—N(H)—R$_a$ or —(CH$_2$)$_t$—N(H)—C(O)—R$_a$ wherein t is 1 to 12 and R$_a$ is alkyl, aryl, cycloalkyl, or cycloalkylalkyl.

2. The compound of claim 1 having the formula

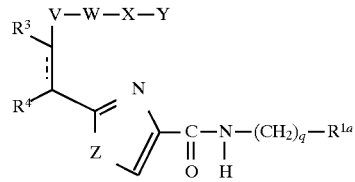

wherein q is an integer from 1 to 7 and R$^{1a}$ is alkyl, cycloalkyl or aryl.

3. The compound of claim 1, wherein X is —(CH$_2$)$_n$— and n is 2.

4. The compound of claim 1, wherein V is —(CH$_2$)$_m$— and m is 1.

5. The compound of claim 1, wherein Y is —CO$_2$H, —CO$_2$alkyl, or —CO$_2$alkali metal.

6. The compound of claim 1 wherein W is phenylene.

7. The compound of claim 2, wherein R$^{1a}$ is cyclohexyl or chlorophenyl.

8. The compound of claim 1 selected from the group consisting of:

(−)cis-2-[[2-[4-[[(4-Cyclohexylbutyl)amino]-carbonyl]-2-oxazolyl]cyclopentyl]methyl]benzenepropanoic acid;

(+)-cis-2-[[2-[4-[[(4-Cyclohexylbutyl)-amino]carbonyl]-2-oxazolyl]cyclopentyl]methyl]-benzenepropanoic acid;

(−)-trans-2-[[2-[4-[[[2-(4-Chlorophenyl)-ethyl]aminocarbonyl]-2-oxazolyl]cyclopentyl]-methyl]benzenepropanoic acid;

(+)-trans-2-[[2-[4-[[[2-(4-Chlorophenyl)-ethyl]amino]carbonyl]-2-oxazolyl]cyclopentyl]-methyl]benzenepropanoic acid;

2-[[2-[4-[[(4-Cyclohexylbutyl)amino]-carbonyl]-2-oxazolyl]phenyl]methyl]benzenepropanoic acid;

2-[[2-[4-[[(3,3-Dimethylbutyl)amino]-carbonyl]-2-oxazolyl]phenyl]methyl]benzenepropanoic acid;

3-[[2-[4-[[(-Cyclohexylbutyl)amino]-carbonyl]-2-oxazolyl]phenyl]methyl]benzeneacetic acid;

2-[[2-[4-[[(4-Cyclohexylbutyl)amino]-carbonyl]-2-oxazolyl]phenyl]methyl]benzeneacetic acid;

3-[[2-[4-[[(4-Cyclohexylbutyl)amino]-carbonyl]-2-oxazolyl]phenyl]methyl]benzenepropanoic acid;

(Z)-2-[3-[[[2-(4-Chlorophenyl)ethyl]amino]-carbonyl]-2-oxazolyl]-2-methyl-2-butenyl]-benzenepropanoic acid;

2-[[2-[4-[[[2-(4-Chlorophenyl)ethyl]amino]-carbonyl]-2-oxazolyl]-1-cyclohexenyl]methyl]-benzenepropanoic acid;

2-[2-[4-[[[2-(4-Chlorophenyl)ethyl]amino]-carbonyl]-2-oxazolyl]benzoyl]benzenepropanoic acid;

2-[[2-[4-[[(4-Cyclohexylbutyl)amino]-carbonyl]-2-oxazolyl]phenyl]carbonyl]benzenepropanoic acid;

2-[2-[4-[[[2-(4-Chlorophenyl)ethyl]amino]-carbonyl]-2-oxazolyl]phenoxy]benzenepropanoic acid;

2-[3-[4-[[(4-Cyclohexylbutyl)amino]-carbonyl]-2-oxazolyl]propyl]benzenepropanoic acid;

cis-2-[[5-[4-[[[2-(4-Chlorophenyl)ethyl]-amino] carbonyl]-2-oxazolyl]-1,3-dioxolan-4-yl]-methyl] benzenepropanoic acid;

(+)-trans)-2-[[5-[4-[[[2-(4-chlorophenyl)-ethyl]amino] carbonyl]-2-oxazolyl]-1,3-dioxolan-4-yl]methyl] benzenepropanoic acid;

(−)-trans)-2-[[5-[4-[[[2-(4-Chlorophenyl)-ethyl]amino] carbonyl]-2-oxazolyl]-1,3-dioxolan-4-yl]methyl] benzenepropanoic acid;

(2α,5α,6α)-2-[[6-[4-[[[2-(4-Chlorophenyl)-ethyl]amino] carbonyl]-2-oxazolyl]-2-methyl-1,3-dioxolan-4-yl] methyl]benzenepropanoic acid;

[2α,5α,6α(Z)]-6-[2-(2-Chlorophenyl)-4-[4-[[(4-cyclohexylbutyl)aminocarbonyl]-2-oxazolyl]-1,3-dioxan-5-yl]-4-hexenoic acid;

(2α,5α,6α)-2-[[6-(2-Chlorophenyl)-4-[4-[[(4-cyclohexylbutyl)amino]carbonyl]-2-oxazolyl]-1,3-dioxan-5-yl]methyl]benzenepropanoic acid;

cis-2-[[6-[[[2-(4-Chlorophenyl)ethyl]amino]-carbonyl]-2-oxazolyl]-1,3-dioxan-5-yl]methyl]-benzenepropanoic acid; and 2-[[2-[6-[[(4-Cyclohexylbutyl)amino]-carbonyl]-2-oxazolyl]phenyl]methyl]benzenebutanoic acid.

9. The compound of claim 1, wherein $R^3$–$R^4$ is cycloalkyl, cycloalkenyl, aryl, alkyl, alkenyl, dioxolanyl or dioxanyl.

10. The compound of claim 2, wherein $R^3$–$R^4$ is cycloalkyl, cycloalkenyl, aryl, alkyl, alkenyl, dioxolanyl or dioxanyl.

11. The compound of claim 1, wherein $R^3$–$R^4$ is cyclopentyl, cyclohexenyl, phenyl, ethyl, butenyl, dioxolanyl or dioxanyl.

12. The compound of claim 2, wherein $R^3$–$R^4$ is cyclopentyl, cyclohexenyl, phenyl, ethyl, butenyl, dioxolanyl or dioxanyl.

13. A method of inhibiting platelet aggregation, which comprises administering to a mammalian host an effective amount of a compound as defined in claim 1.

14. A method of inhibiting bronochoconstriction associated with asthma, which comprises administering to a mammalian host an effective amount of a compound as defined in claim 1.

15. A method of improving post-ischemic myocardial function, which comprises administering to a mammalian host in need of such treatment an effective amount of a compound as defined in claim 1.

16. A method of preventing or reducing venous thrombosis, which comprises administering to a mammalian host in need of such treatment an effective amount of a compound as defined in claim 1.

17. A method of preventing or reducing platelet loss during extracorporeal circulation, which comprises administering to a mammalian host in need of such treatment an effective amount of a compound as defined in claim 1.

18. A method of reducing post-ischemic myocardial injury, which comprises administering to a mammalian host in need of such treatment an effective amount of a compound as defined in claim 1 and an effective amount of a thrombolytic agent within 6 hours of a myocardial infarction.

19. A compound of the formula

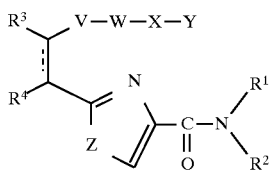

wherein:

V is —$(CH_2)_m$—, —O—, or

but if V is —O— or

$R^3$ and $R^4$ must complete an aromatic ring;

W is —$(CH_2)_2$—, —CH=CH— or phenylene;

X is a single bond, —CH=CH—, —$(CH_2)_n$—, or —O—$(CH_2)_n$—; or X is branched alkylene or —O-branched alkylene wherein W is linked to Y through a straight chain bridge of n carbon atoms;

Y is —$CO_2H$, —$CO_2$alkyl, —$CO_2$alkali metal, —$CH_2OH$, —$CONHSO_2R^5$, —$CONHR^6$, or —$CH_2$-5-tetrazolyl;

Z is O or NH;

m is 1, 2, or 3;

n is 1, 2, or 3;

$R^1$ is hydrogen, alkyl, alkenyl, alkynyl, aralkyl, aryl, cycloalkyl, cycloalkylalkyl, cycloheteroalkyl, cycloheteroalkylalkyl, heteroaryl or heteroarylalkyl, or amide, each of $R^1$ being unsubstituted or optionally substituted with alkyl, aryl, cycloalkyl, or cycloalkylalkyl;

$R^2$ is hydrogen, alkyl, aryl, or aralkyl; or $R^1$ and $R^2$ together with the nitrogen to which they are linked may form a 5- to 8-membered ring;

$R^3$ and $R^4$ are each independently hydrogen or alkyl; or $R^3$ and $R^4$ together complete a cycloalkyl, cycloalkenyl, phenyl, naphthyl, partially saturated naphthyl, pyridinyl, piperidinyl, pyrrolyl, pyrimidinyl, triazinyl, bicyclooctanyl, furanyl, pyranyl, dioxanyl, dioxolyl, dioxazolyl, oxazolyl, isoxazolyl, oxazinyl, isoxazinyl, imidazolyl, morpholinyl, oxepinyl, diazepinyl, thiophenyl, thiopyranyl, or thiazolyl ring, optionally substituted through a carbon atom with a halo, lower alkyl, phenyl, halo(lower alkyl), halophenyl, oxo or hydroxyl group;

$R^5$ is alkyl, aryl or aralkyl;

$R^6$ is hydrogen, alkyl, aryl, or aralkyl;

"alkyl" and "alkylene" refer to straight and branched chain groups of 1 to 12 carbon atoms;

"alkenyl" refers to groups of 2 to 12 carbon atoms having at least one double bond;

"alkynyl" refers to groups of 2 to 12 carbon atoms having at least one triple bond;

"cycloalkyl" refers to saturated cyclic hydrocarbon groups of 3 to 8 carbon atoms;

"cycloalkenyl" refers to unsaturated, nonaromatic, cyclic hydrocarbon groups of 5 to 8 carbon atoms;

"aryl" refers to monocyclic or bicyclic aromatic groups of 6 to 10 carbon atoms;

"cycloheteroalkyl" refers to 5-, 6-, or 7-membered saturated rings that include 1 or 2 heteroatoms selected from nitrogen, oxygen and sulfur and that are linked to the "N" of the $-NR^1R^2$ group through a carbon atom either beta or gamma to a heteroatom;

"cycloheteroalkylalkyl" refers to 5-, 6-, or 7-membered saturated rings that include 1 or 2 heteroatoms selected from nitrogen, oxygen and sulfur and that are linked to the "N" of the $-NR^1R^2$ group through a $-(CH_2)_x-$ chain wherein x is 1 to 12:

"heteroaryl" refers to 5- or 6-membered rings that include 1 or 2 heteroatoms selected from nitrogen, oxygen and sulfur and that are not linked to the "N" of the $-NR^1R^2$ group directly through a heteroatom;

"heteroarylalkyl" refers to 5- or 6-membered rings that include 1 or 2 heteroatoms selected from nitrogen, oxygen and sulfur and that are linked to the "N" of the $-NR^1R^2$ group through a $-(CH_2)_x-$ chain wherein x is 1 to 12: and "amide" refers to groups of the formula

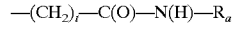

or

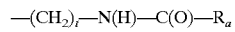

wherein t is 1 to 12 and $R_a$ is alkyl, aryl, cycloalkyl, or cycloalkylalkyl.

* * * * *